United States Patent
Ghandi et al.

(10) Patent No.: US 10,993,437 B2
(45) Date of Patent: *May 4, 2021

(54) ANTI-MICROBIAL POLYMER INCORPORATING A QUATERNARY AMMONIUM GROUP

(71) Applicant: CHEMGREEN INNOVATION INC., Sackville (CA)

(72) Inventors: Khashayar Ghandi, Sackville (CA); Zahid Shabbir Mahimwalla, Sackville (CA); Felix Baerlocher, Sackville (CA)

(73) Assignee: Chemgreen Innovation Inc., Sackville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/418,549

(22) PCT Filed: Jun. 18, 2014

(86) PCT No.: PCT/CA2014/000505
§ 371 (c)(1),
(2) Date: Jan. 30, 2015

(87) PCT Pub. No.: WO2014/201544
PCT Pub. Date: Dec. 24, 2014

(65) Prior Publication Data
US 2016/0100578 A1   Apr. 14, 2016

Related U.S. Application Data

(60) Provisional application No. 61/836,360, filed on Jun. 18, 2013.

(51) Int. Cl.
| | | |
|---|---|---|
| *A01N 33/12* | (2006.01) | |
| *A61L 31/10* | (2006.01) | |
| *A01N 43/90* | (2006.01) | |
| *A61L 27/34* | (2006.01) | |
| *A61Q 17/00* | (2006.01) | |
| *A61K 8/81* | (2006.01) | |
| *D21H 21/36* | (2006.01) | |
| *A61L 31/16* | (2006.01) | |
| *A61L 29/16* | (2006.01) | |

(Continued)

(52) U.S. Cl.
CPC ............ *A01N 33/12* (2013.01); *A01N 37/44* (2013.01); *A01N 43/40* (2013.01); *A01N 43/90* (2013.01); *A61K 8/0208* (2013.01); *A61K 8/817* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *A61Q 17/005* (2013.01); *A61Q 19/10* (2013.01); *B65D 65/42* (2013.01); *B65D 81/24* (2013.01); *C08F 32/00* (2013.01); *C08F 32/02* (2013.01); *C08F 232/00* (2013.01); *C08G 73/026* (2013.01); *C08G 73/0627* (2013.01); *D21H 17/45* (2013.01); *D21H 21/36* (2013.01); *A01N 43/38* (2013.01); *A01N 43/42* (2013.01); *A01N 43/46* (2013.01); *A01N 43/48* (2013.01); *A01N 43/50* (2013.01); *A61L 2300/208* (2013.01); *A61L 2300/404* (2013.01)

(58) Field of Classification Search
CPC ........ A01N 43/34; A01N 43/38; A01N 43/42; A01N 43/40; A01N 43/46; A01N 43/48; A01N 43/50; A01N 43/52; A01N 43/54; A01N 43/60; A01N 43/647; A01N 43/653; A01N 43/66; A01N 33/12; C08F 32/00; C08F 32/02; C08F 34/00; C08F 132/00; C08F 132/02; C08F 132/08; C08F 232/08; C08F 232/02; C08F 232/00; C08F 234/00; C08F 134/00; C08G 73/026; C08G 73/0273; C08G 73/0627; C08G 73/0633; C08G 73/0622; C08G 73/0638; C08G 73/0644; C08G 73/0688; C08G 73/0694
See application file for complete search history.

(56) References Cited

U.S. PATENT DOCUMENTS

| 3,705,938 A | 12/1972 | Hyman et al. |
| 4,826,924 A | 5/1989 | Kourai et al. |

(Continued)

FOREIGN PATENT DOCUMENTS

| CA | 1050677 | 3/1979 |
| CA | 1082382 | 7/1980 |

(Continued)

OTHER PUBLICATIONS

Woo, M. et al. Surface Characterization and Antibacterial Activity of Chitosan-Grafted Polyethylene terephthalate) Prepared by Plasma Glow Discharge. Journal of Applied Polymer Science, vol. 81: 2769-2778 (2001).

(Continued)

*Primary Examiner* — Ling Siu Choi
*Assistant Examiner* — David L Miller
(74) *Attorney, Agent, or Firm* — Bereskin & Parr LLP/S.E.N.C.R.L., s.r.l.; Michael Fenwick

(57) ABSTRACT

The present disclosure relates to antimicrobial polymers which impart prolonged antimicrobial activity to a surface or in a solution, the polymers comprising as repeating monomers a polymerizable cyclic moiety forming part of the polymer backbone and an anti-microbial moiety such as a quaternary ammonium moiety in the side chain. The polymer may further comprise polymerizable units of at least one unsaturated monomer having an ethylenically unsaturated double or triple bond.

6 Claims, 46 Drawing Sheets

(51) Int. Cl.

| | | |
|---|---|---|
| *D21H 17/45* | (2006.01) | |
| *A61Q 19/10* | (2006.01) | |
| *A61K 8/02* | (2006.01) | |
| *A61L 27/54* | (2006.01) | |
| *A61L 29/08* | (2006.01) | |
| *C08F 232/00* | (2006.01) | |
| *C08F 32/02* | (2006.01) | |
| *C08F 32/00* | (2006.01) | |
| *A01N 37/44* | (2006.01) | |
| *A01N 43/40* | (2006.01) | |
| *B65D 65/42* | (2006.01) | |
| *B65D 81/24* | (2006.01) | |
| *C08G 73/02* | (2006.01) | |
| *C08G 73/06* | (2006.01) | |
| *A01N 43/48* | (2006.01) | |
| *A01N 43/38* | (2006.01) | |
| *A01N 43/46* | (2006.01) | |
| *A01N 43/42* | (2006.01) | |
| *A01N 43/50* | (2006.01) | |

(56) References Cited

U.S. PATENT DOCUMENTS

| | | | |
|---|---|---|---|
| 5,049,383 A * | 9/1991 | Huth | A01N 25/04 424/405 |
| 5,320,902 A | 6/1994 | Malhotra et al. | |
| 5,336,305 A | 8/1994 | Staats | |
| 5,417,968 A | 5/1995 | Staats | |
| 5,707,736 A | 1/1998 | Levy et al. | |
| 5,853,641 A | 12/1998 | Nohr et al. | |
| 5,853,883 A | 12/1998 | Nohr et al. | |
| 5,922,313 A | 7/1999 | Steward et al. | |
| 6,034,129 A | 3/2000 | Mandeville, III et al. | |
| 6,214,327 B1 | 4/2001 | Steward et al. | |
| 6,290,947 B1 | 9/2001 | Fitzpatrick et al. | |
| 7,576,047 B2 | 8/2009 | Kilkenny et al. | |
| 7,741,263 B2 | 6/2010 | Kilkenny et al. | |
| 7,799,751 B2 | 9/2010 | Kilkenny et al. | |
| 7,851,541 B2 | 12/2010 | Hodge et al. | |
| 7,951,232 B2 | 5/2011 | Zullo et al. | |
| 7,998,495 B2 | 8/2011 | Argo et al. | |
| 2003/0064102 A1 * | 4/2003 | Nakatsuka | A01N 25/10 424/486 |
| 2003/0100465 A1 | 5/2003 | Kilkenny et al. | |
| 2003/0148917 A1 | 8/2003 | Mitra et al. | |
| 2004/0106533 A1 | 6/2004 | Mitra et al. | |
| 2005/0008534 A1 | 1/2005 | Hodge et al. | |
| 2005/0009971 A1 | 1/2005 | Hodge et al. | |
| 2005/0013794 A1 | 1/2005 | Hodge et al. | |
| 2007/0179079 A1 | 8/2007 | Kilkenny et al. | |
| 2009/0117164 A1 | 5/2009 | Torkeki et al. | |

FOREIGN PATENT DOCUMENTS

| | | |
|---|---|---|
| CA | 1165919 | 4/1984 |
| CA | 1233000 | 2/1988 |
| CA | 1298206 | 3/1992 |
| CA | 1330676 | 7/1994 |
| CA | 2128591 | 3/1999 |
| CA | 2369954 | 11/2000 |
| CA | 2380642 | 2/2001 |
| CA | 2009075 | 4/2001 |
| CA | 2515098 | 9/2004 |
| CA | 2588775 | 6/2006 |
| CA | 2588782 | 6/2006 |
| CA | 2588794 | 6/2006 |
| CA | 2636975 | 7/2007 |
| CA | 2690602 | 12/2008 |
| CA | 2690843 | 12/2008 |
| CA | 2703601 | 4/2009 |
| CA | 2384307 | 6/2009 |
| CA | 2403878 | 2/2010 |
| CA | 2723483 | 2/2010 |
| CA | 2460156 | 8/2010 |
| CA | 2783619 | 6/2011 |
| CA | 2785709 | 7/2011 |
| CA | 2492521 | 11/2012 |
| EP | 1633192 | 5/2010 |
| WO | WO2007/084452 | 7/2007 |
| WO | WO2008/082293 | 7/2008 |
| WO | WO2009/137016 | 11/2009 |

OTHER PUBLICATIONS

Kenawy, E-R et al. The Chemistry and Applications of Antimicrobial Polymers: A State-of-the-Art Review. Biomacromolecules, vol. 8(5):1359-1384, 2007.

Vasilev, K. Antibacterial surfaces for biomedical devices. Expert Rev. Med. Devices 6(5):553-567, 2009.

Zhou, F. et al. Antibacterial Characteristics of Novel Gemini-type Quaternary Ammonium Salt Bonded to Cotton Fiber. Journal of Fiber Bioengineering and Informatics. vol. 1(2):85-92, 2008.

Banerjee, I. et al. Antifouling Coatings: Recent Developments in the Design of Surfaces That Prevent Fouling by Proteins, Bacteria, and Marine Organisms. Adv. Mater. 23:690-718, 2011.

Lichter, J.A. et al. Design of Antibacterial Surfaces and Interfaces: Polyelectrolyte Multilayers as a Multifunctional Platform. Macromolecules. 42:8573-8586, 2009.

Kocer, H.B. et al. N-Halamine Copolymers for Use in Antimicrobial Paints. Appl. Mater. Interfaces, 3:3189-3194, 2011.

Kocer, H.B. et al. Polymeric Antimicrobial N-Halamine Epoxides. Appl. Mater. Interfaces, 3:2845-2850, 2011.

Moore, A.J. Journal of Antimicrobial Chemotherapy. 37:1077-1089, 1996.

Lowe, D.B. Nowhere to Go But Up: The Return of Medicinal Chemistry. ACS Med. Chem. Lett. 3:3-4, 2012.

Liu, S. et al. New Refreshable N-Halamine Polymeric Biocides: N-Chlorination of Acyclic Amide Grafted Cellulose. Ind. Eng. Chem. Res. 48:613-618, 2009.

Liu, S. et al. Durable and Regenerable Biocidal Polymers: Acyclic N-Halamine Cotton Cellulose. Ind. Eng. Chem. Res. 45:6477-6482, 2006.

* cited by examiner

ANTI-MICROBIAL POLYMER INCORPORATING A QUATERNARY AMMONIUM GROUP

This application is a national phase entry of PCT/CA2014/000505, filed Jun. 18, 2014, which claims priority from U.S. Provisional patent application Ser. No. 61/836,360 filed Jun. 18, 2013, each of these applications being incorporated herein in their entirety by reference.

FIELD

The present disclosure relates to anti-microbial polymers and polymer composites comprising a polymerizable cyclic moiety which forms part of the backbone of the polymer.

INTRODUCTION

Antimicrobial compounds and materials are chemicals capable of reducing or inhibiting the growth and development of microbial organisms such as fungi and bacteria. Such compounds play an important role in a variety of applications and fields including human health, by helping the prevention and treatment of microorganism linked diseases, fish and animal farming, preventing the decomposition of materials e.g. polyurethanes, wood and other construction materials, preservation of food from spoilage by various micro-organisms, disinfecting surfaces to prevent the transmission of various infectious microorganisms etc.

Current technology generally relies on incorporating anti-microbial compounds into materials with a delayed release mechanism, or by incorporating the compounds into polymeric materials at the processing (i.e. extrusion molding etc.) or post-processing stage such as coatings. In both instances the antimicrobial compounds leach out over time, depleting the effectiveness of the material, and in the case of toxic biocides can lead to adverse outcomes for human health, the environment or the intended application and material performance.

SUMMARY

The present disclosure relates to novel anti-microbial polymers. In particular, the disclosure relates to anti-microbial polymers and polymer composites composed of repeating and polymerizable units of
  i) at least one monomer comprising a polymerizable cyclic moiety wherein the cyclic moiety forms part of the polymer backbone, and wherein the monomer further comprises an anti-microbial moiety.

In one embodiment, the at least one monomer comprising a polymerizable cyclic moiety comprises an anti-microbial moiety, which results in the anti-microbial polymer having anti-microbial activity. In one embodiment, the anti-microbial moiety comprises a quaternary aromatic ammonium salt, a quaternary cyclic aromatic ammonium salt, or quinone or quinone derivative.

In another embodiment, the disclosure relates to anti-microbial polymers and polymer composites composed of repeating and polymerizable units of
  i) at least one monomer comprising a polymerizable cyclic moiety wherein the cyclic moiety forms part of the polymer backbone, and wherein the monomer further comprises an anti-microbial moiety; and
  ii) at least one unsaturated monomer having an ethylenically unsaturated double or triple bond.

Also included in the present disclosure are anti-microbial devices such as stents, in which the devices have been coated with the anti-microbial polymer of the present disclosure.

Also included in the present disclosure are medical devices which are composed of anti-microbial polymers of the present disclosure, for example a stent composed of an anti-microbial polymer of the disclosure.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DRAWINGS

The disclosure will now be described in greater detail with reference to the following drawings in which.

DESCRIPTION OF VARIOUS EMBODIMENTS (I) Definitions

Figure 1:
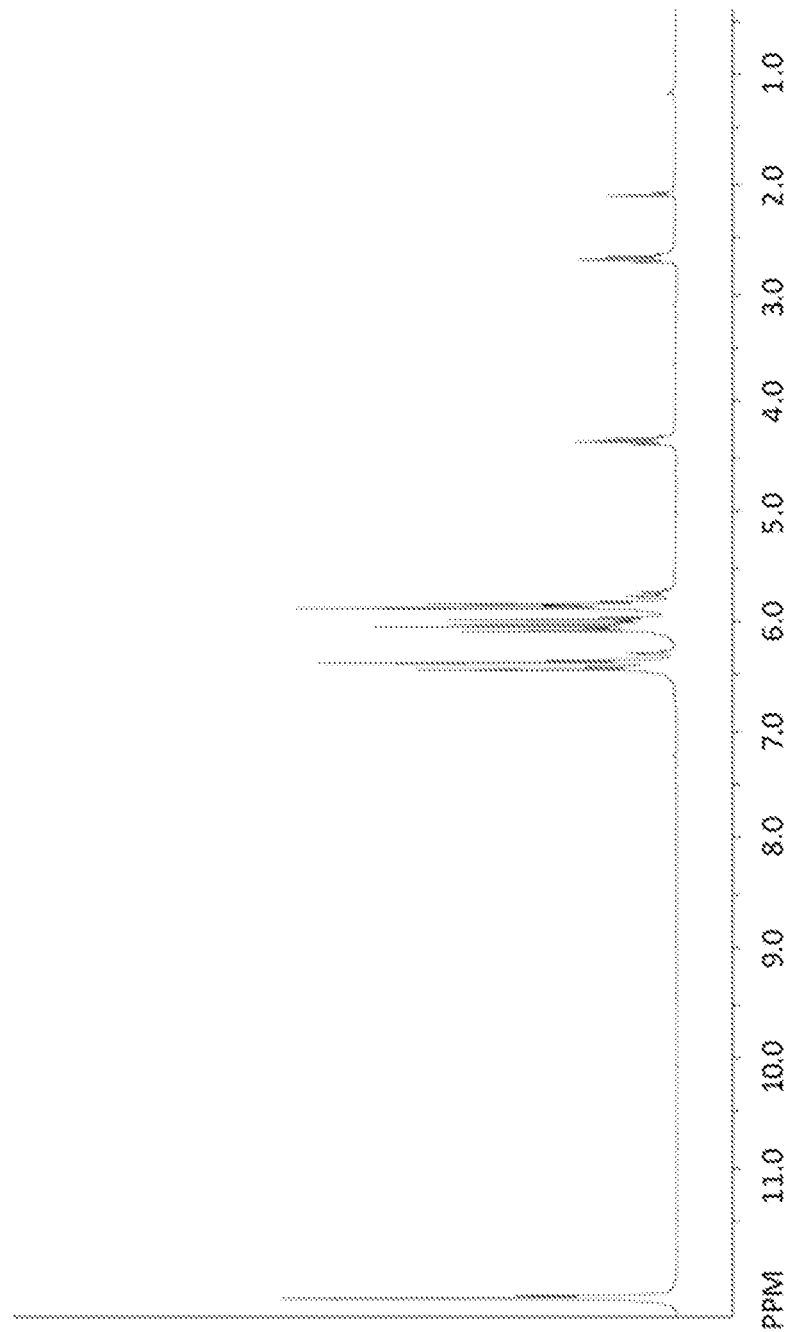
FIG. 1 is an NMR spectrum of a PAA-BZ polymer product in an embodiment of the disclosure.

The term "anti-microbial polymer" as used herein refers to polymers of the present disclosure which kill, inhibit, and/or reduce microbial growth, for example, by inhibiting the proliferation or viability of a microbe which is undesirable and/or which disrupts a microbial cell. Microbes includes bacteria, viruses, fungi, protozoa and the like.

The term "polymerizable cyclic moiety" as used herein refers to an unsaturated moiety of a monomer which can participate in a polymerization reaction. The unsaturated group or moiety may be an aromatic or non-aromatic moiety which can participate in a polymerization reaction. The unsaturated moiety, for example, a benzene ring, directly participates in the polymerization reaction to form part of the backbone of the polymer that is prepared from the reaction.

The term "polymer backbone" as used herein refers to the covalently bonded chain of repeating monomer units that form the polymer. As would be understood, the polymer backbone may be covalently attached to terminal functional groups or pendant functionalized side chains spaced along the polymer backbone.

The term "anti-microbial moiety" as used herein refers to a moiety, within the monomer comprising the polymerizable cyclic moiety, that possesses anti-microbial activity and which can therefore reduce kill, inhibit and/or reduce microbial growth. The anti-microbial activity of the prepared anti-microbial polymer exhibit similar or greater anti-microbial properties compared to the individual monomers which form the polymer.

The term "anti-microbial moiety" also includes monomers which possess little or no anti-microbial activity, but exhibit anti-microbial properties upon polymerization to form the anti-microbial polymer.

The term "ethylenically unsaturated" as used herein refers to monomers having terminal, internal or pendant ethylenic unsaturation or any combination thereof and which can participate in a polymerization reaction. The ethylenic unsaturation may be a double or triple carbon-carbon bond.

The term "aromatic" as used herein with respect to the polymerizable cyclic moiety refers to a planar, cyclic or polycyclic, ring moiety having a delocalized π-electron system containing 4n+2 π electrons, where n is an integer. Aromatic rings can be formed by five, six, seven, eight, nine, or more than nine atoms. Aromatics can be optionally substituted and can be monocyclic or fused-ring polycyclic.

The term aromatic encompasses both all carbon containing rings (e.g., phenyl) and those rings containing one or more heteroatoms (e.g., pyridine).

The term "conjugated" as used herein with respect to the polymerizable cyclic moiety refers to a moiety having two or more double and/or triple bonds, each double or triple bond being separated from the next consecutive double or triple bond by a single bond so that π orbitals overlap not only across the double or triple bond, but also across adjacent single bonds located between adjacent double and/or triple bonds. The double or triple bonds may be carbon-carbon bonds or carbon-heteratom bonds, such as carbonyl or imine moieties.

The term "quarternary ammonium moiety" or "quarternary phosphonium moiety" as used herein refers to a moiety having four bonds to the nitrogen or phosphorous atom with a positive charge on the nitrogen or phosphorous in the "onium" state, i.e., "$R_4N^+$" or "quaternary nitrogen," wherein R is an organic substituent such as alkyl or aryl. The term "quaternary ammonium salt" or "quaternary phosphonium salt" as used herein refers to the association of the quaternary ammonium or phosphonium with a cation.

The term "quinone" as used herein refers to mono- and poly-nuclear quinones such as benzoquinone, naphthoquinones, anthraquinones, phenanthraquinone, camphor-quinone and addition products and substituted derivatives thereof. The term "quinone" also includes isomers of such quinones. The quinones may contain substitution groups such as halogens, amino, alkyl, aryl, alkaryl, aralkyl, alkoxy, aroxyl, hydroxy and other substituent groups.

The term "quaternary aromatic ammonium or phosphonium" as used herein refers to a quaternary ammonium or phosphonium moiety as referred to herein, in which the monomer contains an aromatic moiety and a quarternary ammonium or phosphonium moiety, and in which the quarternary ammonium or phosphonium moiety does not form part of the aromatic ring. Examples of quaternary aromatic ammonium salts include, but are not limited to, benzalkonium chlorides (such as stearalkonium chloride, tetradecylammonium chloride), benzoxonium chloride, domiphen bromide, tibezonium chloride, benzethonium chloride, thonozium bromide, biphenium hydroxynaphthoate, etc. Examples of quaternary aromatic phosphonium salts include, but are not limited to, benzyltriphenylphosphonium chloride, benzyltriphenylphosphonium bromide, triphenyl-(3,4,5-trimethoxy-benzyl)-phosphonium bromide, benzyltriethylphosphonium chloride, benzyltributylphosphonium chloride, trimethylphenylphosphonium iodide, dimethyldiphenylphosphonium iodide, ethyl triphenyl phosphonium iodide, butyl triphenyl phosphonium bromide, methyl triphenyl phosphonium bromide.

The term "quaternary cyclic aromatic ammonium or phosphonium salt" as used herein refers to a quaternary ammonium moiety as referred to herein, in which the monomer contains an aromatic moiety and a quarternary ammonium moiety, in which the quarternary ammonium moiety forms part of the aromatic ring. Examples of quaternary cyclic aromatic ammonium salts include, but are not limited to, acriflavinium chloride, cetylpyrdinium chloride, chelerythrine, dequalinium, isometamidium chloride, ethidium bromide, diquat, MPP+ (1-methyl-4-phenylpyridinium) etc.

The term "aryl" as used herein means a monocyclic, bicyclic or tricyclic aromatic ring system containing, depending on the number of atoms in the rings, for example from 6 to 14 carbon atoms, and at least 1 aromatic ring and includes phenyl, naphthyl, anthracenyl, 1,2-dihydronaphthyl, 1,2,3,4-tetrahydronaphthyl, fluorenyl, indanyl, indenyl and the like.

The term "heteroaryl" or "heteroaromatic" as used herein means a monocyclic, bicyclic or tricyclic ring system containing one or two aromatic rings, and from 5 to 14 atoms, optionally 5 or 6 atoms, of which, unless otherwise specified, one, two, three, four or five are a heteromoiety independently selected from N, NH, $NC_{1-6}$ alkyl, O and S and includes thienyl, furyl, pyrrolyl, pyrididyl, indolyl, quinolyl, isoquinolyl, tetrahydroquinolyl, benzofuryl, benzothienyl and the like.

The term "$(C_1-C_p)$_alkyl" as used herein means straight and/or branched chain, saturated alkyl radicals containing from one to "p" carbon atoms and includes (depending on the identity of p) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical.

The term "$(C_2-C_p)$alkenyl" as used herein means straight or branched chain, unsaturated alkyl groups containing from two to p carbon atoms and one to three double bonds, and includes (depending on the identity of p) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable p is an integer representing the largest number of carbon atoms in the alkenyl radical.

The term "$(C_2-C_p)$alkynyl" as used herein means straight and/or branched chain, unsaturated alkyl groups containing from one to n carbon atoms and one or more, suitably one to three, triple bonds, and includes (depending on the identity of p) ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl4-methylpent-2-ynyl, 1-hexynyl and the like, where the variable n is an integer representing the largest number of carbon atoms in the alkynyl group.

The term "alkoxy" as used herein, alone or in combination, refers to an alkyl ether radical, —O-alkyl, wherein the alkyl group may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "counteranion" as used herein refers to a negatively charged species consisting of a single element, or a negatively charged species consisting of a group of elements connected by ionic and/or covalent bonds. Examples of suitable counteranions include, but are not limited to, the halides, for example chloro or bromo.

The suffix "ene" added on to any of the above groups means that the group is divalent, i.e. inserted between two other groups.

The term "halo" or "halogen" as used herein means halogen and includes chloro, fluoro, bromo and iodo.

(II) Detailed Description

The present disclosure relates to anti-microbial polymers, which when in contact with the polymer, kill, inhibit and/or reduce microbial growth, or prevent the growth of microbes, including bacteria, fungi, viruses, protozoa, etc. The anti-microbial polymers of the present disclosure are prepared from monomers comprising a polymerizable cyclic moiety, in which the cyclic moiety forms part of the polymer backbone. Such monomers may have anti-microbial properties as the monomers themselves, or become anti-microbial after polymerization, such that the anti-microbial polymer has similar or greater anti-microbial properties than the monomers alone.

In one embodiment therefore, the present disclosure includes an anti-microbial polymer, comprising polymerizable units of
i) at least one monomer comprising a polymerizable cyclic moiety wherein the cyclic moiety forms part of the polymer backbone, and wherein the monomer further comprises an anti-microbial moiety.

In another embodiment, the present disclosure includes an anti-microbial polymer, comprising polymerizable units of
i) at least one monomer comprising a polymerizable cyclic moiety wherein the cyclic moiety forms part of the polymer backbone, and wherein the monomer further comprises an anti-microbial moiety; and
ii) at least one unsaturated monomer having an ethylenically unsaturated double or triple bond.

In one embodiment, the polymerizable cyclic moiety comprises a radically polymerizable cyclic moiety.

In another embodiment, the polymerizable cyclic moiety comprises an aromatic polymerizable cyclic moiety or a conjugated polymerizable cyclic moiety. In one embodiment, the aromatic polymerizable cyclic moiety or the conjugated polymerizable cyclic moiety is unactivated.

In another embodiment, the anti-microbial moiety comprises a quaternary ammonium moiety, a quaternary phosphonium moiety or a moiety derived from quinones. In one embodiment, the at least one monomer comprising a polymerizable cyclic moiety comprises a quaternary aromatic ammonium or phosphonium salt, a quaternary cyclic aromatic ammonium or phosphonium salt, or quinone or quinone derivative.

In one embodiment, one monomer has at least one double or triple bond.

In another embodiment of the disclosure, the quaternary aromatic ammonium or phosphonium salt comprises a monomer of the formula wherein
Ar is optionally substituted $(C_6-C_{14})$-aryl or optionally substituted $(C_5-C_{14})$-heteroaryl, Y is absent, $(C_1-C_{10})$-alkylene, $(C_2-C_{10})$-alkenylene, or $(C_2-C_{10})$-alkynylene, wherein 1 or 2 carbon atoms are optionally replaced with N, S or O;
$R_1$, $R_2$ and $R_3$ are independently or simultaneously optionally substituted H, $(C_1-C_{24})$-alkyl, $(C_2-C_{24})$-alkenyl, $(C_2-C_{24})$-alkynyl, $(C_6-C_{14})$-aryl, $(C_5-C_{14})$-heteroaryl or $(C_1-C_{10})$-alkylene-$(C_6-C_{14})$-aryl,
wherein the optional substituents are chosen from one or more of halogen, hydroxyl, $(C_1-C_6)$-alkyl, $(C_1-C_6)$-alkoxy, thionyl, nitro, amino (—NH$_2$), $(C_6-C_{14})$-aryl or $(C_5-C_{14})$-heteroaryl,
M is nitrogen or phosphorous, and
X is any suitable counteranion, such as halo.

In another embodiment, Ar is optionally substituted phenyl, naphthyl, anthracenyl, 1,2-dihydronaphthyl, 1,2,3,4-tetrahydronaphthyl, fluorenyl, indanyl, indenyl, thienyl, furyl, pyrrolyl, pyrididyl, indolyl, quinolyl, isoquinolyl, tetrahydroquinolyl, benzofuryl, or benzothienyl. In one embodiment, Ar is optionally substituted phenyl.

In another embodiment, Y is $(C_1-C_6)$-alkylene, $(C_2-C_6)$-alkenylene, or $(C_2-C_6)$-alkynylene, wherein 1 or 2 carbon atoms are optionally replaced with O, optionally $(C_1-C_6)$-alkylene, in which one of the carbon atoms is optionally replaced with O.

In a further embodiment, $R_1$, $R_2$ and $R_3$ are independently or simultaneously $(C_1-C_{24})$-alkyl, $(C_2-C_{24})$-alkenyl, $(C_2-C_{24})$-alkynyl, or $(C_1-C_{10})$-alkylene-$(C_6-C_{14})$-aryl, optionally $(C_1-C_{24})$-alkyl or $(C_1-C_{20})$-alkyl. In one embodiment, $R_1$, $R_2$ and $R_3$ are independently or simultaneously $(C_1-C_6)$-alkylene-phenyl.

In one embodiment, the quaternary aromatic ammonium salt comprises a monomer of the formula wherein
Y' is $(C_1-C_3)$-alkylene, wherein 1 carbon atom is optionally replaced with O;
$R_1'$ and $R_2'$ are independently or simultaneously $(C_1-C_4)$-alkyl optionally substituted with —OH;
$R_3'$ is $(C_1-C_{24})$-alkyl or $(C_1-C_{10})$-alkylene-$(C_6-C_{14})$-aryl, and
R is one or more optional substituents chosen from halogen, $(C_1-C_6)$-alkyl, thionyl, nitro, $(C_6-C_{14})$-aryl or $(C_5-C_{14})$-heteroaryl, and
X is halo.

In one embodiment, Y is —CH$_2$CH$_2$O— or CH$_2$.

In another embodiment, the quaternary aromatic ammonium salt comprises a compound selected from In another embodiment, the quaternary aromatic ammonium salt comprises a compound selected from

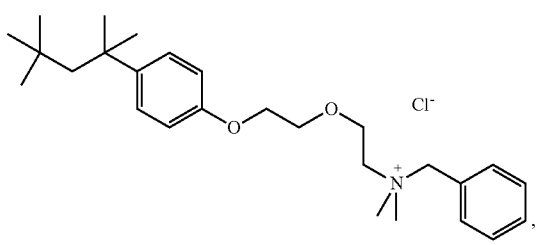

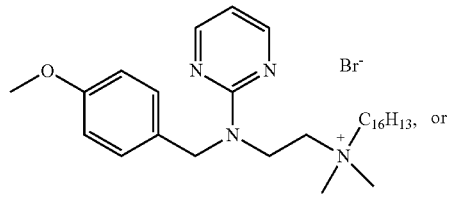

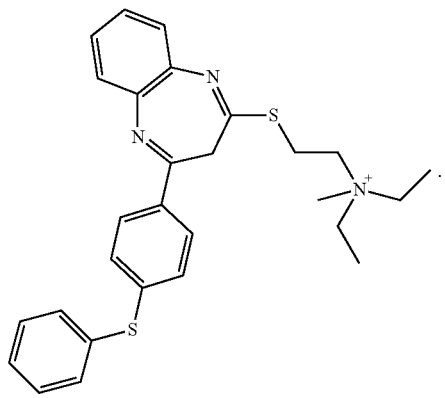

In another embodiment, the quaternary aromatic phosphonium salt comprises

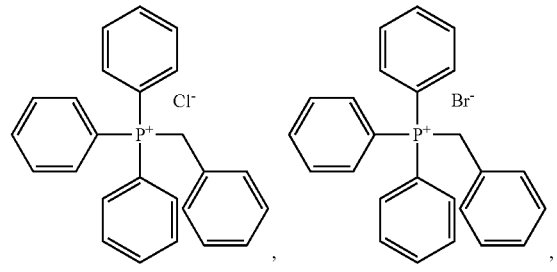

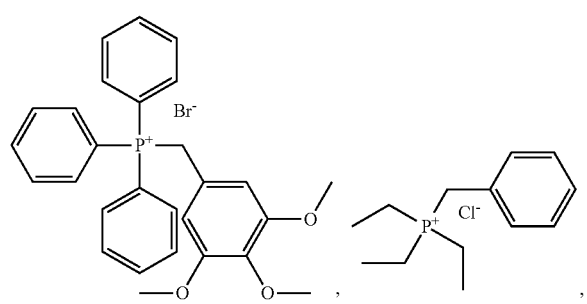

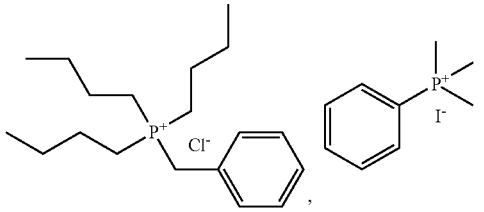

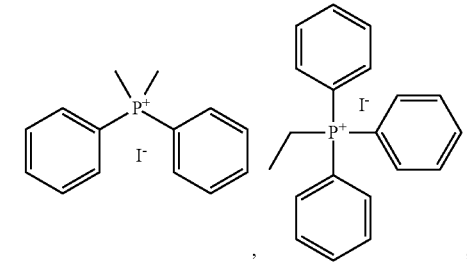

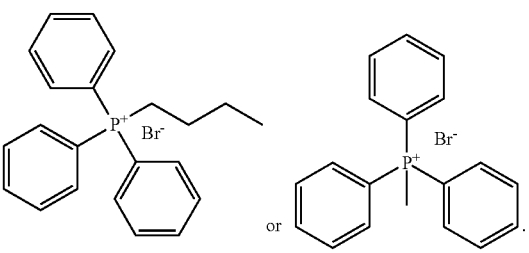

In another embodiment of the disclosure, the quaternary aromatic ammonium salt comprises a monomer of the formula

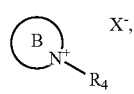

wherein

Ring B is an optionally substituted aromatic moiety containing from 5 to 18 carbon atoms, in which from 0 to 4 carbon atoms are replaced with a heteroatom selected from N, O and S, $R_4$ is H, $(C_1-C_{24})$-alkyl, $(C_2-C_{24})$-alkenyl, $(C_2-C_{24})$-alkynyl, $(C_6-C_{14})$-aryl or $(C_5-C_{14})$-heteroaryl, wherein the optional substituents are chosen from one or more of halogen, —OH, $(C_1-C_6)$-alkyl, $(C_1-C_6)$-alkoxy, thionyl, nitro, amino (—$NH_2$), $(C_6-C_{14})$-aryl, $(C_5-C_{14})$-heteroaryl, or two adjacent substituents are joined to form a methylene dioxy moiety, and X is any suitable counteranion, such as halo.

In one embodiment, Ring B is an optionally substituted aromatic moiety containing from 5 to 14 carbon atoms, in which from 0 to 2 carbon atoms are replaced with a heteroatom selected from N, O and S.

In one embodiment, $R_4$ is H or $(C_1-C_{24})$-alkyl, such as —$CH_3$, —$CH_2CH_3$ or —$C_{16}H_{33}$.

In another embodiment, the quaternary aromatic ammonium salt comprises a monomer of the formula

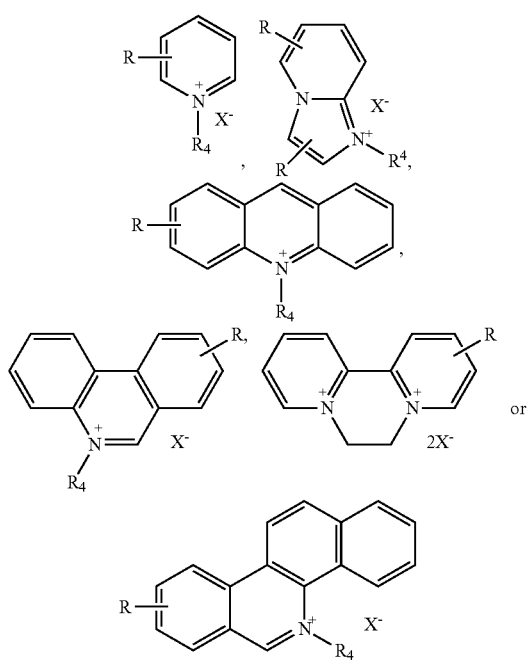

wherein

R₄ is H, $(C_1-C_{24})$-alkyl, $(C_2-C_{24})$-alkenyl, $(C_2-C_{24})$-alkynyl, $(C_6-C_{14})$-aryl or $(C_5-C_{14})$-heteroaryl, R is one or more optional substituents chosen from halogen, —OH, $(C_1-C_6)$-alkyl, $(C_1-C_6)$-alkoxy, thionyl, nitro, amino (—NH₂), $(C_6-C_{14})$-aryl, $(C_5-C_{14})$-heteroaryl, or two adjacent substituents are joined to form a methylene dioxy moiety, and X is any suitable counteranion, such as halo.

In one embodiment, R₄ is H or $(C_1-C_{24})$-alkyl, such as —CH₃, —CH₂CH₃ or —C₁₆H₃₃.

In one embodiment, the quaternary aromatic ammonium salt is a monomer of the formula

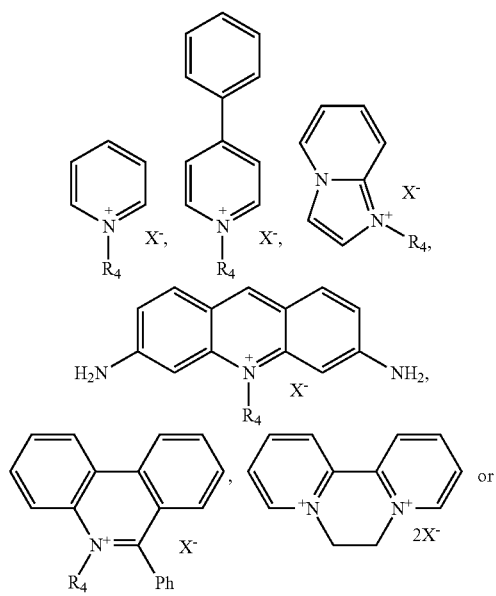

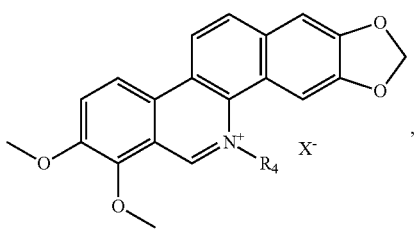

wherein

R₄ is H or $(C_1-C_{24})$-alkyl, and

X is any suitable counteranion, such as halo.

In another embodiment, the quaternary aromatic ammonium salt is

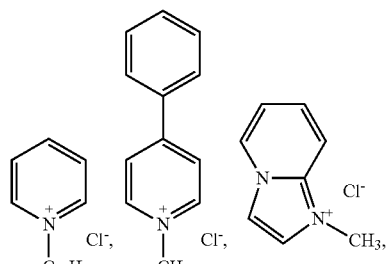

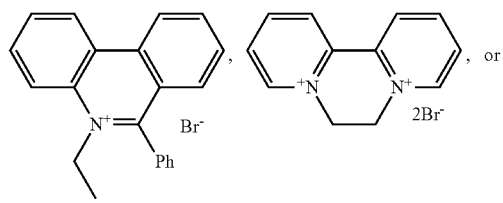

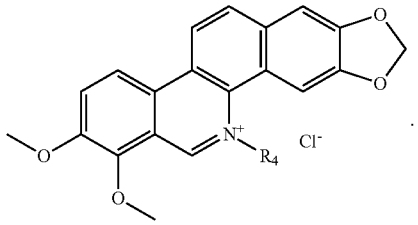

In one embodiment, the quaternary aromatic ammonium salt is

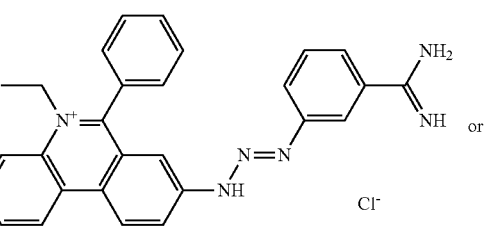

-continued

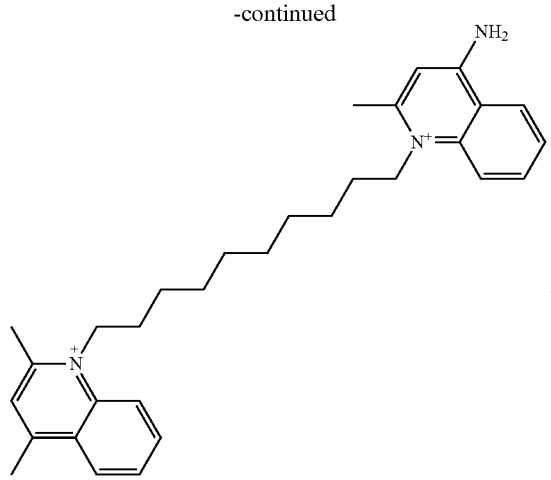

In another embodiment of the disclosure, the quinone or quinone derivative is a monomer of the formula

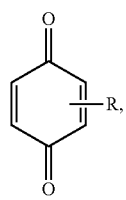

R is one or more optional substituents chosen from halogen, OH, $(C_1\text{-}C_6)$-alkyl, $(C_1\text{-}C_6)$-alkenyl, $(C_1\text{-}C_6)$-alkoxy, thionyl, nitro, $(C_6\text{-}C_{14})$-aryl, $(C_5\text{-}C_{14})$-heteroaryl, or two or more adjacent substituents are joined together to form an optionally substituted aromatic or non-aromatic monocyclic or polycyclic ring.

In one embodiment, quinone or quinone derivative is a monomer of the formula

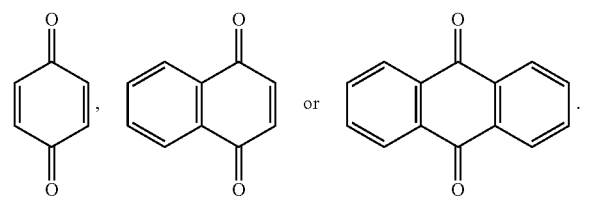

In another embodiment of the disclosure, the at least one monomer comprising a polymerizable cyclic moiety comprises

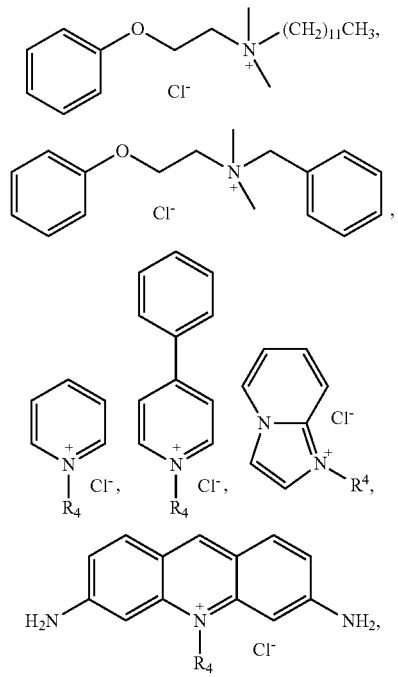

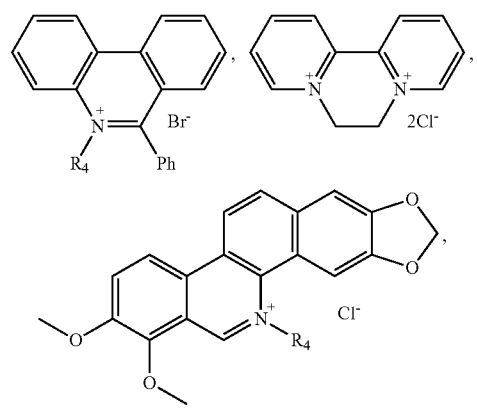

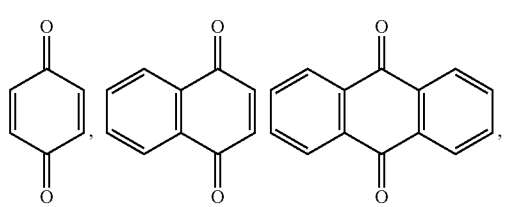

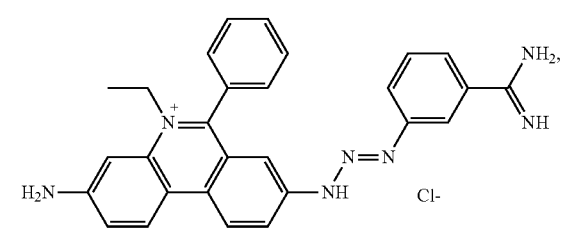

-continued

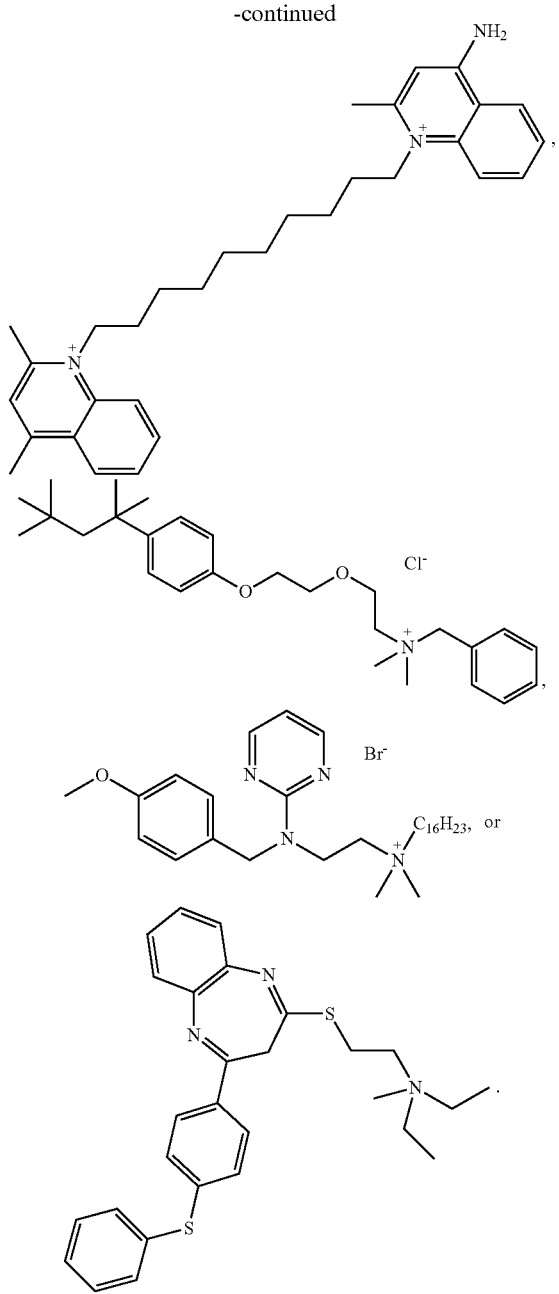

In one embodiment, the monomer comprising a polymerizable cyclic moiety is present within the anti-microbial polymer at a mole fraction of between 0.00001 to 0.99, or about 0.001 to about 0.90. In one embodiment, the mole fraction is between about 0.1 to about 0.5, or about 0.2 to about 0.4, or about 0.2 to about 0.3. In one embodiment, the monomer comprising a polymerizable cyclic moiety is present as a mole fraction in the overall anti-microbial polymer of about 0.20, or about 0.22, or about 0.23.

In another embodiment, the at least one unsaturated monomer having an ethylenically unsaturated double or triple bond is any monomer having such unsaturation which participates in the polymerization reaction to form the anti-microbial polymers of the present disclosure. Many ethylenically unsaturated monomers are known to those skilled in the art.

In one embodiment, the at least one unsaturated monomer having an ethylenically unsaturated double or triple bond comprises
(i) acrylic acid, acrylates and acrylate salts, such as methacrylates;
(ii) styrene and styrene derivatives;
(iii) vinylpyridines, such as 4-vinylpyridine,
(iv) acrylamides,
(v) propylene, polypropylene and polypropylene derivatives,
(vi) ethylene, polyethylene and polyethylene derivatives,
(vii) vinylchlorides,
(viii) alkenes and alkynes,
(ix) $(C_2\text{-}C_{20})$-alkene, polyalkene, $(C_2\text{-}C_{20})$-alkyne and polyalkyne polyols, such as polybutadiene diols and triols, polyisobutylene diols and triols, polybutylene oxide diols and triols, such as 2-butyne-1,4-diol, or cis-2-butene-1,4-diol,
(x) aromatic polyols, such as benzene-diol, benzene-1,2-dithiol,
(xi) di-carboxylic acids, such as maleic acid, fumaric acid, phthalic acid, glutaconic acid,
(xii) cellulose and cellulose derivatives,
(xii) vinyl acetate and vinyl acetate derivatives,
(xiv) allyl ethers, such as pentaerythritol allyl ether or allyl sucrose;
(xv) terpenes and terpenoids, such as linolool, citronellol, or geraniol,
(xvi) acrylated derivatives of epoxidized oils, such as acrylated epoxidized soybean oil,
(xvii) essential oils or derivatives of plant oils containing polymerizable components with an ethylenically unsaturated double or triple bond, co-polymers thereof or polymers thereof, wherein any of the above monomers are optionally fluoro-substituted.

In one embodiment, the at least one monomer having an ethylenically unsaturated double or triple bond comprises acrylic acid, acrylates, styrene, or a vinylpyridine. In one embodiment, the at least one monomer having an ethylenically unsaturated double or triple bond is vinyl acetate.

In another embodiment, the monomer comprises

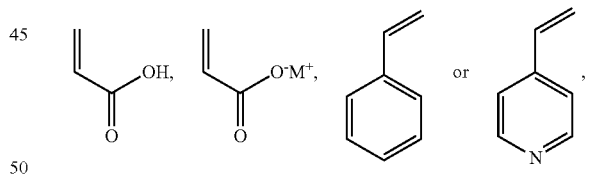

wherein $M^+$ is any suitable counter-cation.

In another embodiment, the polymers of the present disclosure comprise two or more different ethylenically unsaturated monomers as defined above. For example, acrylic acid and styrene; vinyl acetate and styrene; acrylic acid and pentaerythritol allyl ether; acrylic acid and linalool; or acrylated epoxidized soybean oil and linalool, may be used as combinations as the ethylenically unsaturated monomers.

In one embodiment, the monomer comprising at least one unsaturated monomer having an ethylenically unsaturated double or triple bond is present within the anti-microbial polymer at a mole fraction of between 0.00001 to 0.99, or about 0.001 to about 0.90. In one embodiment, the mole fraction is between about 0.5 to about 0.9, or about 0.6 to about 0.9, or about 0.7 to about 0.9, or about 0.7 to about 0.8.

In one embodiment, the monomer comprising a polymerizable cyclic moiety is present as a mole fraction in the overall anti-microbial polymer of about 0.70, or about 0.75, or about 0.77, or about 0.78.

In one embodiment, the monomer comprising a polymerizable cyclic moiety is present within the anti-microbial polymer.

In another embodiment of the disclosure, the anti-microbial polymer comprises a polymer of the formula (I)

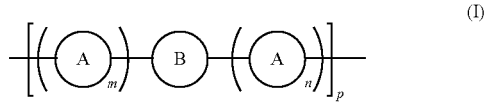

(I)

wherein
the monomer A is the at least one unsaturated monomer having an ethylenically unsaturated double or triple bond as defined in the present disclosure,
the monomer B is the monomer comprising a polymerizable cyclic moiety as defined in the present disclosure,
m, n and p are independently or simultaneously any integers between 1 and 1,000,000.

In one embodiment, m and n are independently or simultaneously integers between 1-10,000, or 1-1,000, or 1-500, or 1-100, or 1-10 or 1-5. In one embodiment, the properties of the anti-microbial polymers of the present disclosure are modulated by controlling the variables p, m and n. For example, the mechanical and anti-microbial properties of the polymer are modulated by varying m and n. In another embodiment, p is any integer between 1-100,000, or 1-50,000, or 1-10,000, or 1-1,000, or 1-500, or 1-100, or 1-10 or 1-5.

In one embodiment, the anti-microbial polymer comprises a polymer of the formula (IA)

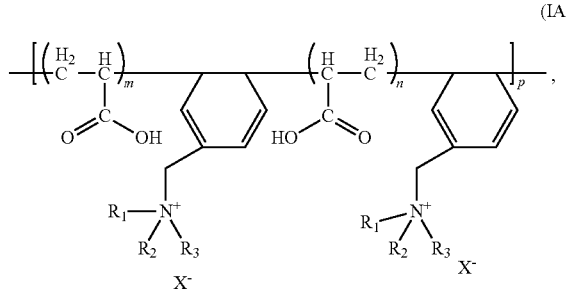

(IA)

wherein $R_1$, $R_2$ and $R_3$ are as defined above,
X is any suitable counteranion, and
m, n and p are independently or simultaneously any integers between 1 and 1,000,000. In one embodiment, $R_1$ and $R_2$ are methyl, and $R_3$ is ($C_8$-$C_{18}$)-alkyl, optionally, $C_8$, $C_{10}$, $C_{12}$, $C_{14}$, $C_{16}$, or $C_{18}$, optionally, $C_{14}$.

In one embodiment, m and n are independently or simultaneously integers between 1-10,000, or 1-1,000, or 1-500, or 1-100, or 1-10 or 1-5. In one embodiment, the properties of the anti-microbial polymers of the present disclosure are modulated by controlling the variables m and n. In another embodiment, p is any integer between 1-100,000, or 1-50,000, or 1-10,000, or 1-1,000, or 1-500, or 1-100, or 1-10 or 1-5.

In one embodiment, the anti-microbial polymer comprises a polymer of the formula (IB)

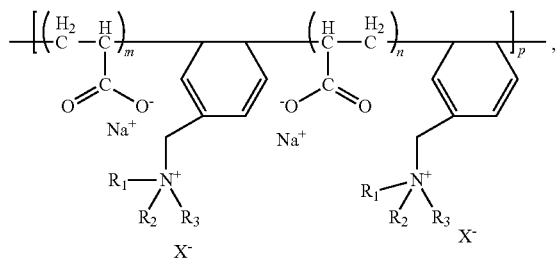

(IB)

wherein $R_1$, $R_2$ and $R_3$ are as defined above,
X is any suitable counteranion, and
m, n and p are independently or simultaneously integers between 1 and 1,000,000. In one embodiment, $R_1$ and $R_2$ are methyl, and $R_3$ is ($C_8$-$C_{18}$)-alkyl, optionally, $C_8$, $C_{10}$, $C_{12}$, $C_{14}$, $C_{16}$, or $C_{18}$, optionally, $C_{14}$.

In one embodiment, m and n are independently or simultaneously integers between 1-10,000, or 1-1,000, or 1-500, or 1-100, or 1-10 or 1-5. In one embodiment, the properties of the anti-microbial polymers of the present disclosure are modulated by controlling the variables m and n. In another embodiment, p is any integer between 1-100,000, or 1-50,000, or 1-10,000, or 1-1,000, or 1-500, or 1-100, or 1-10 or 1-5.

In one embodiment, the anti-microbial polymer comprises a polymer of the formula (IC)

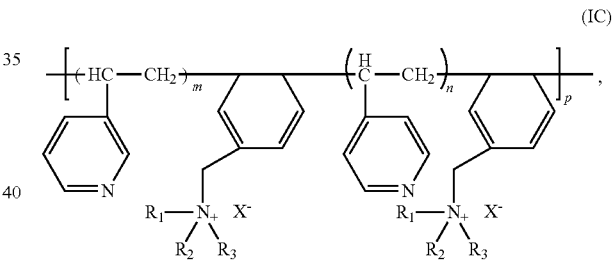

(IC)

wherein $R_1$, $R_2$ and $R_3$ are as defined above,
X is any suitable counteranion, and
m, n and p are independently or simultaneously integers between 1 and 1,000,000. In one embodiment, $R_1$ and $R_2$ are methyl, and $R_3$ is ($C_8$-$C_{18}$)-alkyl, optionally, $C_8$, $C_{10}$, $C_{12}$, $C_{14}$, $C_{16}$, or $C_{18}$, optionally, $C_{14}$.

In one embodiment, m and n are independently or simultaneously integers between 1-10,000, or 1-1,000, or 1-500, or 1-100, or 1-10 or 1-5. In one embodiment, the properties of the anti-microbial polymers of the present disclosure are modulated by controlling the variables m and n. In another embodiment, p is any integer between 1-100,000, or 1-50,000, or 1-10,000, or 1-1,000, or 1-500, or 1-100, or 1-10 or 1-5.

In another embodiment of the disclosure, the anti-microbial polymers are conjugated to cellulose or a cellulose derivative either binding the cellulose sheets to each other or made in situ with cellulose powder or cellulose waste.

In another embodiment of the disclosure, the monomers which form the anti-microbial polymers of the present disclosure are prepared in the presence of an ionic liquid. In one embodiment, the ionic liquid is incorporated into the structure of the anti-microbial polymer. In one embodiment, the ionic liquid is a phosphonium ionic salt. In another embodiment, the phosphonium ion salt has the structure

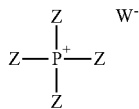

wherein
each Z is independently or simultaneously $(C_1\text{-}C_{20})$-alkyl group or alkyl group with a single or double bond and W is any suitable anionic ligand. The ionic liquid serves as solvent, co-solvent, monomer and also contributes to anti-microbial properties.

In another embodiment, each Z is independently or simultaneously methyl, ethyl, propyl, butyl, isobutyl, pentyl, hexyl, heptyl, octyl, nonyl, decyl, undecyl, dodecyl, tridecyl, tetradecyl, pentadecyl or hexadecyl.

In another embodiment, W is chloride, bromide, decanoate, (bis 2,4,4-trimethylpentyl)phosphinate, dicyanamide, tosylate, methylsulfate, bistriflamide, hexafluorophosphate, tetrafluoroborate, diethylphosphate or dedecylsulfonate.

In another embodiment of the disclosure, the at least one unsaturated monomer having an ethylenically unsaturated double or triple bond comprises a polyol or thiol having an ethylenically unsaturated moiety, such as a polyalkene or polyalkyne polyol, such as polybutadiene diol and triol, polyisobutylene diols and triols, polybutylene oxide diols and triols, 2-butyne-1,4-diol, aromatic polyols, such as benzene-diol, benzene-1,2-dithiol. The anti-microbial polymers prepared from such diols results in a polymer having pendant hydroxyl groups. In one embodiment, such polymers are reacted with isocyanates such as an aromatic di-isocyanate (toluene diisocyanate, methylene diphenyl diisocyanate) to form modified polyurethane polymers which have anti-microbial properties. Such anti-microbial polyurethane derivatives are useful for preparing polyurethane articles having anti-microbial properties, such as foam seating, medical devices, catheters, coatings, adhesives, sealants and elastomers.

(IV) Processes for Preparation of the Disclosure

The polymers of the present disclosure are prepared using techniques known to those skilled in the art.

In one embodiment, the polymers of the present disclosure are prepared using techniques as described in US publication no. 2012-0049101. In one embodiment, the anti-microbial polymers of the present disclosure are prepared in at least 95% yield, or about 98% yield, or about 99% yield, or 100% yield. In one embodiment, there are no by-products from the polymerization reaction to prepare the polymers of the present disclosure. In one embodiment, all of the reactants, including the monomers comprising a polymerizable cyclic moiety and the unsaturated monomers having an ethylenically unsaturated double or triple bond, and optionally the radical initiators and ionic liquids, form part of the anti-microbial polymers resulting in no waste products.

(IV) Uses of the Anti-Microbial Polymers

The anti-microbial polymers of the present disclosure are useful to prevent or inhibit the growth of microbes, such as bacteria, fungi, viruses and protozoa.

In one embodiment, the polymers are useful for the preparation of devices comprised solely of the polymer itself, or the polymer can form a coating on a device to impart anti-microbial properties.

In one embodiment, the present disclosure includes an anti-microbial medical device comprising,
  i) a medical device; and
  ii) an anti-microbial polymer as defined in the disclosure coated on the device.

In one embodiment, the device is selected from a catheter, stent, wound dressing, contraceptive device, surgical implant, orthopedic implant, dental implant, contact lens and replacement joint.

In another embodiment, there is also included an anti-microbial packaging material comprising,
  i) a packaging material,
  ii) an anti-microbial polymer as defined in the disclosure coated on the material.

In one embodiment, the packaging material is a food packaging material that is optionally used to store perishable food In another embodiment, the anti-microbial polymer of the disclosure is conjugated with cellulose or a cellulose derivative, resulting in a pulp and paper product having anti-microbial properties, wherein the pulp and paper product is, for example, tissue paper, paper towel or toilet paper. Alternatively, in one embodiment, the anti-microbial polymer of the disclosure is used as a binder or glue, such as a laminating glue, in pulp and paper products to bind the pulp and paper components together. For example, the anti-microbial polymers of the present disclosure are used as a laminating glue to bind plies of tissue paper, toilet paper, and/or paper towel. In another embodiment, the anti-microbial polymer is coated on the pulp and paper product.

In another embodiment, the anti-microbial polymer of the present disclosure is coated on, or conjugated to, fabrics or other materials to produce articles of clothing having anti-microbial properties.

In another embodiment, the anti-microbial polymers of the present disclosure are formed, for example by extrusion processing, into specific objects or devices which therefore have inherent anti-microbial properties. For example, the polymers of the present disclosure are formed into a medical device such as a stent, a construction material or consumer product. For example, the polymers may be formed into a bathroom or kitchen object having anti-microbial properties such as a sink, tap, tiles, countertop, storage cabinets, flooring such as vinyl flooring.

In another embodiment, the anti-microbial polymers of the disclosure may be formed into a polymer wood composite material (for example, for decking), into parts of a marine vessel or ship, fishnets or other marine aquaculture equipment. The polymers may also be formed into a textile, or form part of a textile, such as bedding, drapes, surgical masks, surgical gowns, etc.

In one embodiment, the anti-microbial polymers may be simply sprayed on an object to impart anti-microbial properties to the object. Alternatively, the polymers may be formed in situ with the object.

In another embodiment, the anti-microbial polymers of the present disclosure are also used in pharmaceutical and cosmetic formulations and compositions, such as in intravenous solutions, topical formulations, tablet and capsule formulations, to impart anti-microbial properties to those formulations, especially against gram positive bacteria, gram negative bacteria, yeast and filamentous fungi. In one embodiment, the cosmetic formulation is an anti-microbial soap, a personal care product, cosmetics, hand sanitizers, and anti-microbial hydrogels.

In another embodiment, the anti-microbial polymers of the present disclosure are formulated into cleaning solutions, as well as sanitizers.

The operation of the disclosure is illustrated by the following representative examples. As is apparent to those skilled in the art, many of the details of the examples may be changed while still practicing the disclosure described herein.

(IV) Examples

Figure 2:
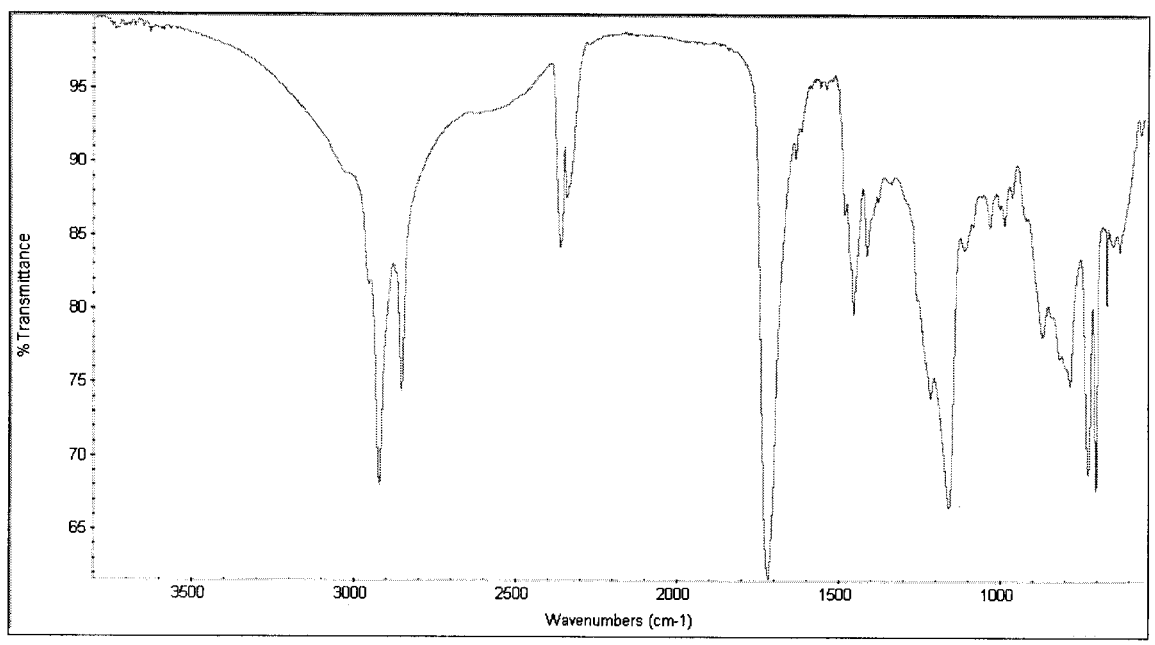
FIG. 2 is an FTIR spectrum of a PAA-BZ polymer product in an embodiment of the disclosure.
Figure 3:
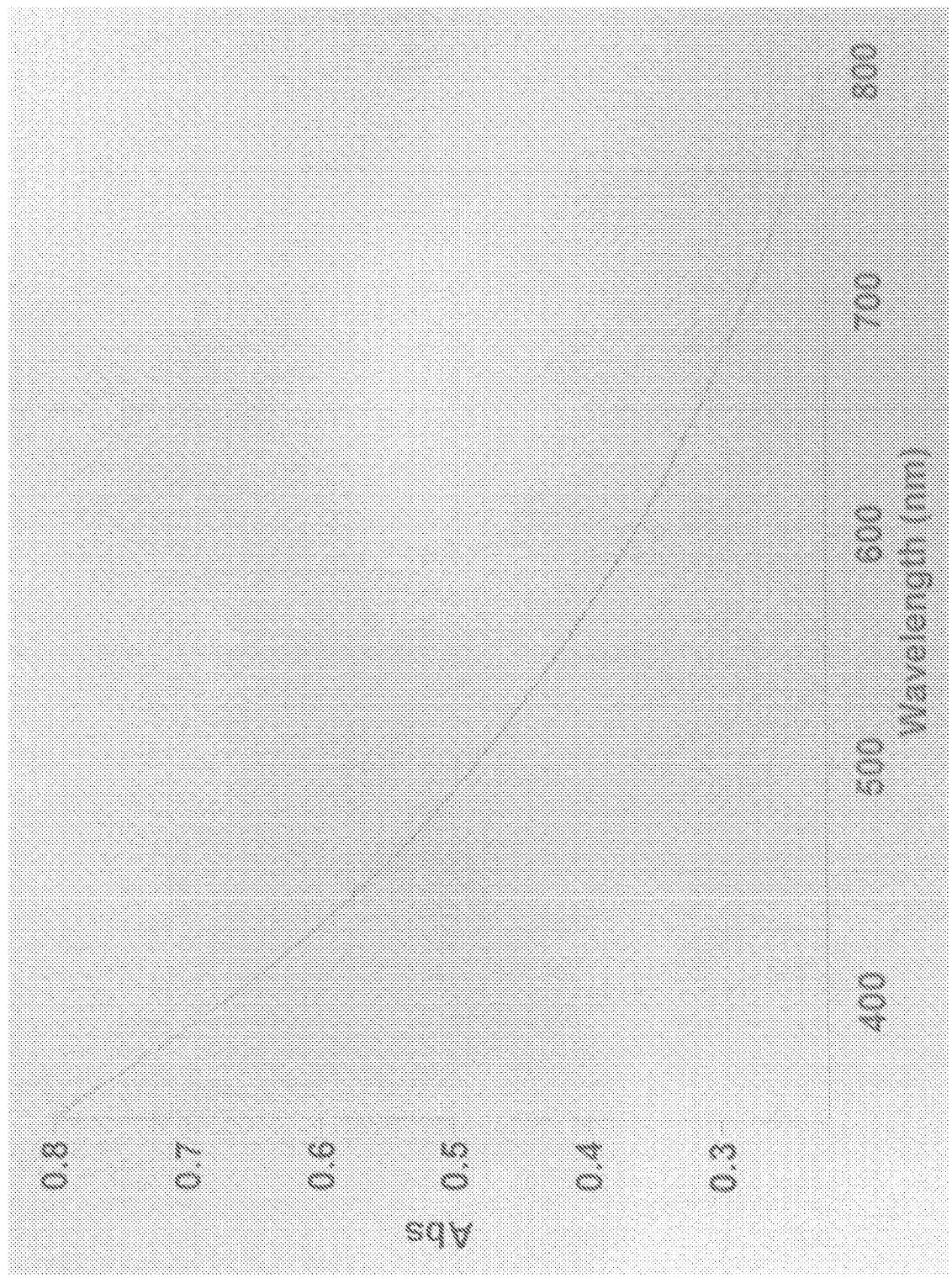
FIG. 3 is an UV-Vis spectrum of a PAA-BZ polymer product in an embodiment of the disclosure.

Example 1—Preparation of Anti-Microbial Polymer Using Acrylic Acid and Benzyldimethyltetradecylammonium Chloride In a three neck flask, 8 ml of Acrylic Acid (PAA) and 12 g of Benzyldimethyltetradecylammonium chloride (Bz) were mixed under magnetic stirring and gentle heating (less than 60° C.) until the Bz was completely dissolved in AA. The mixture was then heated to 60° C. and the heat was turned off, but magnetic stirring continued. 0.5 g of the initiator 2,2'-Azobis(2-methylpropionitrile) (AIBN) was immediately added to the reaction mixture and the polymerization was initiated. The resulting reaction is schematically depicted below in Scheme I below, showing the reaction and product of the PAA-BZ polymerization, where m,n and p may be equal or an integer between 1 and 1,000,000 and R represents a long alkyl chain, in this particular reaction R is a C14H29 alkyl chain. As the reaction is exothermic, the temperature of the mixture continued to rise until the reaction was complete and only solid polymer remains. Alternatively the reaction can also be performed wherein the AIBN is added to the initial mixture of BZ and AA, and once BZ and AIBN are completely dissolved into the PAA, the solution can be heated to 60° C. to initiate the polymerization reaction. The resulting polymer was characterized by nuclear magnetic resonance spectroscopy (NMR) (FIG. 1), Fourier transform infra-red spectroscopy (FTIR) (FIG. 2.) and ultra-violet-visible spectroscopy (UV/Vis) (FIG. 3).

Scheme 1

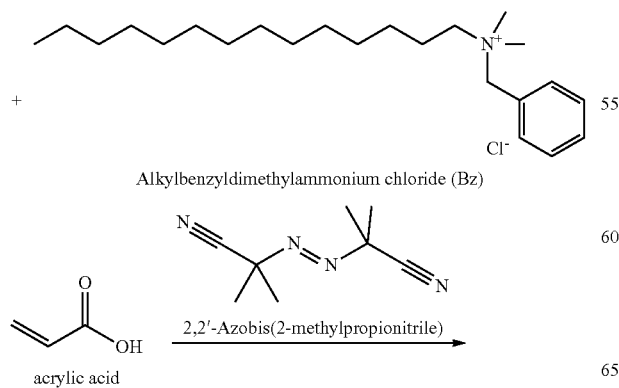

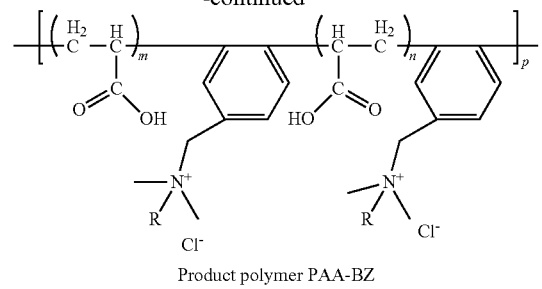

Product polymer PAA-BZ

Figure 4:
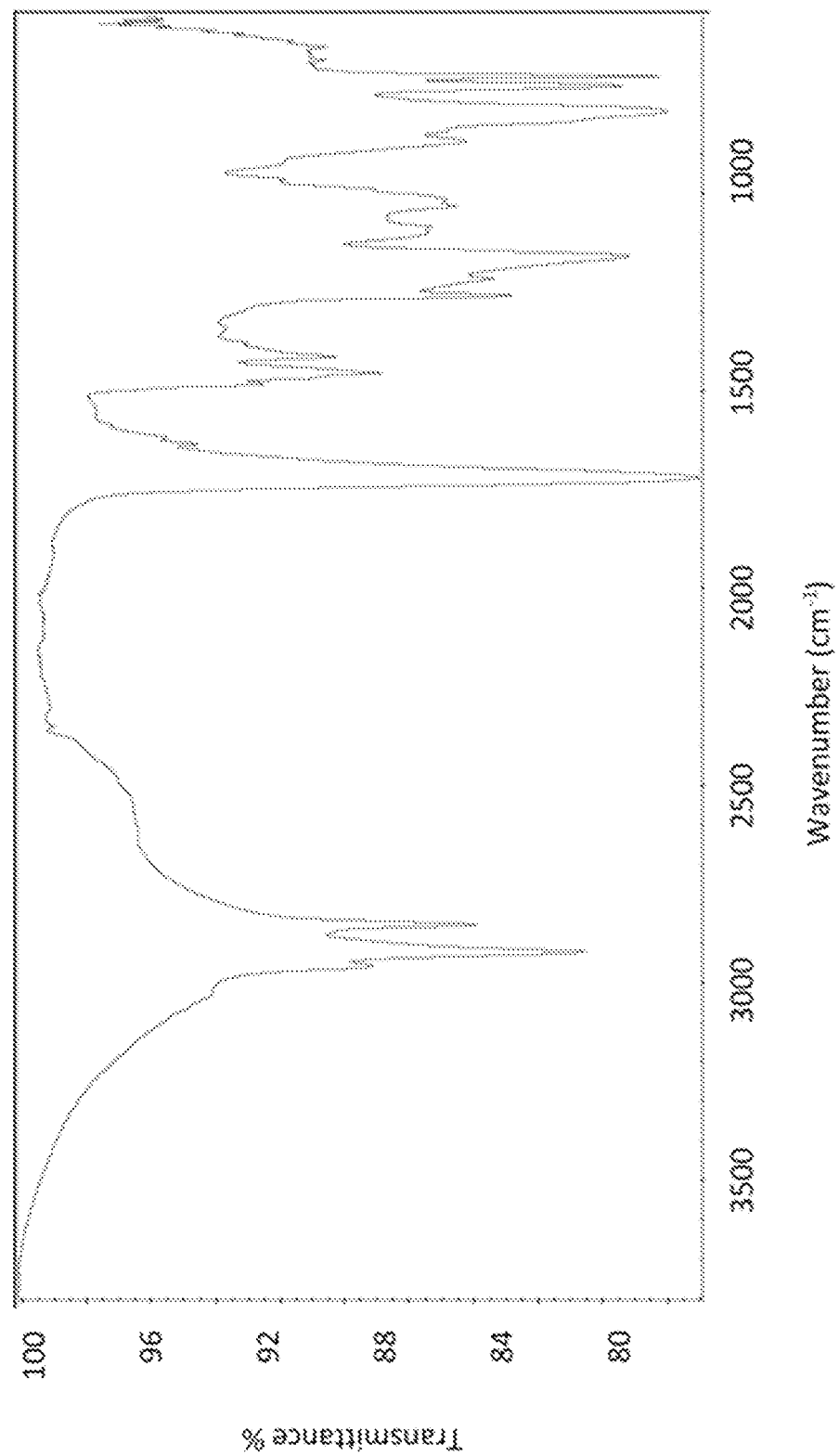
FIG. 4 is an FTIR spectrum of a PAA-BZ-CELL polymer product in an embodiment of the disclosure.
Figure 5:
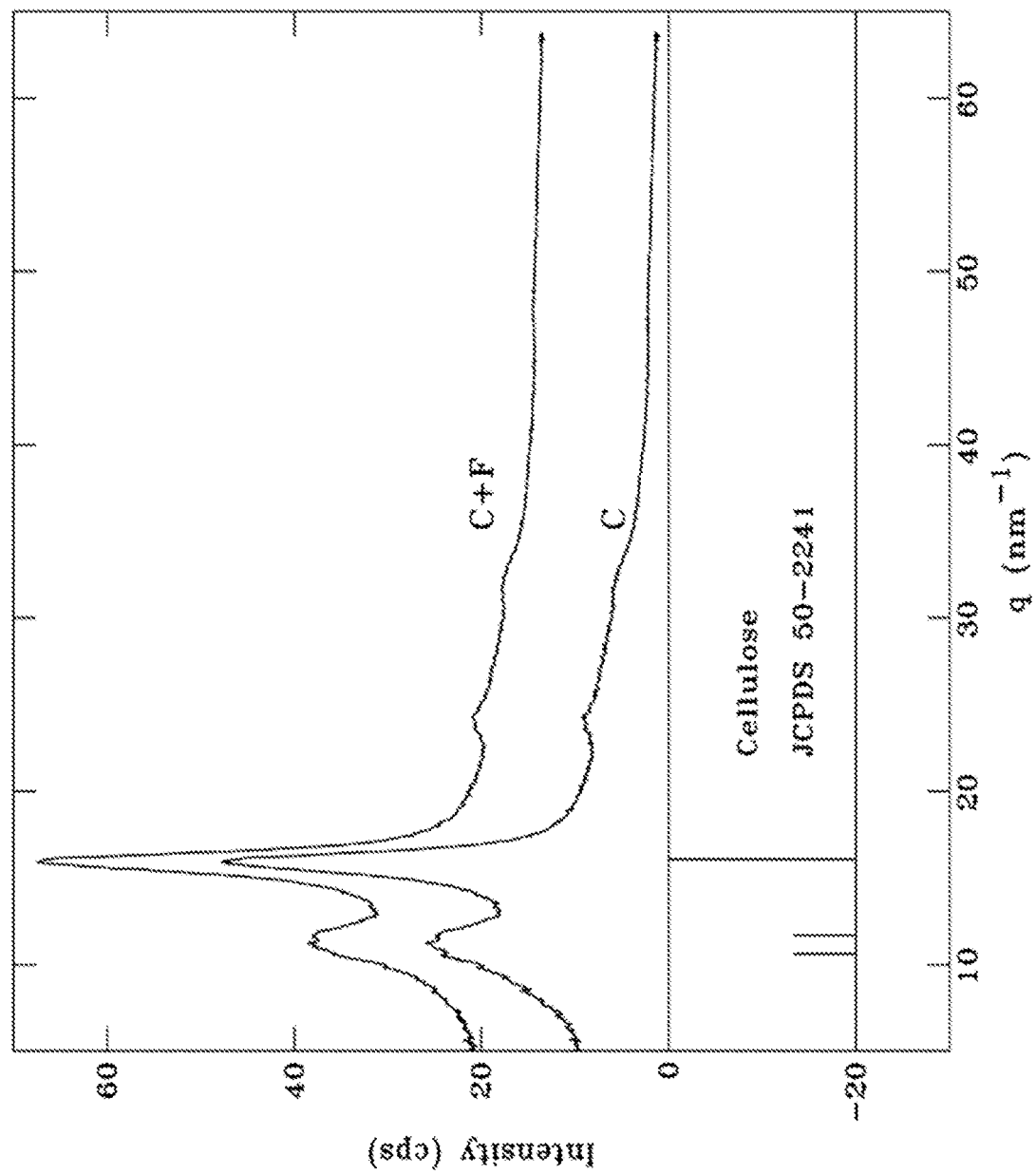
FIG. 5 is an X-ray Diffraction (XRD) spectrum of a PAA-BZ-CELL polymer, along with the reference peaks by the Joint Committee on Powder Diffraction Standards (JCPDS) in an embodiment of the disclosure.

Example 2—Preparation of Anti-Microbial Polymer Using Acrylic Acid and Benzyldimethyltetradecylammonium Chloride and Cellulose In a three neck flask, 8 ml of Acrylic Acid (PAA) and 12 g of Benzyldimethyltetradecylammonium chloride (BZ) and 0.03 g cellulose (CELL) were mixed under magnetic stirring and gentle heating (less than 60° C.) until the BZ was completely dissolved in AA. The mixture was then heated to 60° C. and the heat was turned off, but magnetic stirring continues. 0.5 g of the initiator 2,2'-Azobis(2-methylpropionitrile) (AIBN) was immediately added to the reaction mixture and the polymerization was initiated. As the reaction is exothermic, the temperature of the mixture continued to rise until the reaction was complete and only solid polymer remains. Alternatively the reaction can also be performed wherein the AIBN is added to the initial mixture of CELL, BZ and PAA, and once BZ and AIBN are completely dissolved into the AA, the solution can be heated to 60° C. to initiate the polymerization reaction. Alternatively polymerization can be initiated using hydrogen peroxide ($H_2O_2$) as an initiator. The polymer of PAA-BZ-CELL was characterized by FTIR spectroscopy (FIG. 4), and X-ray Diffraction (XRD) (FIG. 5) spectrum confirming the presence of cellulose within the polymeric material. A proposed structure speculating the interactions between the three components (PAA,BZ and CELL) of the materials is presented in Scheme II, as shown below, showing the structure of the purported interactions between the three components (PAA,BZ and CELL) of the material PAA-BZ-CELL, where A- is any counterion for the quaternary ammonium compound. In this instance A- is a chlorine atom Cl—, and m,n and p,q may be equal or an integer between 1 and 1,000,000.

Scheme II

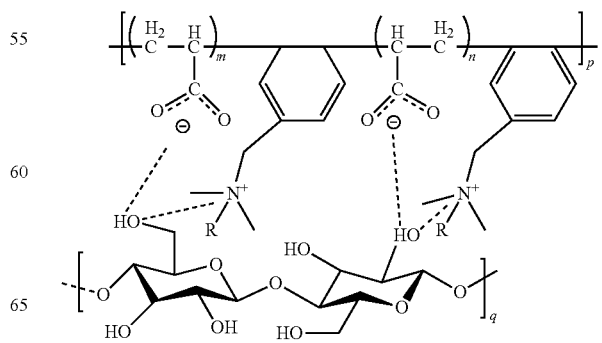

-continued

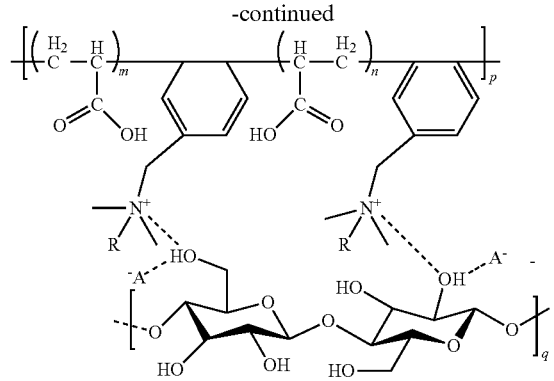

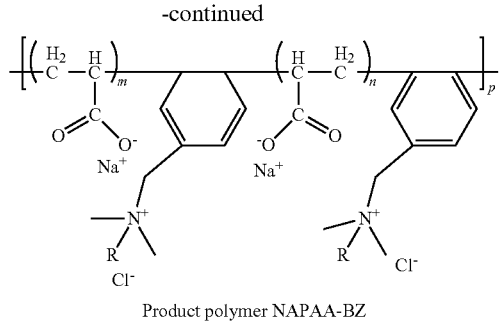

Product polymer NAPAA-BZ

Alternatively, varying the ratios of cellulose to acrylic acid while not varying the amount of BZ added were also examined using the synthesis scheme described above where water is used as a reaction solvent. These variations in the reactant concentrations and the product yield are presented below in Tables 1 and 2.

Figure 6:
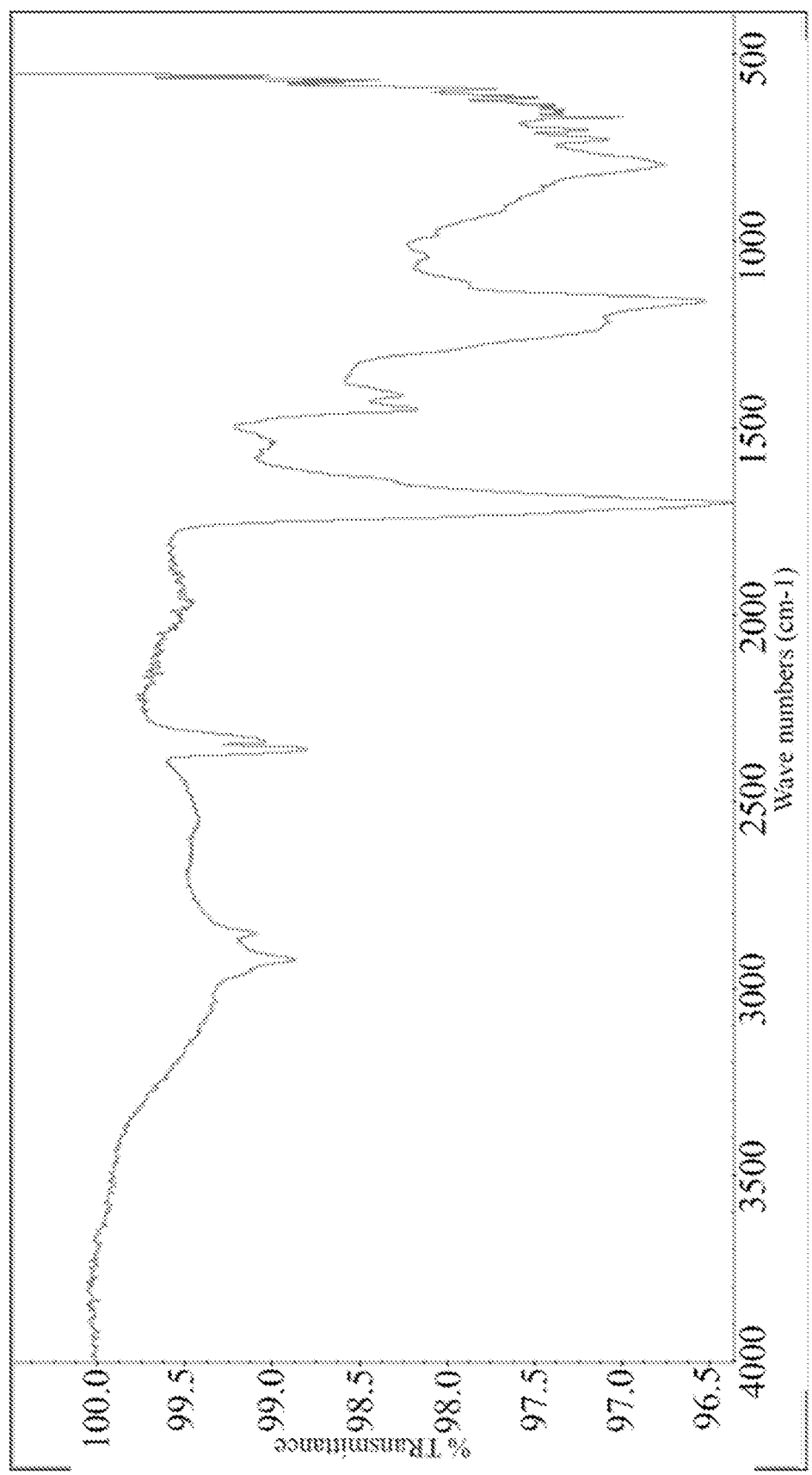
FIG. 6 is an FTIR spectrum of a NAPPA-BZ polymer product in an embodiment of the disclosure.
Figure 7:
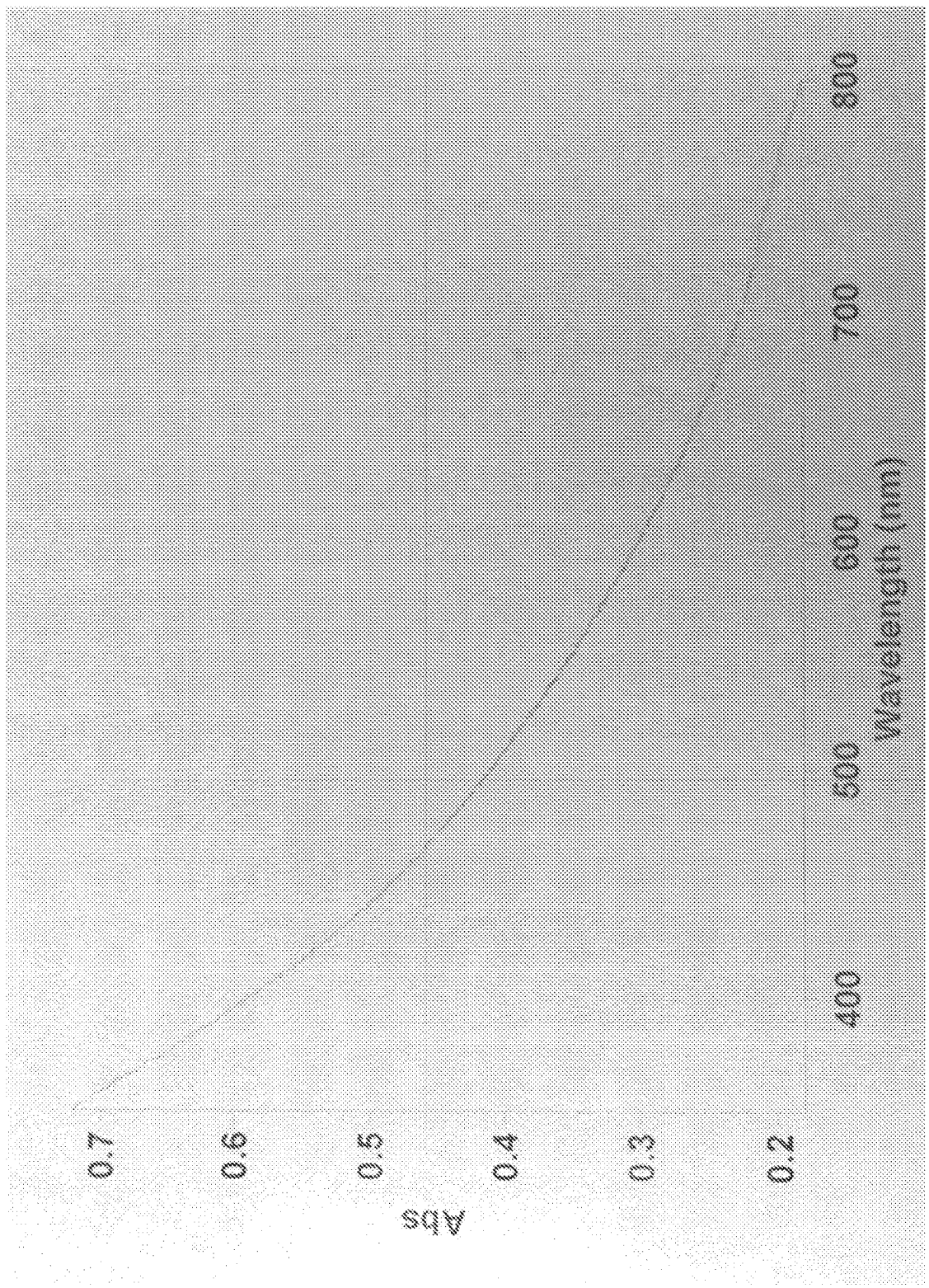
FIG. 7 is an UV-Vis spectrum of a NAPAA-BZ polymer product dissolved in Dimethylformamide (DMF) in an embodiment of the disclosure.

Example 3—Preparation of Anti-Microbial Polymer Composed of Sodium Acrylate and Benzyldimethyltetradecylammonium Chloride PAA-BZ as previously synthesized was dissolved in water at a high concentration (0.22 g/ml). A solution of 6M sodium hydroxide (NaOH) was then slowly added drop wise into the dissolved solution of PAA-BZ forming a solid polymeric precipitate, which is the Sodium polyacrylate form (NAPAA) of the PAA-BZ polymer to form NAPAA-BZ. This precipitate was characterized by FTIR (FIG. 6). The polymer was then dissolved in Dimethylformamide (DMF) and a UV/Vis spectrum of the sample was taken (FIG. 7). The proposed reaction scheme of the product is similar to that of PAA-BZ with the final product being depicted below in Scheme III, showing the reaction product of the PAA-BZ+ NaOH to form NAPAA-BZ, where m,n and p may be equal or an integer between 1 and 1,000,000 and R represents a long alkyl chain, in this particular reaction R is a C14H29 alkyl chain. This salt form of the product can also be made using other counterions on the acrylic acid such as lithium, potassium and ammonium cations, based upon the choice of base used to react with the PAA-BZ polymer.

Figure 8:
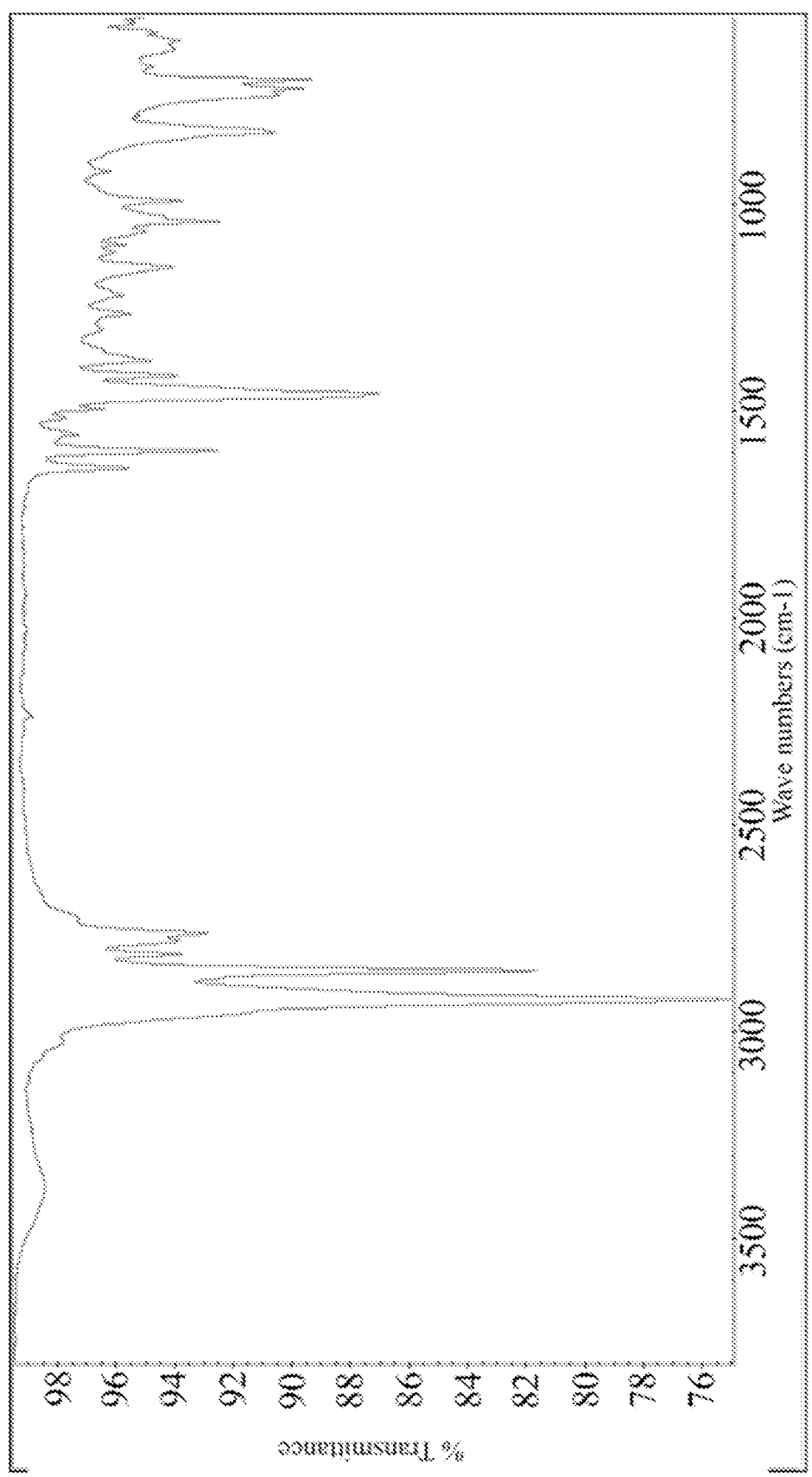
FIG. 8 is an FTIR spectrum of a PVP-BZ (High) polymer product in an embodiment of the disclosure.

Example 4—Preparation of Anti-Microbial Polymer Using Vinyl-Pyridine and Benzyldimethyltetradecylammonium Chloride and Cellulose In a three neck flask, 8 ml of 4-Vinylpyridine (PVP) and 8 g of Benzyldimethyltetradecylammonium chloride (BZ) and 0.4 g cellulose (CELL) were mixed under magnetic stirring and gentle heating (less than 60° C.) until the BZ was completely dissolved in PVP. The mixture was then heated to 65° C. and the heat was turned off, but magnetic stirring continues. 1.2 g of the initiator 2,2'-Azobis(2-methylpropionitrile) (AIBN) was immediately added to the reaction mixture and the polymerization was initiated. As the reaction was exothermic, the temperature of the mixture continues to rise until the reaction is complete and only solid polymer remains. Alternatively the reaction can also be performed wherein the AIBN is added to the initial mixture of CELL, BZ and PVP, and once BZ and AIBN are completely dissolved into the PVP, the solution can be heated to 65° C. to initiate the polymerization reaction. A proposed structure speculating the interactions between the three components (PAA,BZ and CELL) of the materials is presented in Scheme 4, showing purported interactions between the three components (PAA,BZ and CELL) of the material PAA-BZ-CELL, where A- is any counterion for the quaternary ammonium compound. In this instance A- is a chlorine atom Cl—, and m,n and p,q may be equal or an integer between 1 and 1,000,000 An FTIR spectrum of the PVP-BZ (High) sample is shown in FIG. 8.

Scheme III

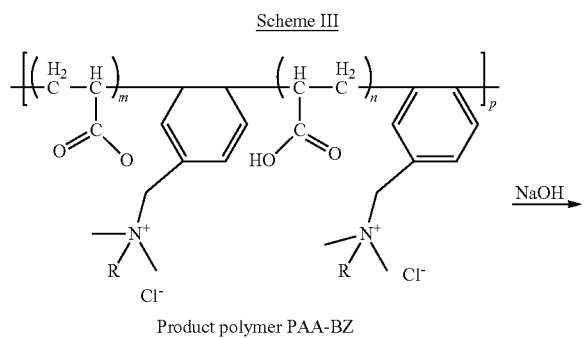

Product polymer PAA-BZ

Scheme 4

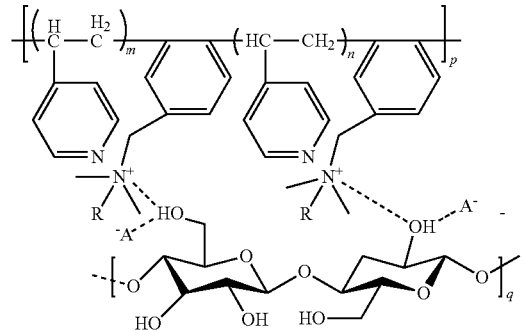

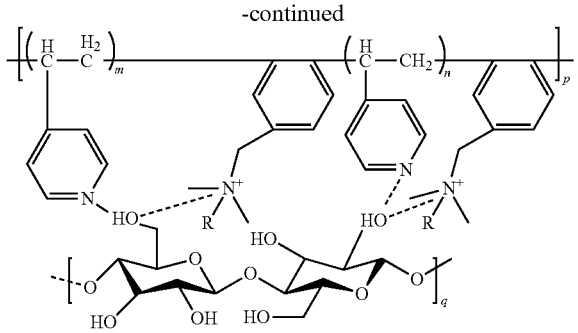

Figure 9:
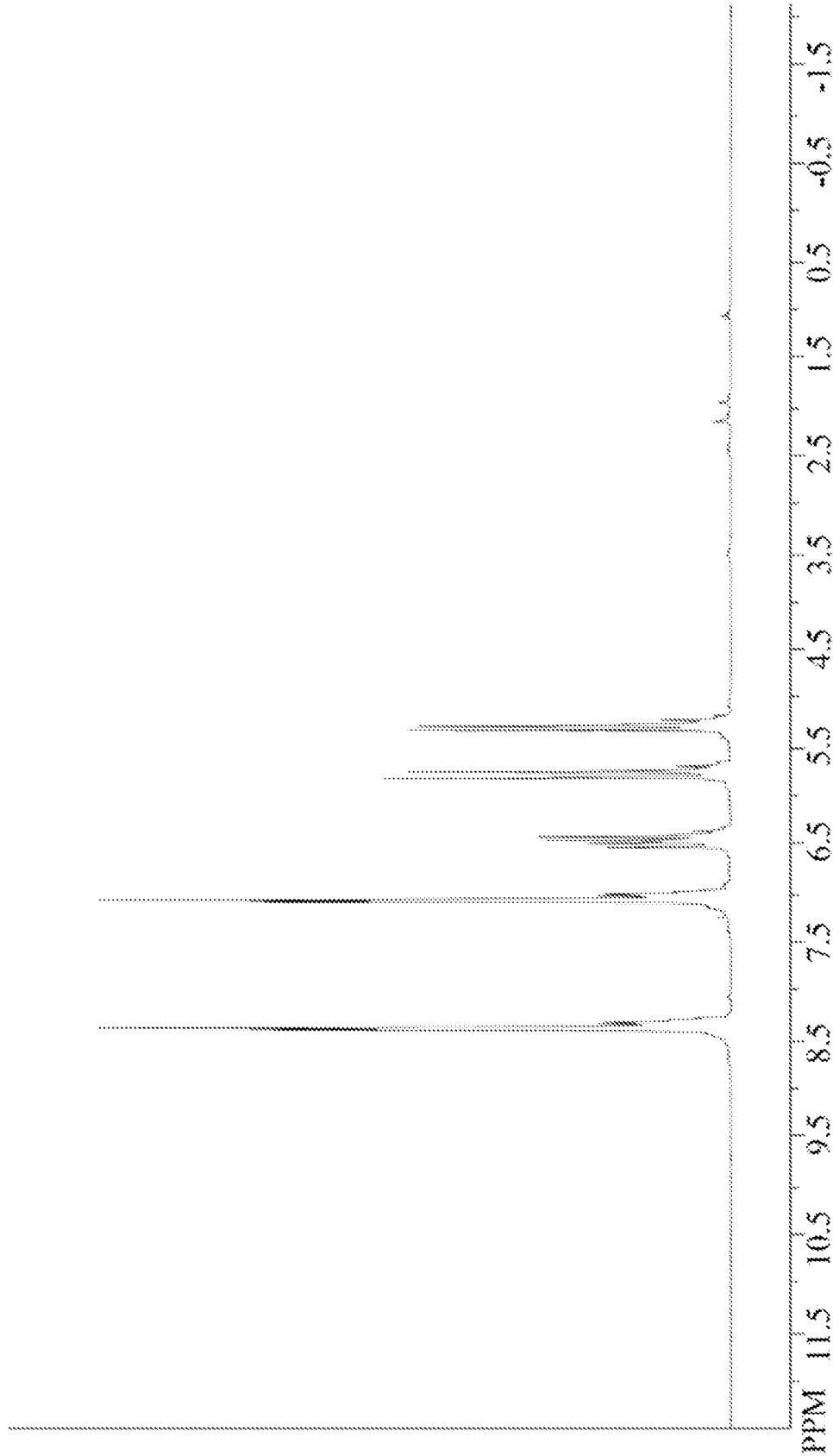
FIG. 9 is an NMR spectrum of a PVP-BZ (low) polymer product in an embodiment of the disclosure.
Figure 10:
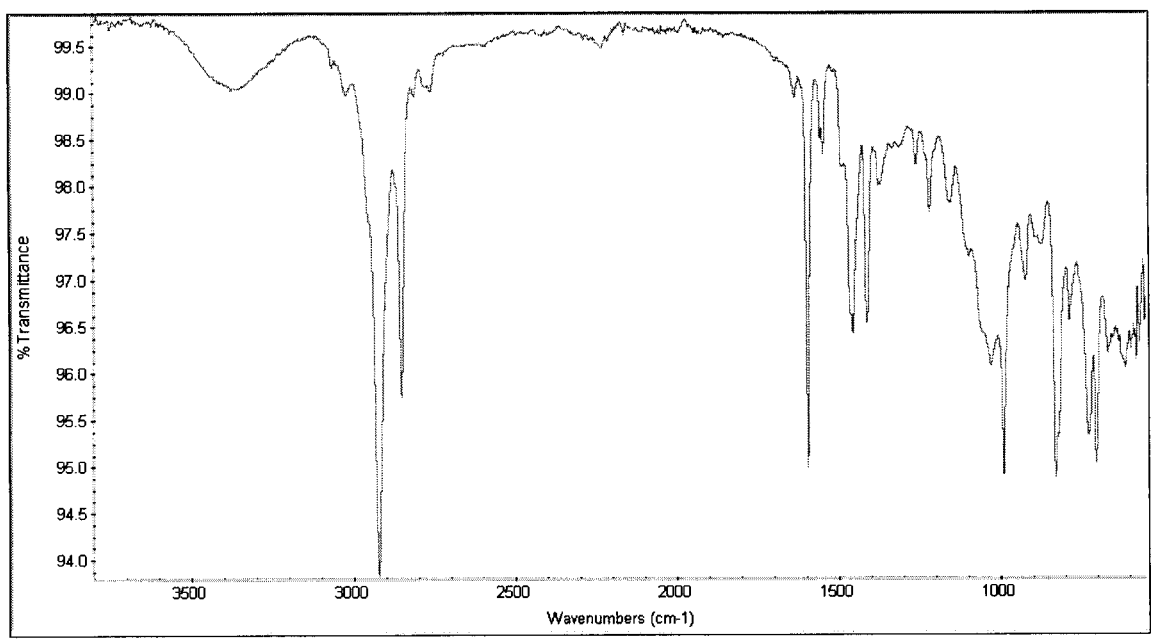
FIG. 10 is an FTIR spectrum of a PVP-BZ (low) polymer product in an embodiment of the disclosure.
Figure 11:
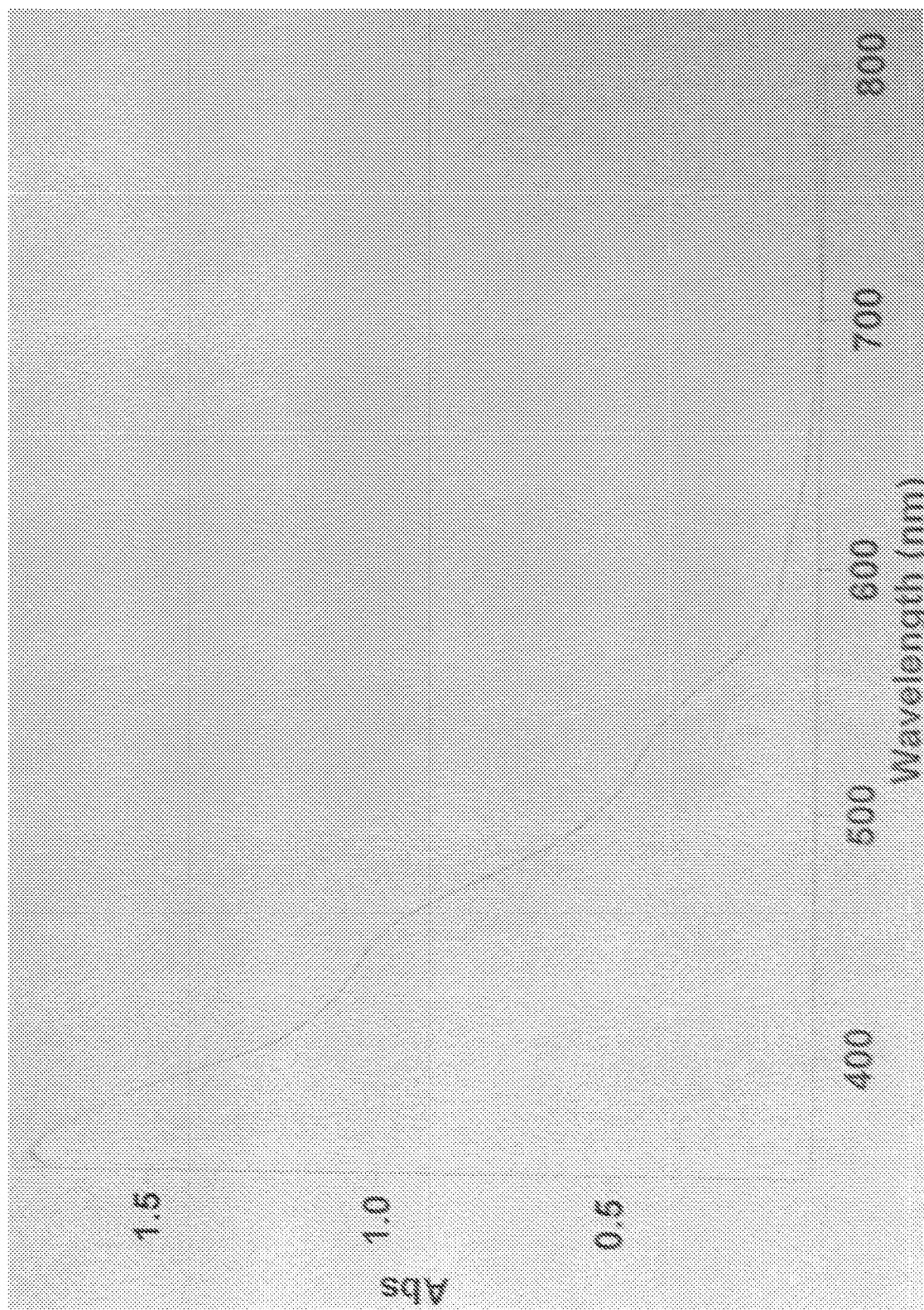
FIG. 11 is an UV-Vis spectrum of a PVP-BZ (low) polymer product in an embodiment of the disclosure.

Example 5—Preparation of Anti-Microbial Polymer Using Vinyl-Pyridine and Benzyldimethyltetradecylammonium Chloride and Cellulose In a three neck flask, 8 ml of 4-Vinylpyridine (PVP) and 2 g of Benzyldimethyltetradecylammonium chloride (BZ) and 0.4 g cellulose (CELL) were mixed under magnetic stirring and gentle heating (less than 60° C.) until the BZ was completely dissolved in PVP. The mixture was then heated to 65° C. and the heat was turned off, but magnetic stirring continues. 1.2 g of the initiator 2,2'-Azobis(2-methylpropionitrile) (AIBN was is immediately added to the reaction mixture and the polymerization was initiated. As the reaction was exothermic, the temperature of the mixture continued to rise until the reaction was complete and only solid polymer remains. Alternatively the reaction can also be performed wherein the AIBN is added to the initial mixture of CELL, BZ and PVP, and once BZ and AIBN are completely dissolved into the PVP, the solution can be heated to 65° C. to initiate the polymerization reaction. The resulting reaction is schematically similar to that depicted in scheme IV. An NMR spectrum of the PVP-BZ polymer is presented in FIG. 9, an FTIR spectrum of the PVP-BZ (low) sample is shown in FIG. 10 and a UV-Vis spectrum of the polymer is shown in FIG. 11.

Figure 12:
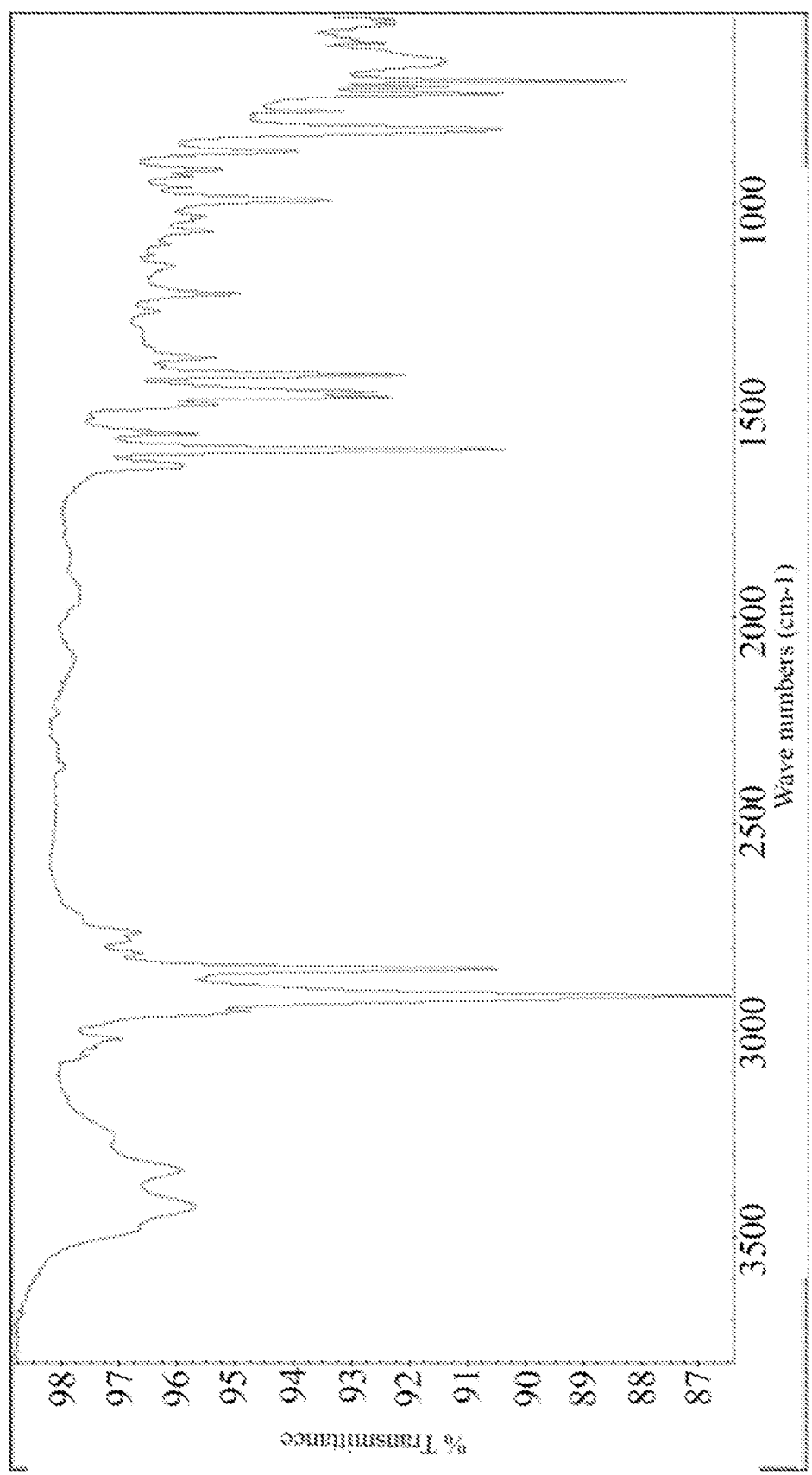
FIG. 12 is an FTIR spectrum of a PVP-BZ (Med) polymer product in an embodiment of the disclosure.
Figure 13:
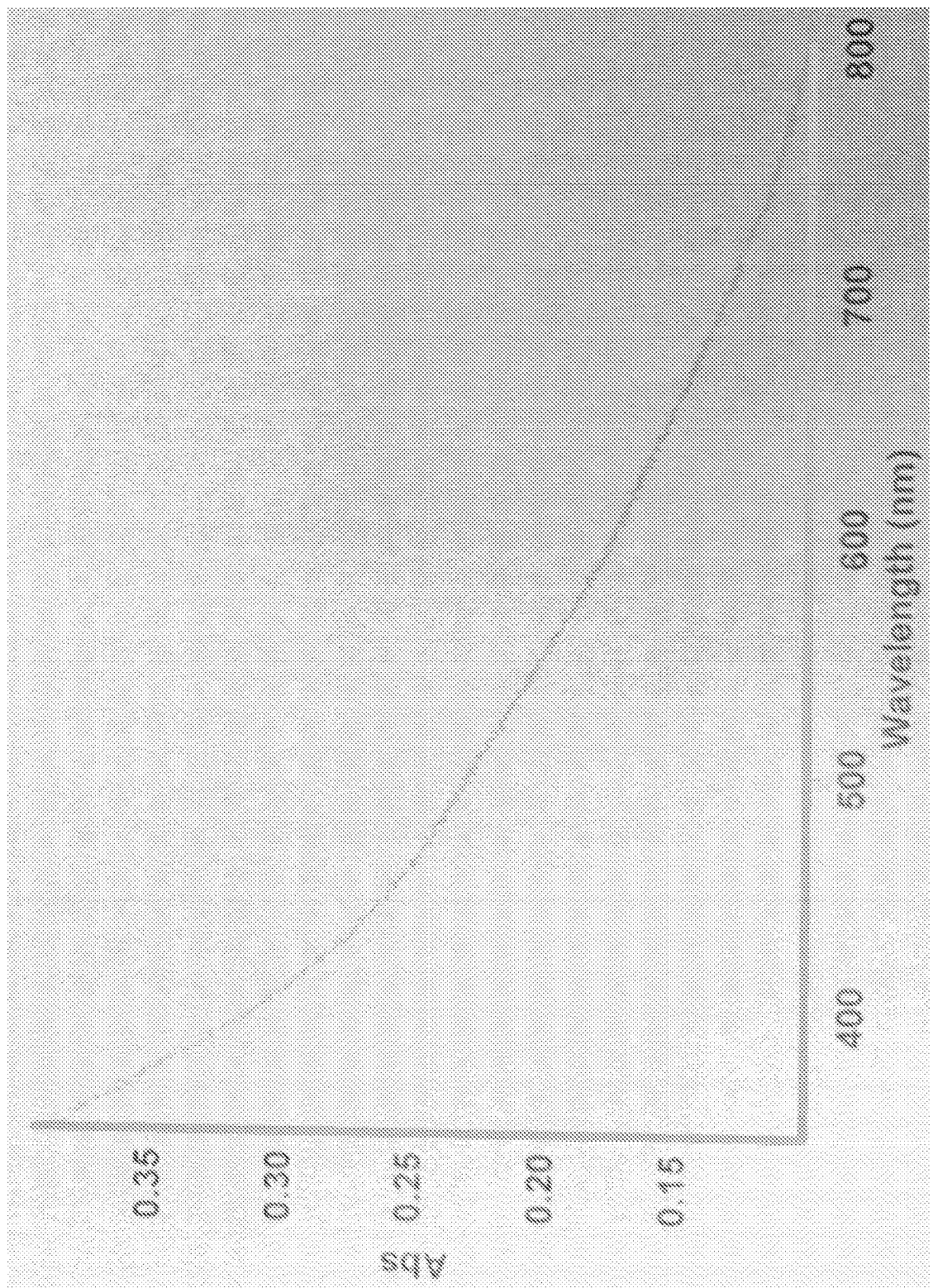
FIG. 13 is an UV-Vis spectrum of a PVP-BZ (Med) polymer product in an embodiment of the disclosure.

Example 6—Preparation of Anti-Microbial Polymer Using Vinyl-Pyridine and Benzyldimethyltetradecylammonium Chloride and Cellulose In a three neck flask, 2 ml of 4-Vinylpyridine (PVP) and 1 g of Benzyldimethyltetradecylammonium chloride (BZ) and were mixed under magnetic stirring and gentle heating (less than 60° C.) until the BZ was completely dissolved in PVP. The mixture was then heated to 65° C. and the heat was turned off, but magnetic stirring continues. 0.3 g of the initiator 2,2'-Azobis(2-methylpropionitrile) (AIBN) was immediately added to the reaction mixture and the polymerization was initiated. As the reaction was exothermic, the temperature of the mixture continued to rise until the reaction was complete and only solid polymer remains. Alternatively the reaction can also be performed wherein the AIBN is added to the initial mixture of CELL, BZ and PVP, and once BZ and AIBN are completely dissolved into the PVP, the solution can be heated to 65° C. to initiate the polymerization reaction. The resulting reaction is schematically shown in Scheme 5, showing reaction and products of the PVP-BZ (Med) polymerization, where m,n and p may be equal or an integer between 1 and 1,000,000 and R represents a long alkyl chain, in this particular reaction R is a C14H29 alkyl chain. An FTIR spectrum of the PVP-BZ (Med) sample is shown in FIG. 12 and a UV-Vis spectrum of the polymer is shown in FIG. 13.

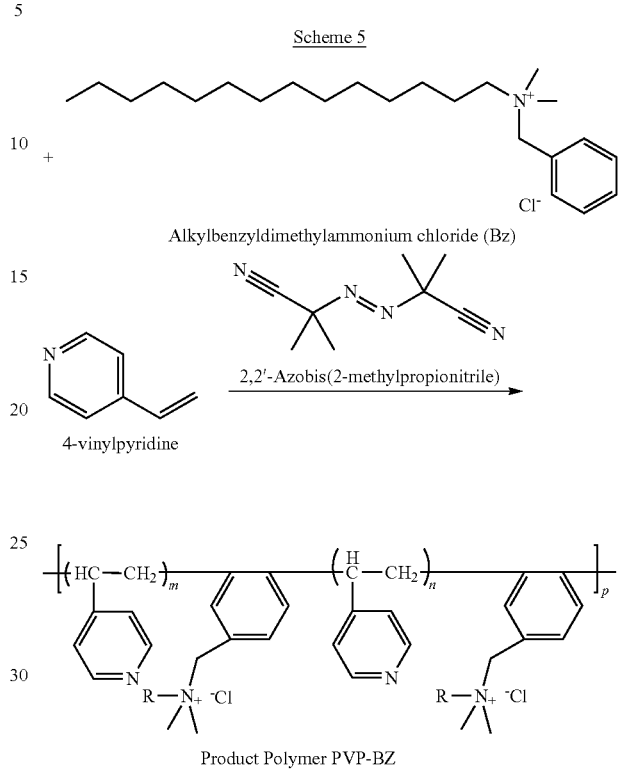

Figure 14:
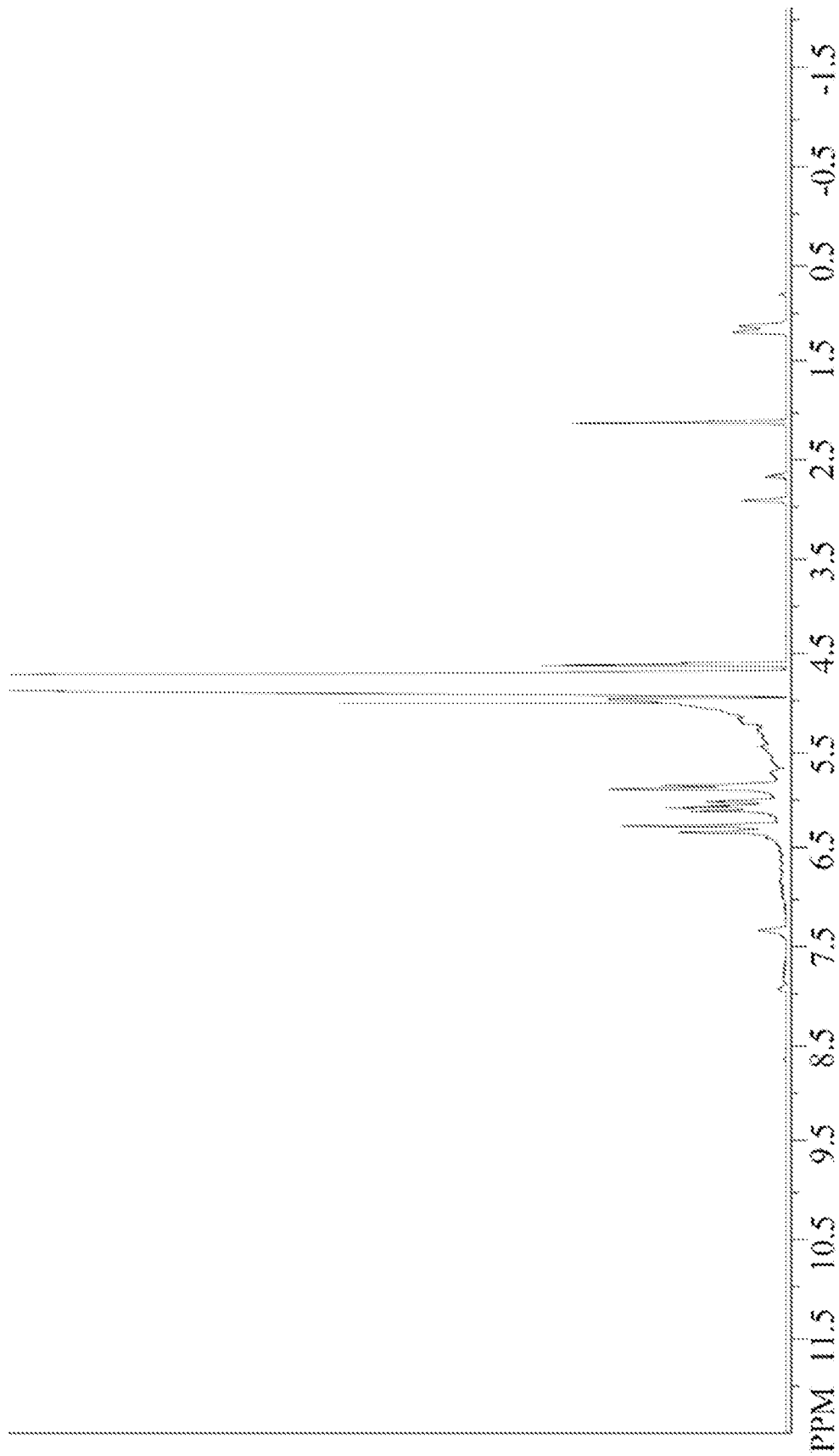
FIG. 14 is an NMR spectrum of a PAA-PVP-BZ polymer product in an embodiment of the disclosure.

Example 7—Preparation of Anti-Microbial Polymer Using Acrylic Acid, Vinyl Pyridine and Benzyldimethyltetradecylammonium Chloride In a three neck flask, 9 ml of Acrylic Acid (PAA) and 1 ml of 4-Vinylpyridine (PVP) and 2 g of Benzyldimethyltetradecylammonium chloride (BZ) and were mixed under magnetic stirring and gentle heating (less than 60° C.) until the BZ was completely dissolved in PAA and PVP mixture. The mixture was then heated to 80° C. and the heat is turned off, but magnetic stirring continues. 0.6 g of the initiator 2,2'-Azobis(2-methylpropionitrile) (AIBN) was immediately added to the reaction mixture and the polymerization was initiated. As the reaction is exothermic, the temperature of the mixture continued to rise until the reaction was complete and only solid polymer remains. Alternatively the reaction can also be performed wherein the AIBN is added to the initial mixture of CELL, BZ and PVP, and once BZ and AIBN are completely dissolved into the PVP, the solution can be heated to 80° C. to initiate the polymerization reaction. Some of the combinations in which the PAA, PVP and BZ react to form random polymeric chains or crosslinked products as reaction products in Scheme 6, in which m,n,o,p and q can be equal to each other or integers from 1 to 1,000,000. A is the counter ion in this instance it is $Cl^-$, and X is any substitution on the benzyl ring and in this instance is an H, and B, C, C' and B' are monomers of the copolymer, in this instance they optionally represent PVP or AA monomers, oligomers or polymers. An NMR spectrum of the PAA-PVP-BZ sample is shown in FIG. 14.

Scheme 6

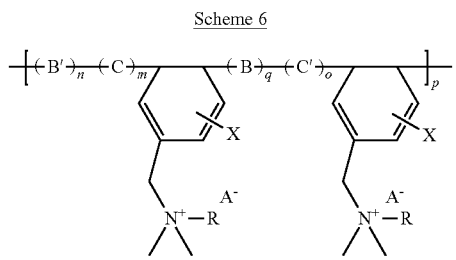

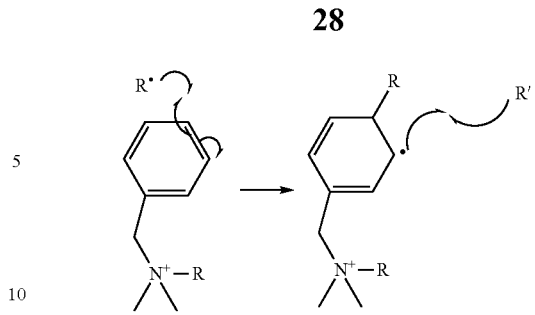

Figure 15:
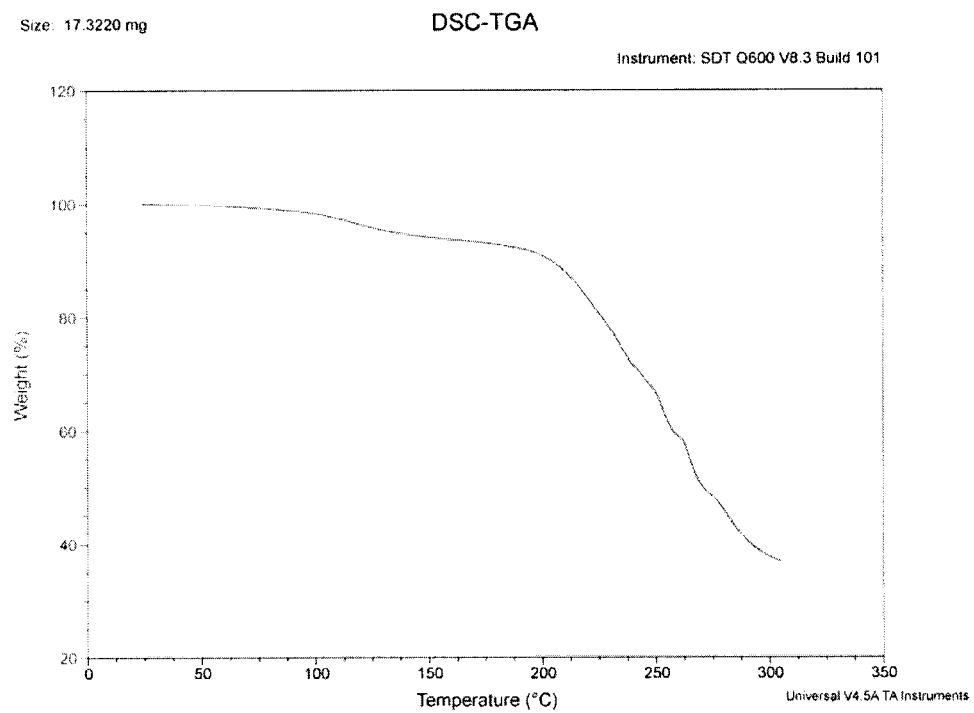
FIG. 15 is a thermogravimetric analysis (TGA) of a PAA-BZ polymer in an embodiment of the disclosure.

Example 8—Preparation of Anti-Microbial Polymer Crystals Using Acrylic Acid, and Benzyldimethyltetradecylammonium Chloride In a three neck flask, 0.125 g AIBN, 3.0 g BZ+2.0 g PAA+26.0 mL $H_2O$ (water) were mixed under magnetic stirring and gentle heating (less than 60° C.) until the BZ and AIBN and PAA was completely dissolved. The mixture was then heated to 80° C. for two hours. The heat as then turned off and the mixture was allowed to cool at room temperature over time. When the sample was bottled in sample vials and allowed to sit overnight, crystallization of the polymer was observed. An NMR spectrum of the PAA-BZ+H2O product is presented in FIG. 15. The reaction scheme is schematically similar to that depicted in Scheme 1.

Example 9—Viscosity Measurements

Viscosity measurements were taken of some of the polymers synthesized and are presented below in Tables 3-8. The measurements were taken using a Brookfield Synchro-lectric viscometer model LVF, the values are reported in centi-poise (mPa*s, m=milli) and calculated based as per the specifications set out by the instrument manufacturer.

Example 10A—Thermogravimetric Analysis

Figure 16:
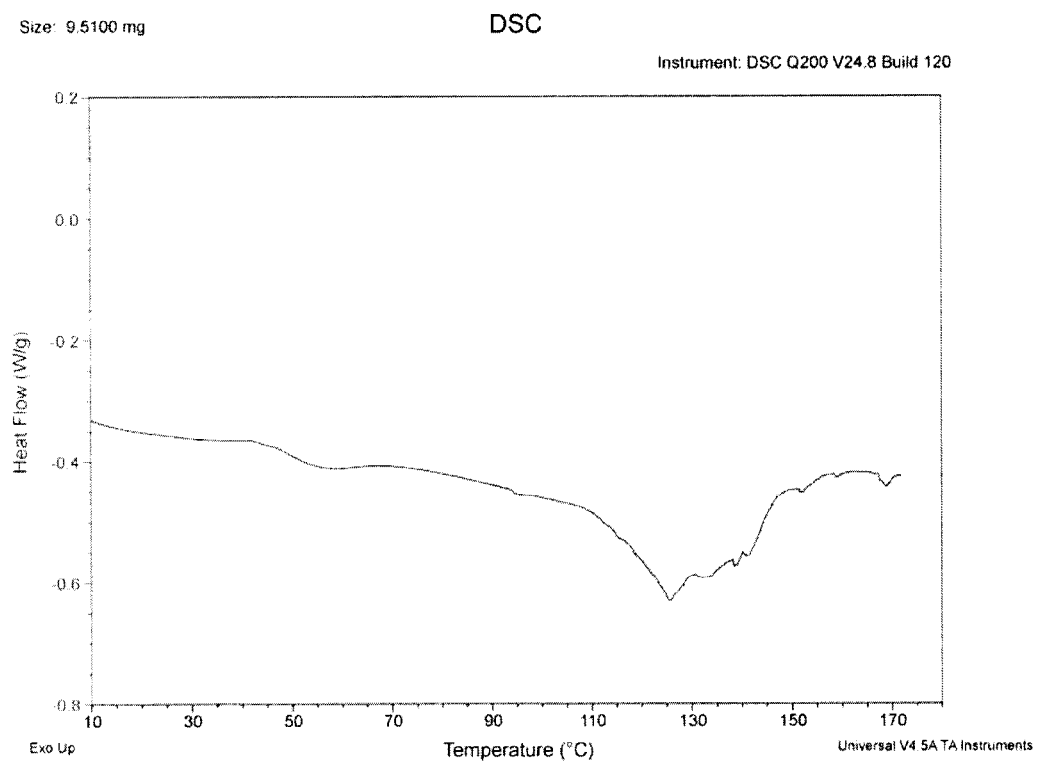
FIG. 16 is a differential scanning calorimetry (DSC) results of a PAA-BZ polymer in an embodiment of the disclosure.
Figure 17:
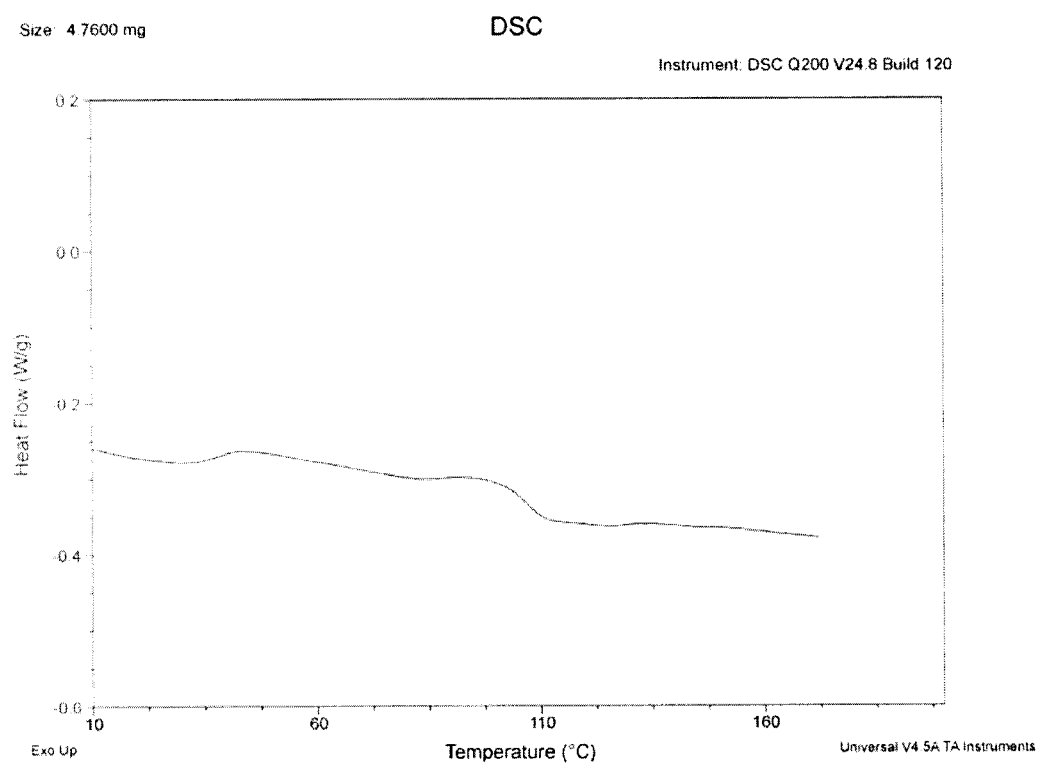
FIG. 17 is a differential scanning calorimetry (DSC) results of a PAA-BZ crystals in H2O in an embodiment of the disclosure.
Figure 18:
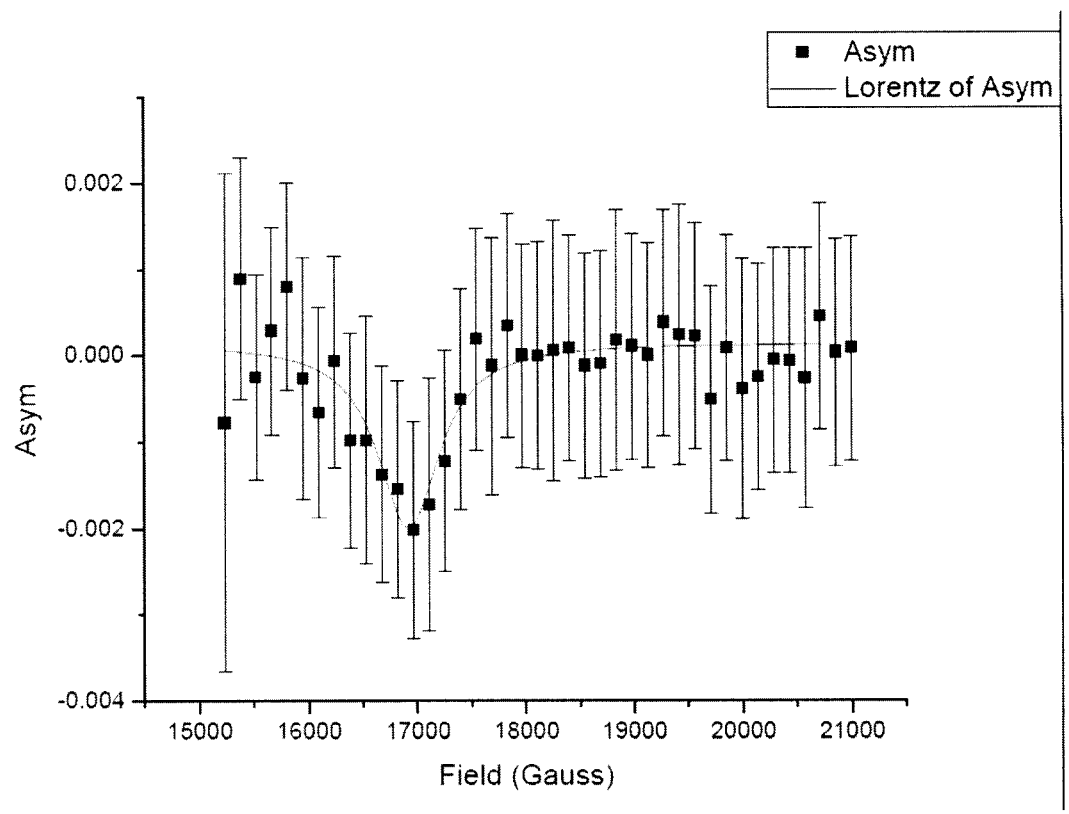
FIG. 18 is an avoided level crossing signal for free radical formed from addition of Mu to Bz at room temperature in an embodiment of the disclosure.
Figure 19:
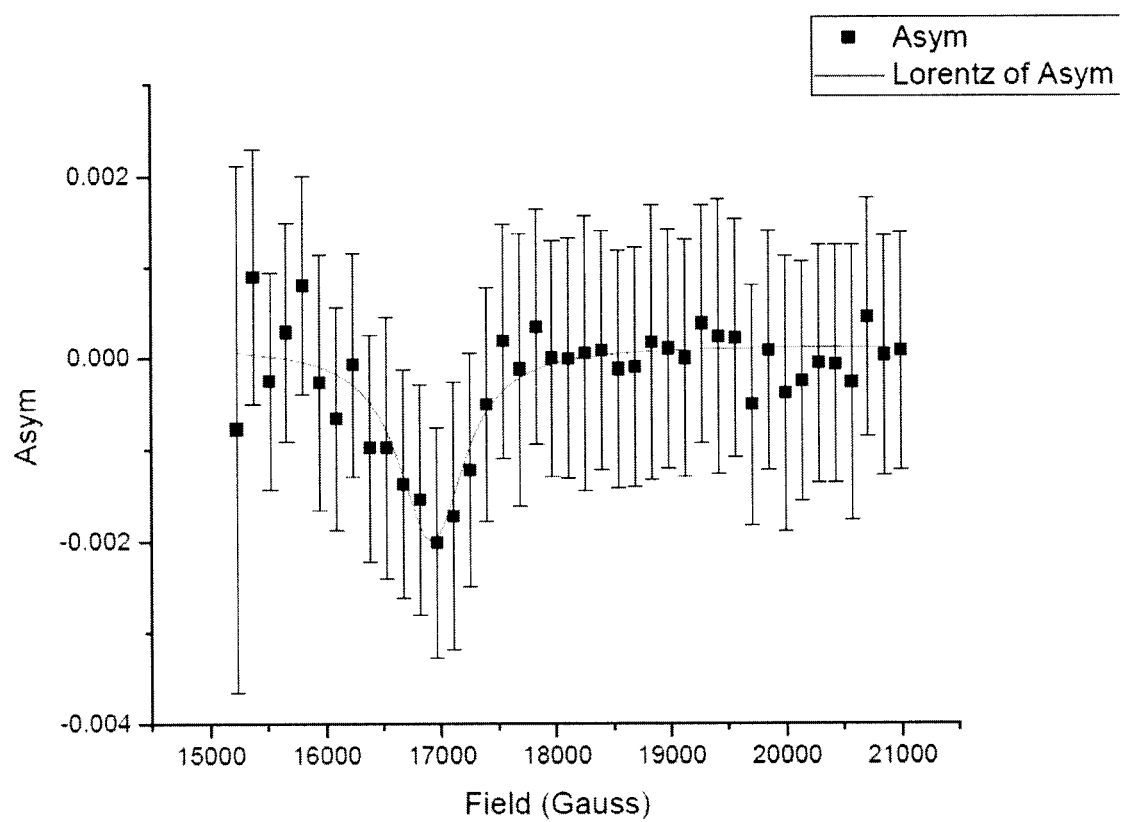
FIG. 19 is an avoided level crossing signal for free radical formed from addition of Mu to Bz at 30° C. in an embodiment of the disclosure.
Figure 20:
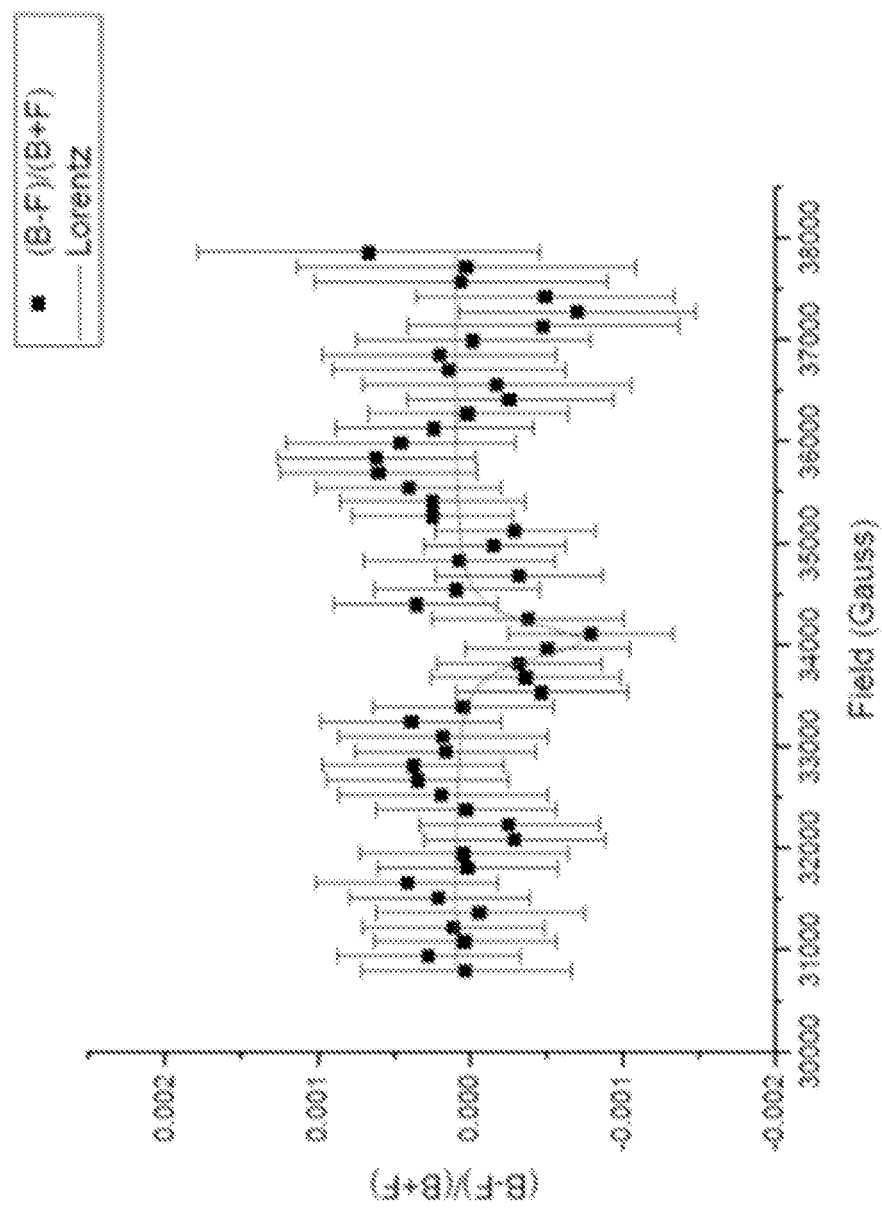
FIG. 20 is a high field avoided level crossing signal for free radical formed from addition of Mu to Bz at 30° C. in an embodiment of the disclosure.
Figure 21:
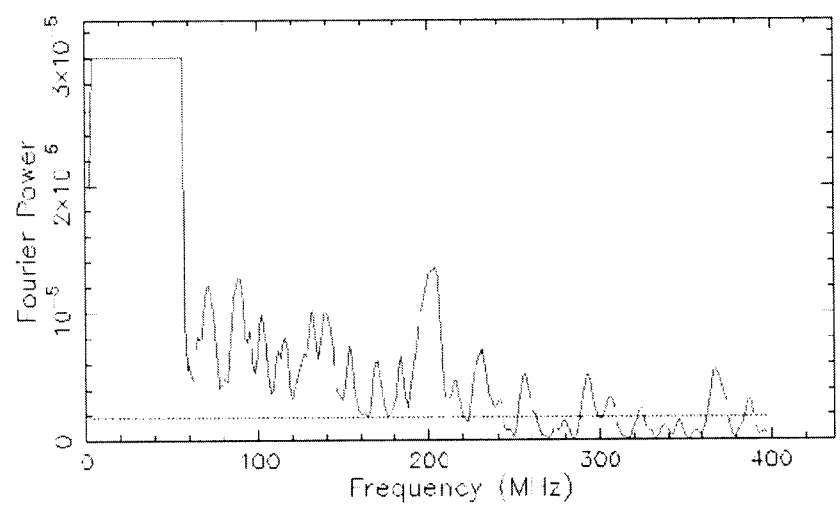
FIG. 21 is a TF-μSR Fourier power at 3.8 kG for free radical formed from addition of Mu to Bz at 95° C. in an embodiment of the disclosure.
Figure 22:
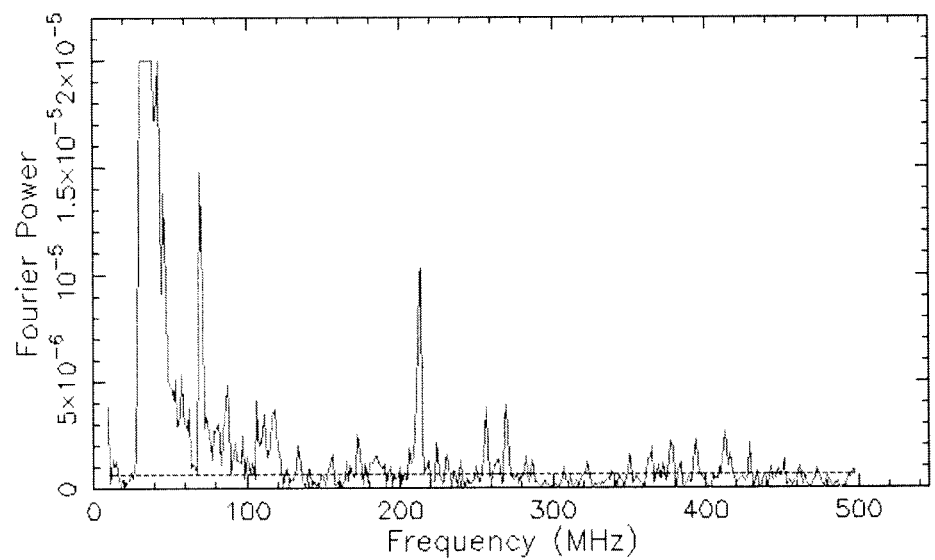
FIG. 22 is an Fourier transform of TF-μSR of Bz with added other monomer at low concentrations (less than 1M) at 35° C., 2.6 kG in an embodiment of the disclosure.

The PAA-BZ polymer was tested using thermogravimetric analysis (TGA) (FIG. 15) and differential scanning calorimetry (DSC) (FIG. 16). The PAA-BZ+H2O crystals were also tested using DSC (FIG. 17). The results of these tests are presented in FIGS. 15-17 respectively. The TGA demonstrates this polymer's thermal stability up to 200° C. making it amenable to extrusion, molding and other processing techniques or applications below that temperature.

Example 10B—Free Radical Studies Using uSR

The free radical intermediates from addition to Bz were studied using μASR technique at M20 beam line. Some of the signals for formed free radicals are presented in FIGS. 18 to 22. These results suggest that the initial free radical (such as muonium) is added to the para position of the benzyl group within the benzylammonium chloride molecule for the polymerization reaction. This radical addition is schematically depicted below in below.

Figure 23:
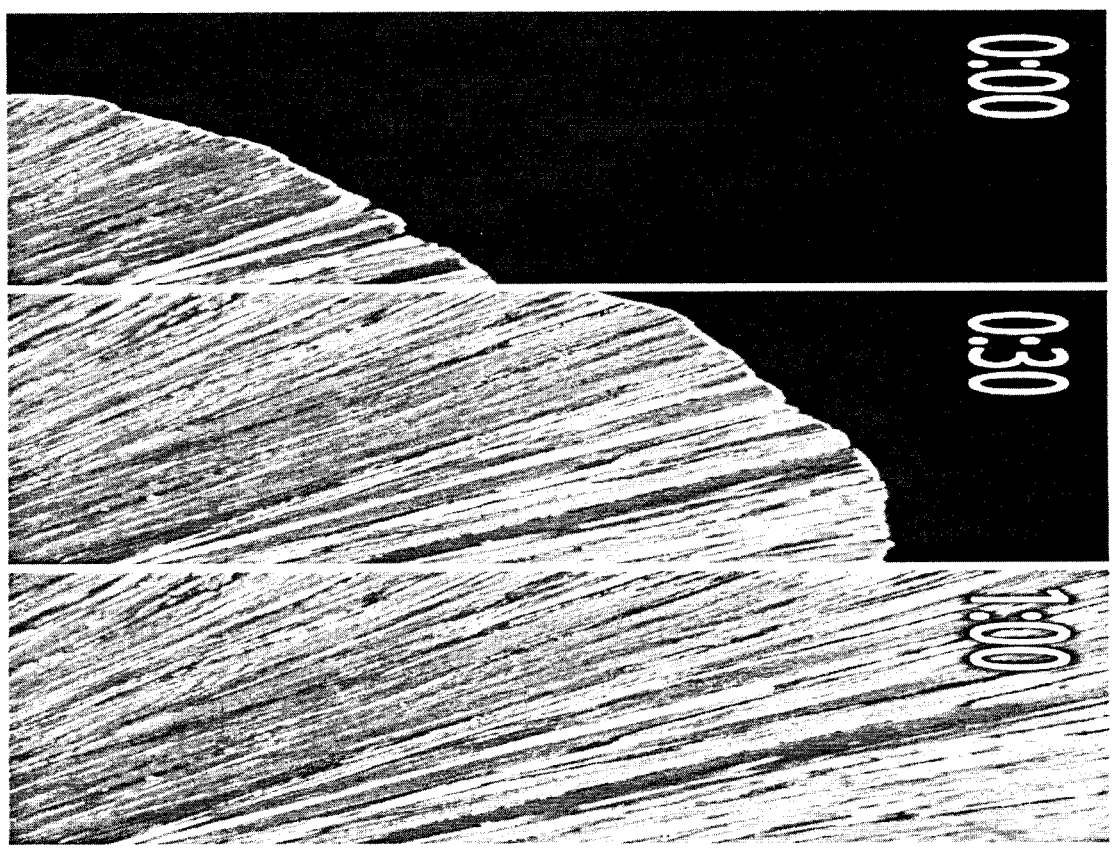
FIG. 23 are polarized optical micrographs (×100 magnification) of a 0.25 mole fraction solution of styrene in Bz in the presence of initiator (AIBN) at 35±5 C in an embodiment of the disclosure.

As shown by FIG. 23, when additional compounds (e.g. acrylic acid or an alcohol) are added even at very low concentration, the radical formation is enhanced and under some conditions a liquid crystal is formed that leads to an antimicrobial polymeric liquid crystal after free radical formation. Such liquid crystalline polymeric materials with anti-microbial properties have applications in optical sensors that detect or identify bacteria or the presence of biological materials.

Figure 24:
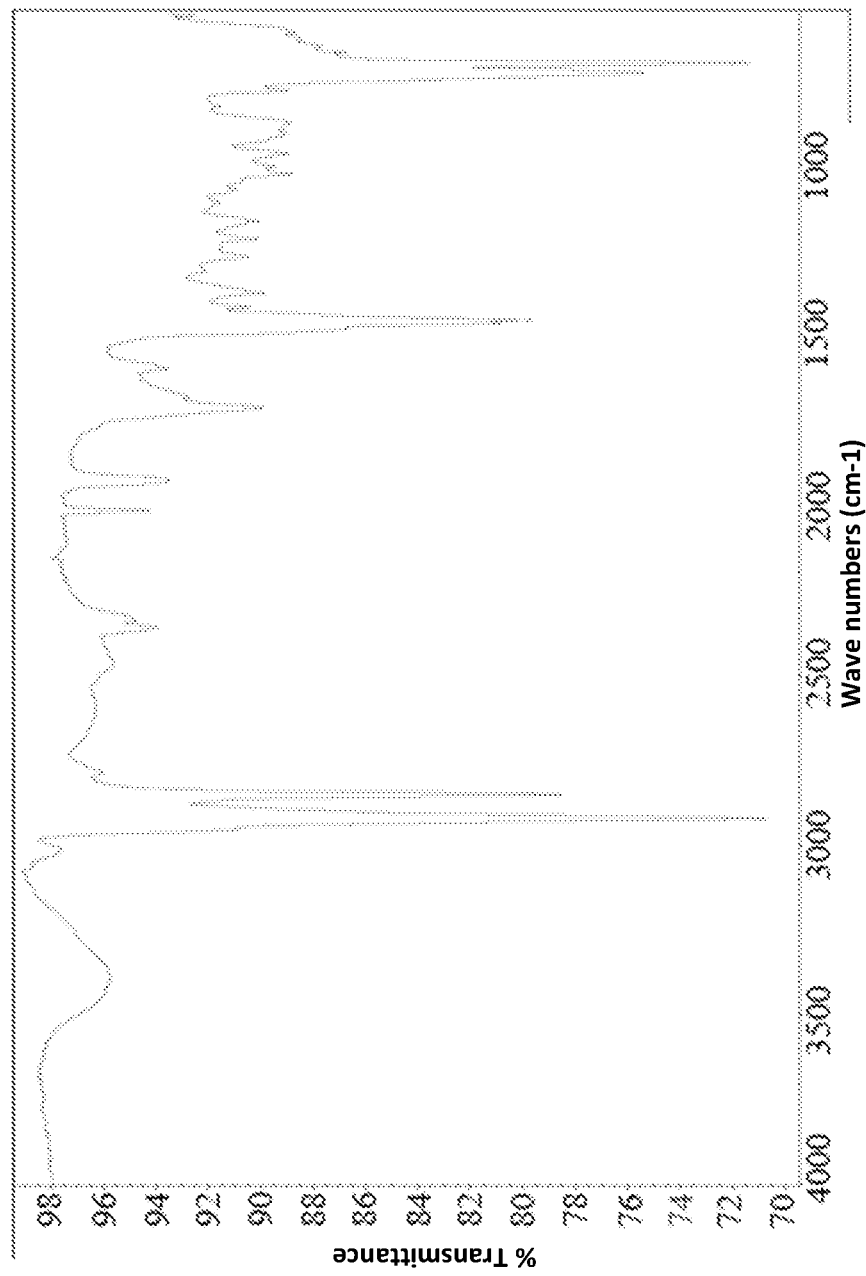
FIG. 24 is an FTIR spectrum of the BZ homopolymer polymer product in an embodiment of the disclosure.
Figure 25:
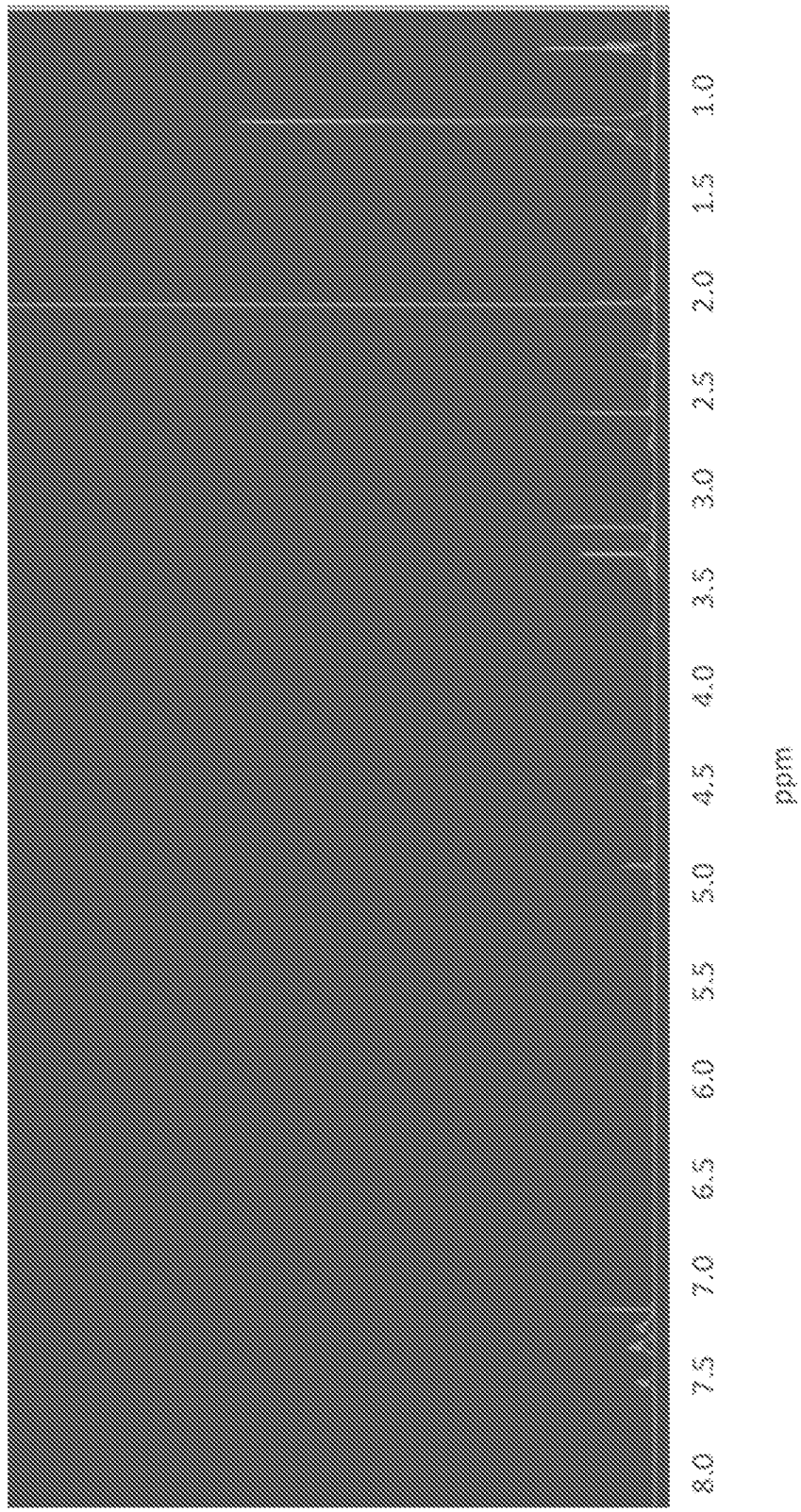
FIG. 25 is an $^1$H NMR spectrum of the BZ Homopolymer product in an embodiment of the disclosure.
Figure 26:
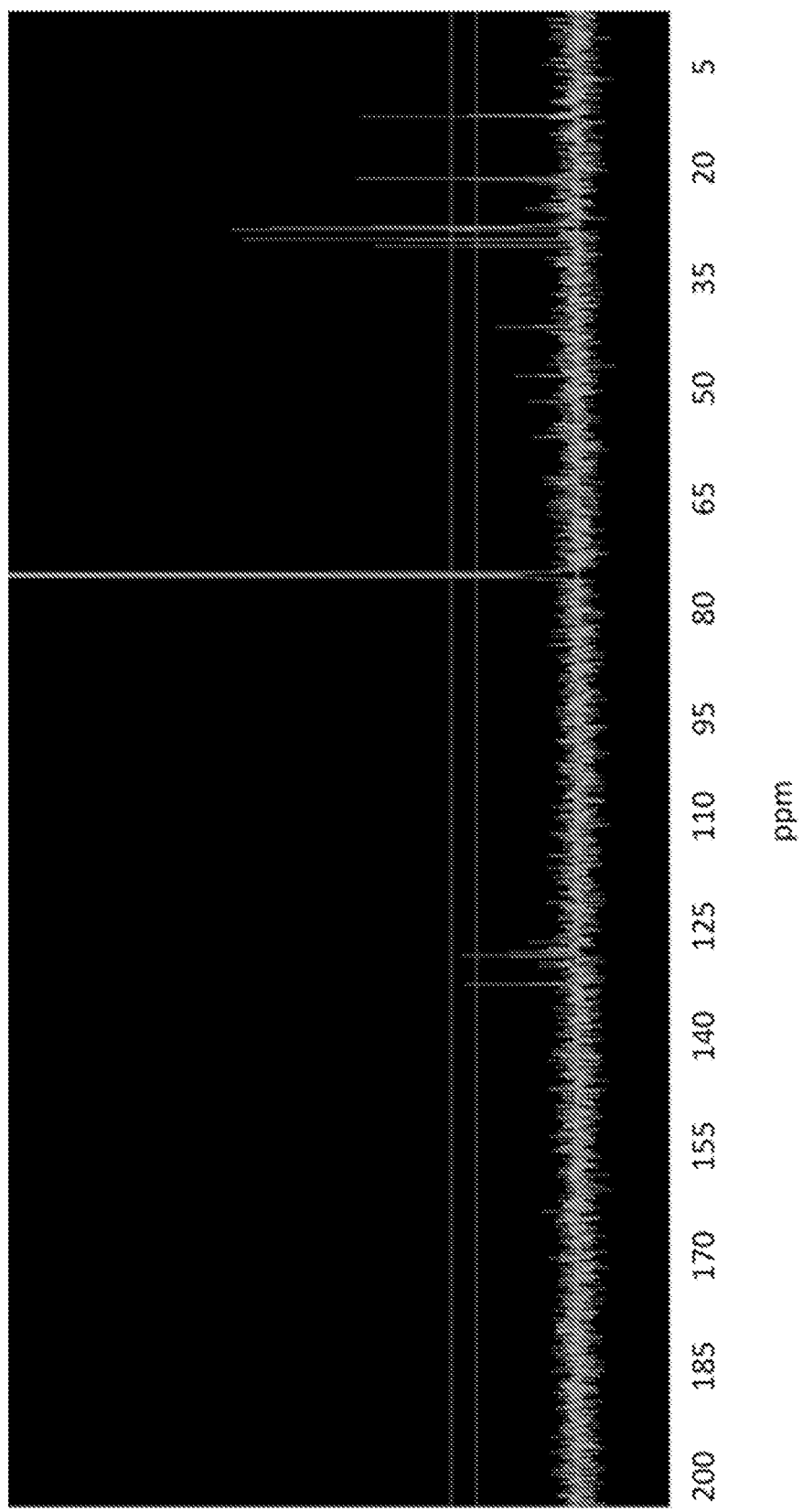
FIG. 26 is a $^{13}$C NMR spectrum of the BZ Homopolymer product in an embodiment of the disclosure.

Example 11—Preparation of Anti-Microbial Homopolymer of Benzylalkylammonium Chloride 0.99 g of benzalkonium chloride (C14) was heated and stirred in a round bottom flask. When the temperature reached 115° C., 0.33 mL of 30% hydrogen peroxide solution was added to the flask. The heat was left on and the solution began boiling, with the temperature increasing until it reached 175° C. after 23 minutes. The solution slowly turned pale yellow then darkened to orange and then a dark brown liquid. After 32 minutes the heat was turned off. Upon cooling the product thickened to a very viscous liquid and became a light brown soft semi-solid. The reaction is schematically shown in Scheme 7, showing products of the BZ homopolymerization, where p is an integer between 1 and 1,000,000 and R represents a long alkyl chain, in this particular reaction R is a C14H29 alkyl chain. A is a suitable counter-ion, in this particular reaction A is a chloride anion, and X is any substitution on the benzyl ring and in this instance is an H. An FTIR, $^1H$ and $^{13}C$ NMR spectrum of the product is shown in FIGS. 24, 25 and 26, respectively.

Scheme 7

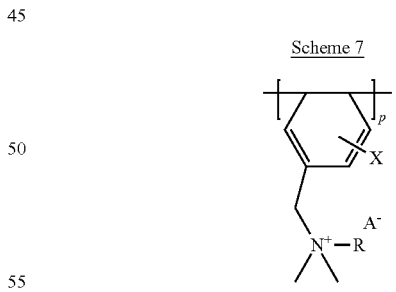

Figure 27:
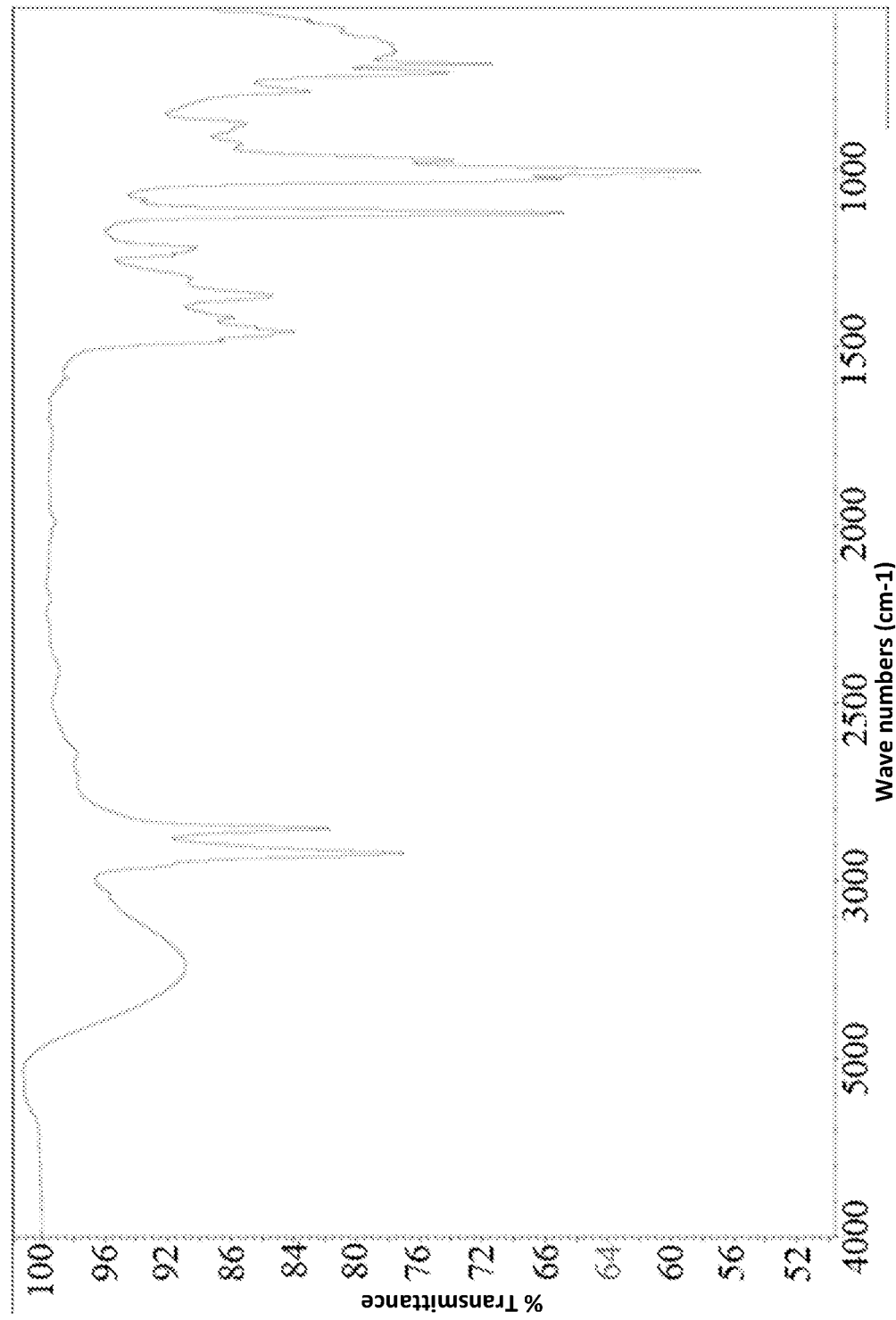
FIG. 27 is an FTIR spectrum of the 2-Butyne-1,4-diol and benzyldimethyltetradecylammonium chloride polymer product in an embodiment of the disclosure.

Example 12—Preparation of Anti-Microbial Polymer Using 2-Butyne-1,4-diol and Benzyldimethyltetradecylammonium Chloride In a three neck flask, 0.7 g of 2-Butyne-1,4-diol (BYOL) and 3 g of Benzyldimethyltetradecylammonium chloride (BZ) were mixed under magnetic stirring and gentle heating until the BZ was completely melted, and the solution mixed to form a clear-yellow solution. The mixture was then heated to 120° C. and the heat was turned off, but magnetic stirring continued. 0.09 g of the initiator 2,2'-Azobis(2-methylpropionitrile) (AIBN) was immediately added to the reaction mixture and the polymerization was initiated. As the reaction is exothermic, the temperature of the mixture continued to rise until the reaction was complete. After approximately 15 minutes the reaction was stopped, and the blood orange like dark red product solution was collected (yield 2.81 g). The product is a viscous sticky liquid, which crystallizes within an hour in the sample vial it is transferred to. This reaction was also carried out with different initiator and monomer concentrations using the same procedure and experimental conditions described above where the concentrations were changed to (0.7 g BYOL, 3 g BZ and 0.19 gAIBN) or using (3 g Bz, 2.39 g ByOL and 0.13 g AIBN). These varied conditions also produced orange to red colored liquid polymers that crystallized after polymerization. The reaction products are schematically depicted in Scheme 8, showing products of the polymerization reaction, where m, q and p are integers between 1 and 1,000,000, optionally q maybe 0, and R represents a long alkyl chain, in this particular reaction R is a C14H29 alkyl chain, A is a suitable counter-ion, in this particular reaction A is a chloride anion, and C is the monomer of the co-polymer, in this particular reaction it is 2-Butyne-1,4-diol. An FTIR, of the product is shown in FIG. 27.

Scheme 8

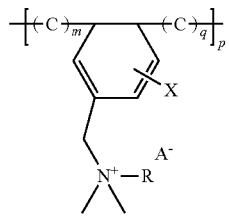

Figure 28:
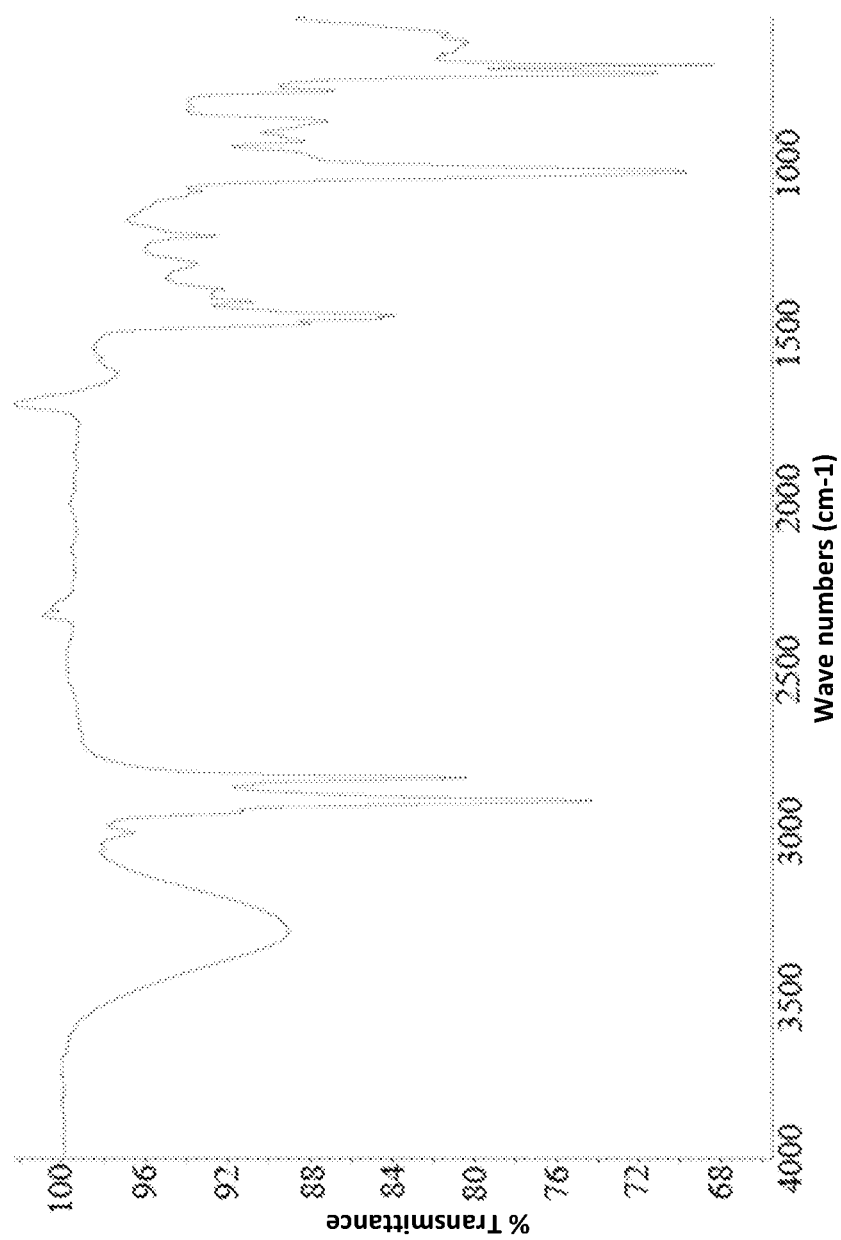
FIG. 28 is an FTIR spectrum of the cis-2-Butene-1,4-diol and benzyldimethyltetradecylammonium chloride polymer product in an embodiment of the disclosure.

Example 13—Preparation of Anti-Microbial Polymer Using cis-2-Butene-1,4-diol and Benzyldimethyltetradecylammonium Chloride In a three neck flask, 0.67 ml of cis-2-Butene-1,4-diol (BEOL) and 3 g of Benzyldimethyltetradecylammonium chloride (BZ) were mixed under magnetic stirring and gentle heating until the BZ was completely melted, and the solution mixed to form a clear-yellow solution. The mixture was then heated to 100° C. and the heat as turned off, but magnetic stirring continued. 0.09 g of the initiator 2,2'-Azobis(2-methylpropionitrile) (AIBN) was immediately added to the reaction mixture and the polymerization was initiated. As the reaction is exothermic, the temperature of the mixture continued to rise until the reaction was complete. After approximately 10 minutes the reaction was stopped, and the clear to yellow viscous liquid was collected (yield 2.74 g). This reaction was also carried out with different initiator and monomer concentrations using the same procedure and experimental conditions described above where the concentrations were changed to (0.6 ml BEOL, 3 g BZ and 0.18 g AIBN) or using (3.01 g Bz, 2.28 ml BEOL and 0.14 g AIBN). These varied conditions also produced a clear to yellowish viscous liquid product. The reaction products are similar to those schematically depicted in Scheme 8, where in this particular reaction R is a C14H29 alkyl chain, A is a chloride anion, and C in this particular reaction is cis-2-Butene-1,4-diol. An FTIR, spectrum of the product is presented in FIG. 28.

Figure 29:
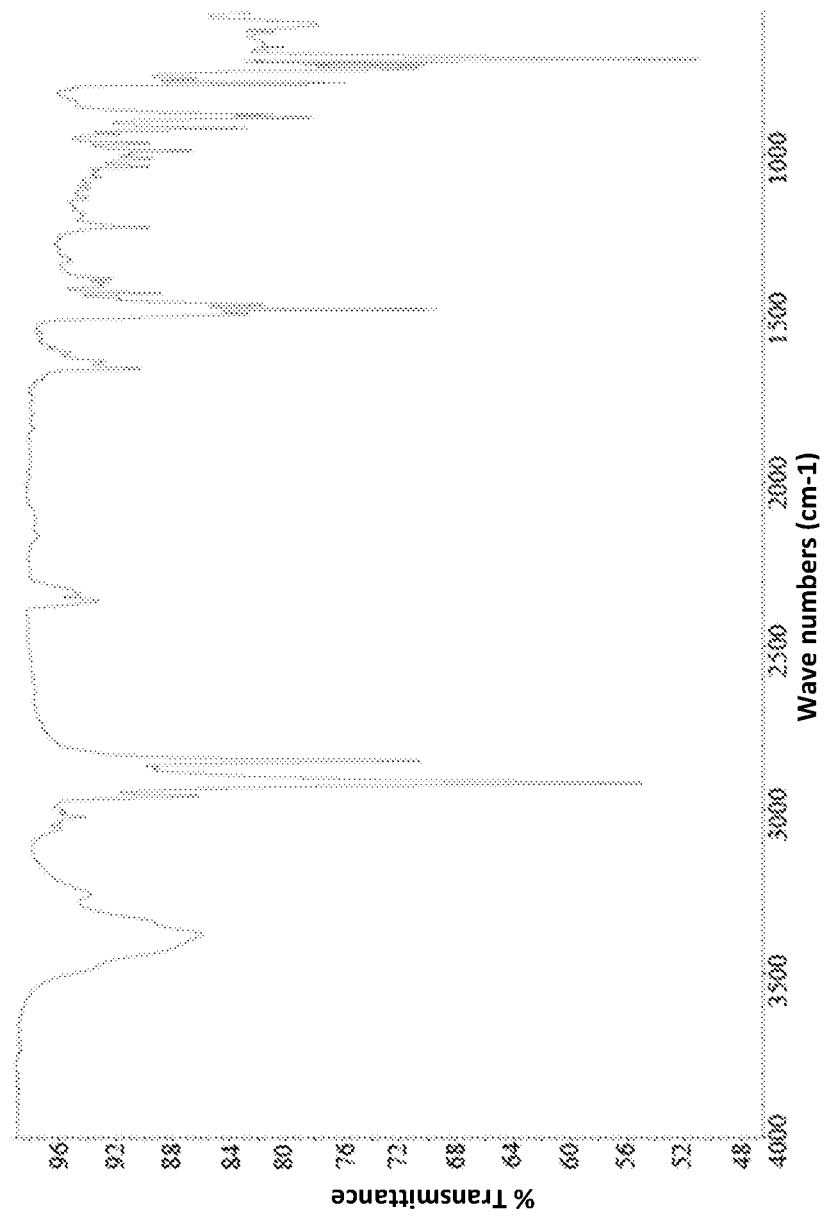
FIG. 29 is an FTIR spectrum of the styrene and benzyldimethyltetradecylammonium chloride polymer product in an embodiment of the disclosure.

Example 14—Preparation of Anti-Microbial Polymer Using Styrene and Benzyldimethyltetradecylammonium Chloride In a three neck flask, 3.18 ml of styrene (STY) and 3 g of Benzyldimethyltetradecylammonium chloride (BZ) were mixed under magnetic stirring and gentle heating until the BZ was completely melted, and the solution mixed to form a clear solution. The mixture was then heated to 70° C. and the heat was turned off, but magnetic stirring continued. 0.15 g of the initiator 2,2'-Azobis(2-methylpropionitrile) (AIBN) was immediately added to the reaction mixture and the polymerization was initiated. After approximately 30 minutes the reaction was stopped, and the yellowish, white solid product was collected (yield 3.08 g). This reaction was also carried out with different initiator and monomer concentrations as well as temperatures at which the initiator was added using the same procedure and experimental conditions described above where the concentrations were changed to (3.18 ml STY, 3 g BZ and 0.07 g AIBN added at 90° C.) or using (3.18 ml STY, 3 g BZ and 0.15 g AIBN added at 90° C.). These varied conditions also produced a clear to yellow to white solid polymeric product. The reaction products are similar to those schematically depicted in Scheme 8, where in this particular reaction R is a C14H29 alkyl chain, A is a chloride anion, and C in this particular reaction is styrene. An FTIR, of the product is presented in FIG. 29.

Figure 30:
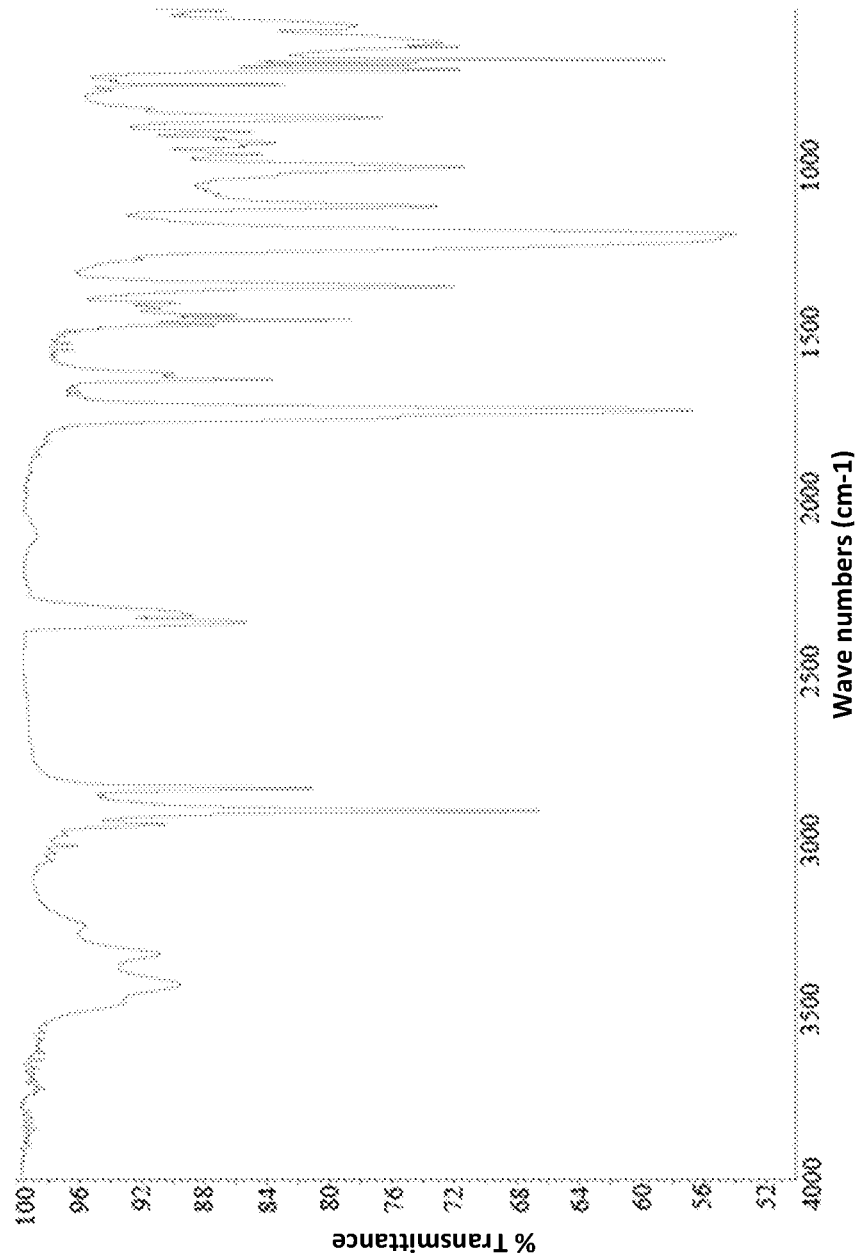
FIG. 30 is an FTIR spectrum of the vinyl acetate and benzyldimethyltetradecylammonium chloride polymer product in an embodiment of the disclosure.
Figure 31:
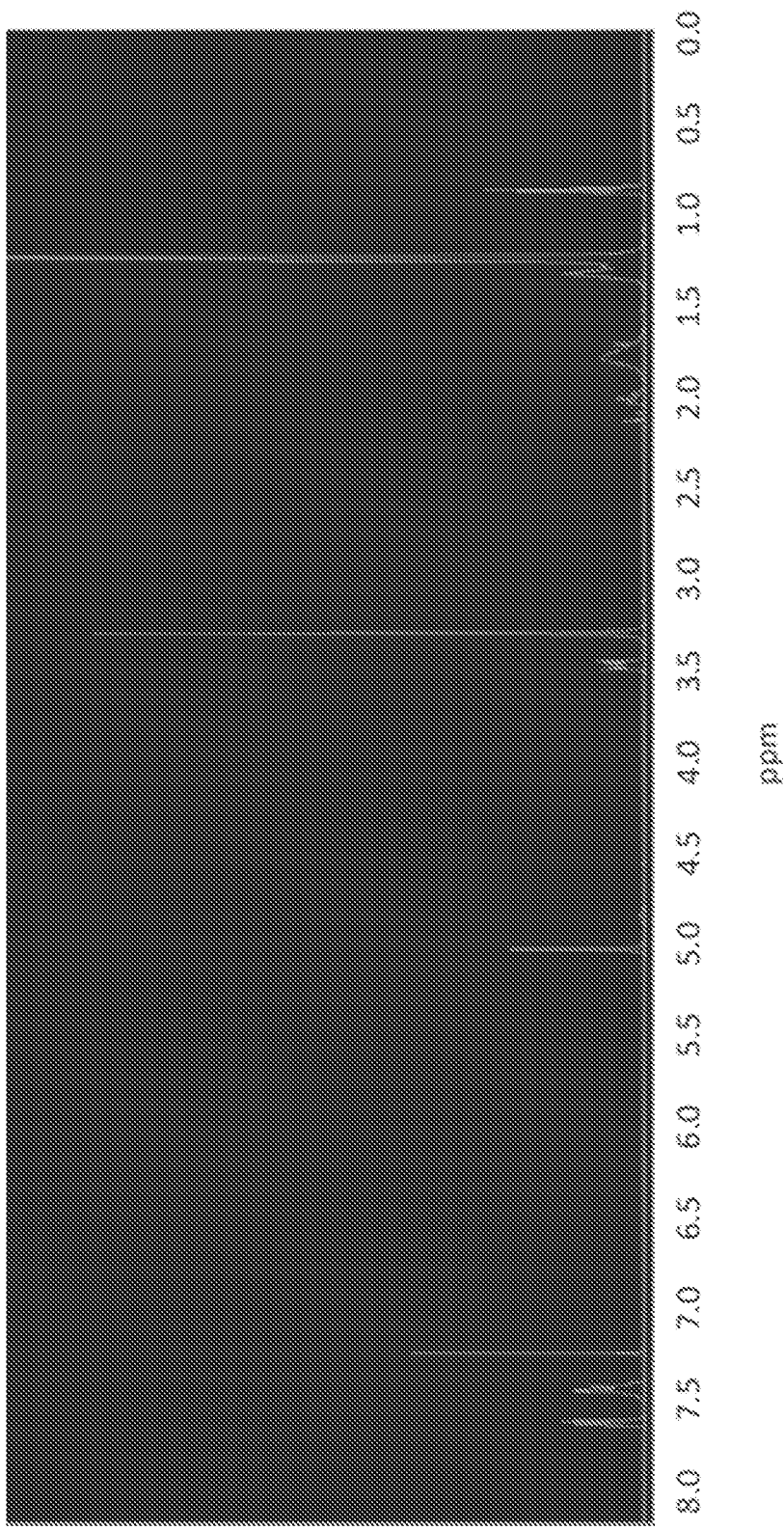
FIG. 31 is an $^1$H NMR spectrum of the vinyl acetate and benzyldimethyltetradecylammonium chloride polymer product in an embodiment of the disclosure.
Figure 32:
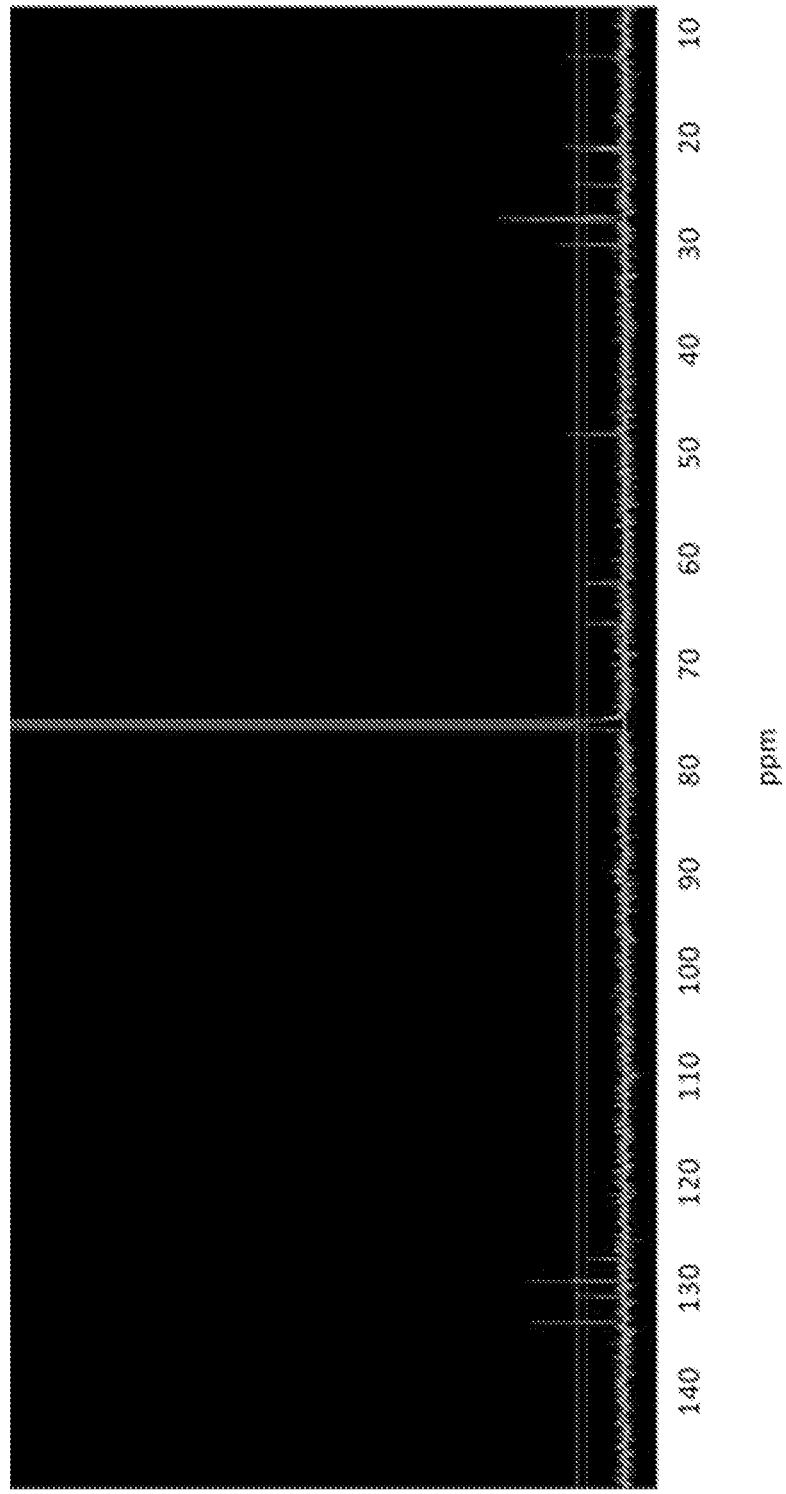
FIG. 32 is a $^{13}$C NMR spectrum of the vinyl acetate and benzyldimethyltetradecylammonium chloride polymer product in an embodiment of the disclosure.

Example 15—Preparation of Anti-Microbial Polymer Using Vinyl Acetate and Benzyldimethyltetradecylammonium Chloride In a three neck flask, 2.56 ml of vinyl acetate (VA) and 3 g of Benzyldimethyltetradecylammonium chloride (BZ) were mixed under magnetic stirring and gentle heating until the BZ was completely melted, and the solution mixed to form a clear solution. The mixture was then heated to 63° C. and the heat was turned off, but magnetic stirring continued. 0.15 g of the initiator 2,2'-Azobis(2-methylpropionitrile) (AIBN) was immediately added to the reaction mixture and the polymerization was initiated. After approximately 20 minutes the reaction was stopped, and the product, which was lemon-merengue like in color and a thick paste, was collected. This reaction was also carried out with different initiator and monomer concentrations using the same procedure and experimental conditions described above where the concentrations were changed to (2.56 ml VA, 3 g BZ and 0.28 g AIBN) or using (2.65 ml VA, 3 g BZ and 0.06 g AIBN). These varied conditions also produced light yellow to off-white, thick paste like solid polymeric products. The reaction products are similar to those schematically depicted in Scheme 8, where in this particular reaction R is a C14H29 alkyl chain, A is is a chloride anion, and C in this particular reaction is vinyl acetate. An FTIR, $^1$H and $^{13}$C NMR spectrum of the product is shown in FIGS. 30, 31 and 32 respectively.

Figure 33:
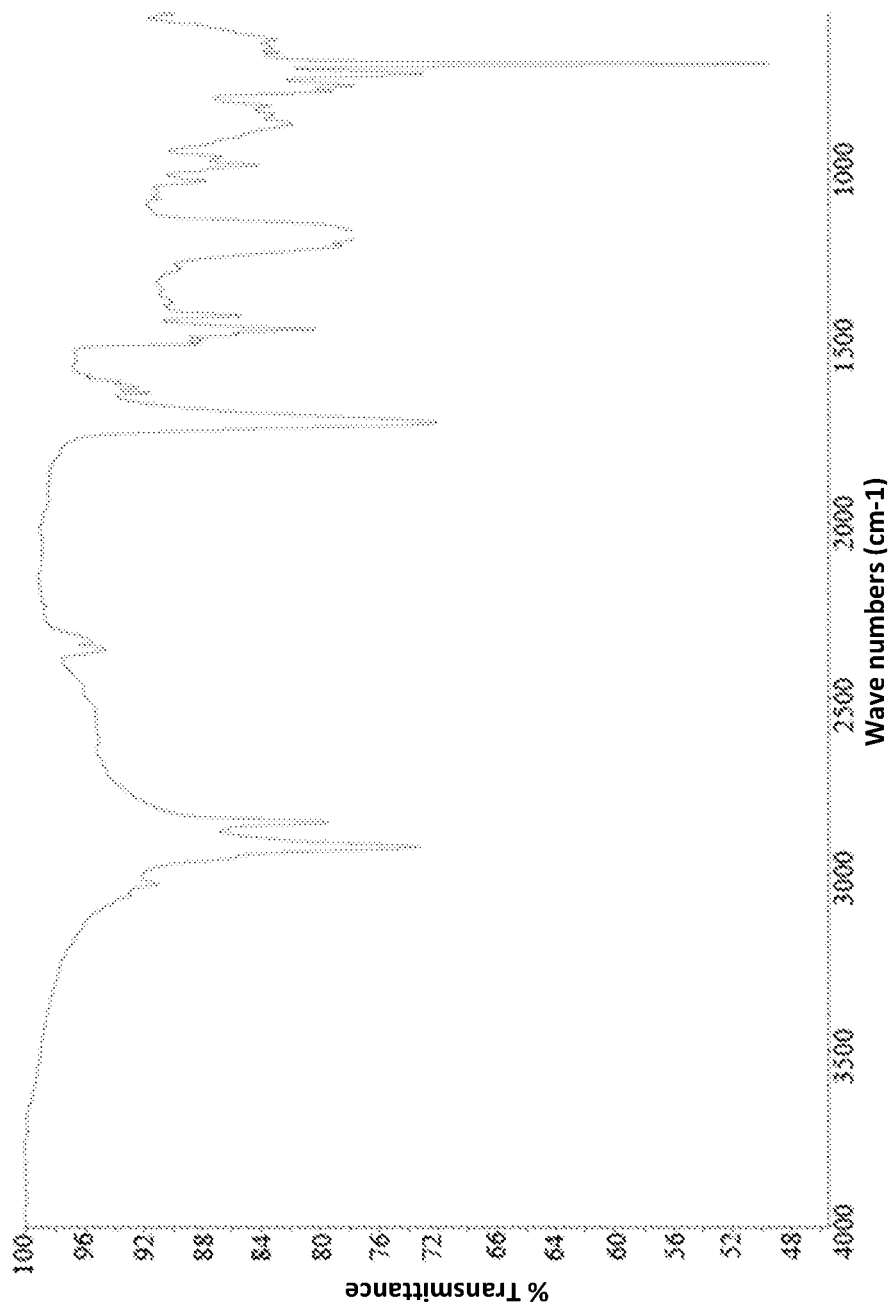
FIG. 33 is an FTIR spectrum of the styrene, acrylic acid and benzyldimethyltetradecylammonium chloride polymer product in an embodiment of the disclosure.

Example 16—Preparation of Anti-Microbial Polymer Using Styrene, Acrylic Acid and Benzyldimethyltetradecylammonium Chloride In a three neck flask, 0.95 ml of Acrylic Acid (AA), 1.59 ml Styrene (STY) and 3 g of Benzyldimethyltetradecylammonium chloride (BZ) and were mixed under magnetic stirring and gentle heating until the BZ was completely melted, and the solution mixed to form a clear solution. The mixture was then heated to 98° C. and the heat wasis turned off, but magnetic stirring continues. 0.14 g of the initiator 2,2'-Azobis(2-methylpropionitrile) (AIBN) was immediately added to the reaction mixture and the polymerization was initiated. After approximately 15 minutes the reaction was stopped, and the product, which is clear, and sticky (glue-like) was collected (yield 2.45 g). This reaction was also carried out with different initiator and monomer concentrations using the same procedure and experimental conditions described above where the concentrations were changed to (2.8 ml STY, 0.56 ml AA, 3 g BZ and 0.15 g AIBN) or using (0.94 ml STY, 1.67 ml AA, 3 g BZ and 0.14 g AIBN). These varied conditions also produced clear, sticky polymeric products. The reaction products are similar to those schematically depicted in Scheme 6, where in this particular reaction R is a C14H29 alkyl chain, A is a chloride anion, and B, C, C' and B' are monomers of the copolymer, in this instance they optionally represent STY or AA monomers, oligomers or polymers. An FTIR spectrum of the product is presented in FIG. 33.

Figure 34:
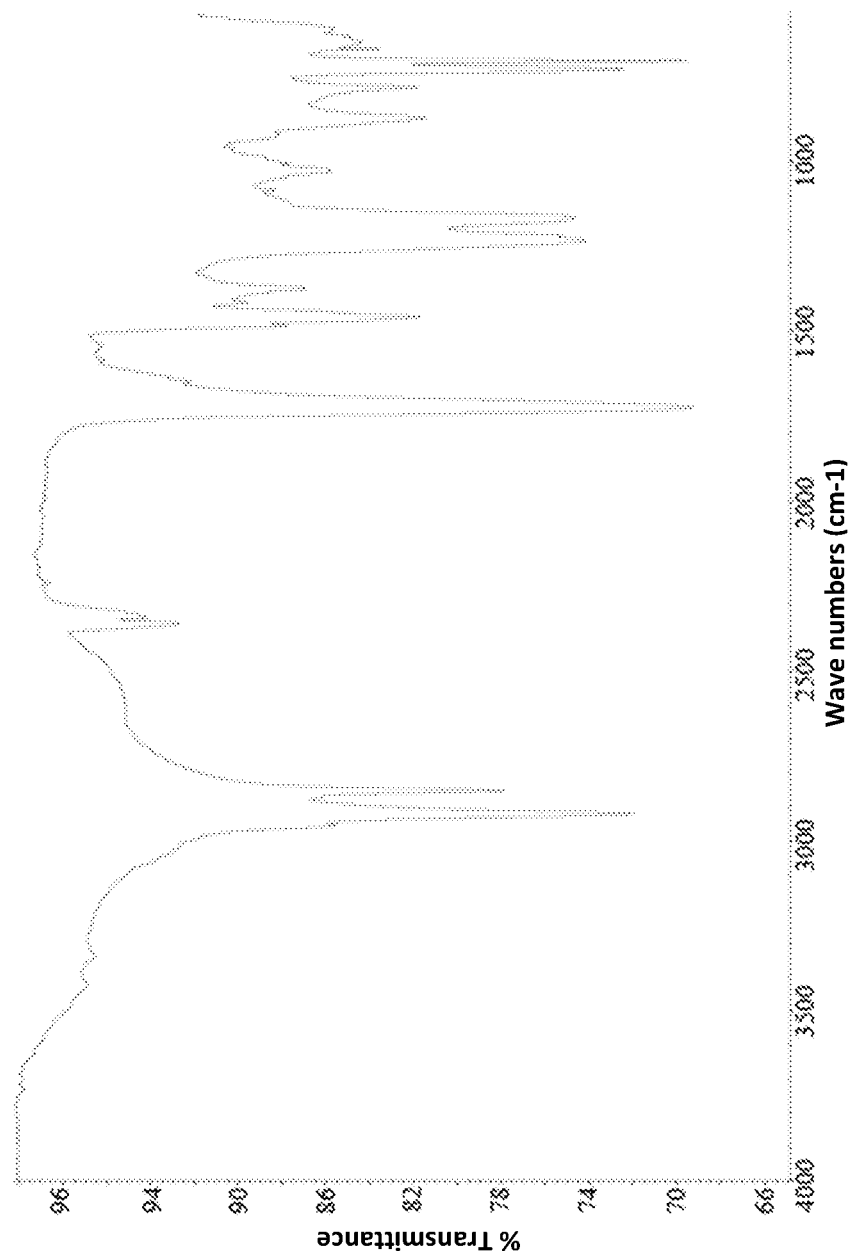
FIG. 34 is an FTIR spectrum of the vinyl acetate, acrylic acid and benzyldimethyltetradecylammonium chloride polymer product in an embodiment of the disclosure.
Figure 35:
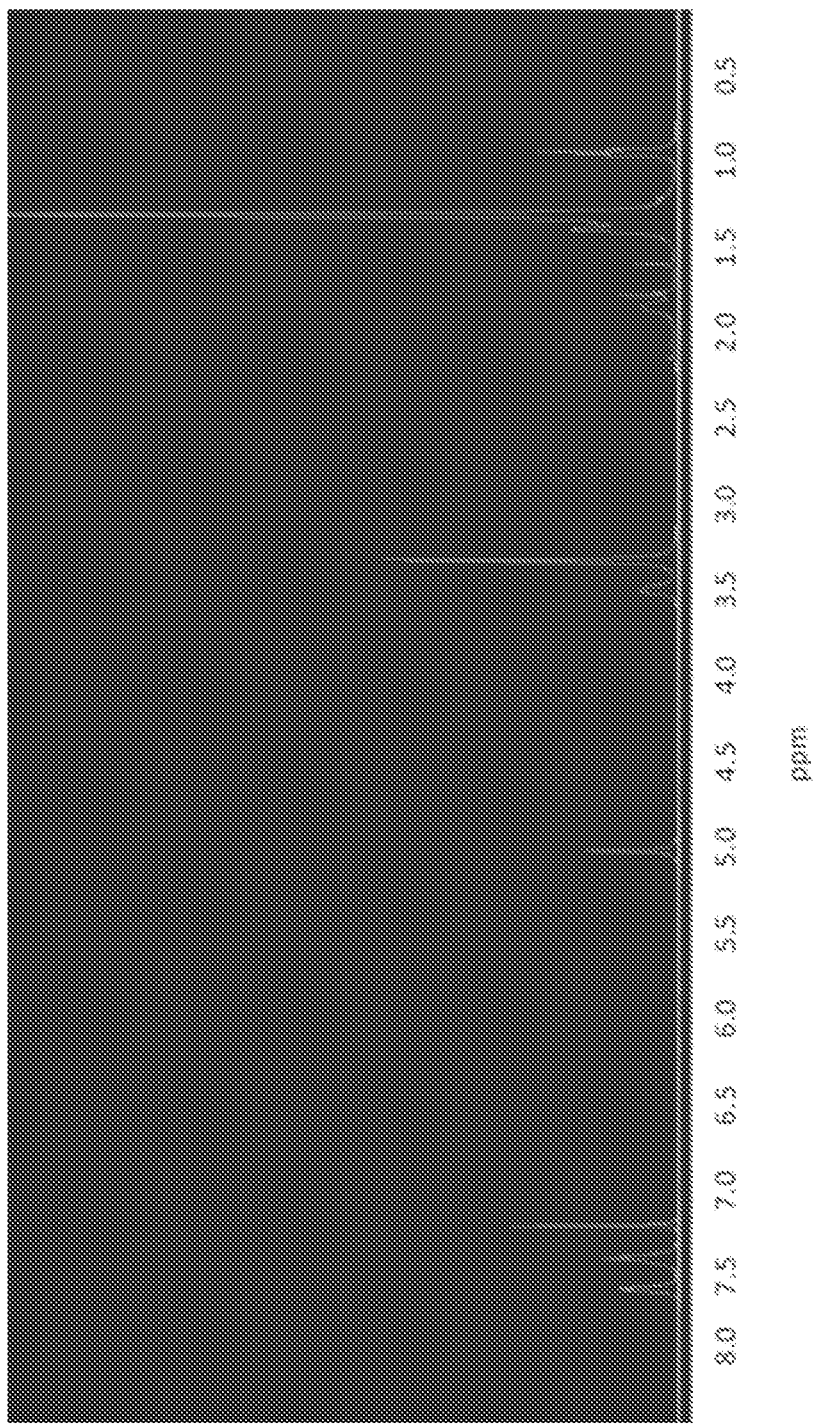
FIG. 35 is a $^1$H NMR spectrum of the vinyl acetate, acrylic acid benzyldimethyltetradecylammonium chloride polymer product in an embodiment of the disclosure.
Figure 36:
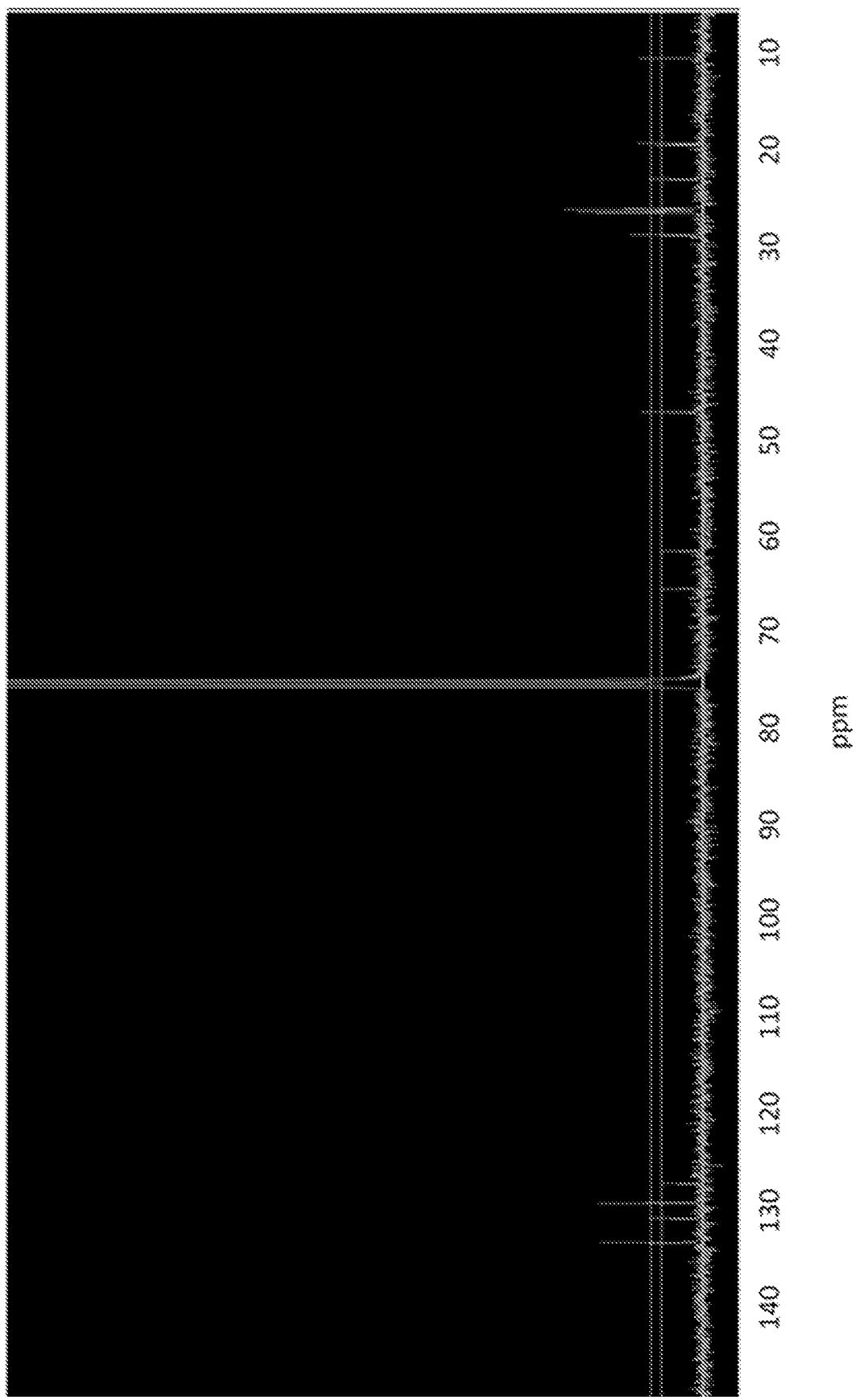
FIG. 36 is a $^{13}$C NMR spectrum of the vinyl acetate, acrylic acid benzyldimethyltetradecylammonium chloride polymer product in an embodiment of the disclosure.

Example 17—Preparation of Anti-Microbial Polymer Using Vinyl Acetate, Acrylic Acid and Benzyldimethyltetradecylammonium Chloride In a three neck flask, 0.56 ml of Acrylic Acid (AA), 2.26 ml Vinyl Acetate (VA) and 3 g of Benzyldimethyltetradecylammonium chloride (BZ) and were mixed under magnetic stirring and gentle heating until the BZ was completely melted, and the solution mixed to form a clear solution. The mixture was then heated to 65° C. and the heat was turned off, but magnetic stirring continues. 0.14 g of the initiator 2,2'-Azobis(2-methylpropionitrile) (AIBN) was immediately added to the reaction mixture and the polymerization was initiated. After approximately 15 minutes the reaction is stopped, and the product, which is an opaque-white, soft polymeric solid was collected (yield 3.27 g). This reaction was also carried out with different initiator and monomer concentrations using the same procedure and experimental conditions described above where the concentrations were changed to (0.75 ml VA, 1.67 ml AA, 3 g BZ and 0.14 g AIBN) producing a compressible, but more sturdy white polymer. The reaction products are similar to those schematically depicted in Scheme 6, where in this particular reaction R is a C14H29 alkyl chain, A is a chloride anion, and B, C, C' and B' are monomers of the copolymer, in this instance they optionally represent VA or AA monomers, oligomers or polymers. An FTIR, $^1$H and $^{13}$C NMR spectrum of the product is presented in FIGS. 34,35 and 36 respectively.

Figure 37:
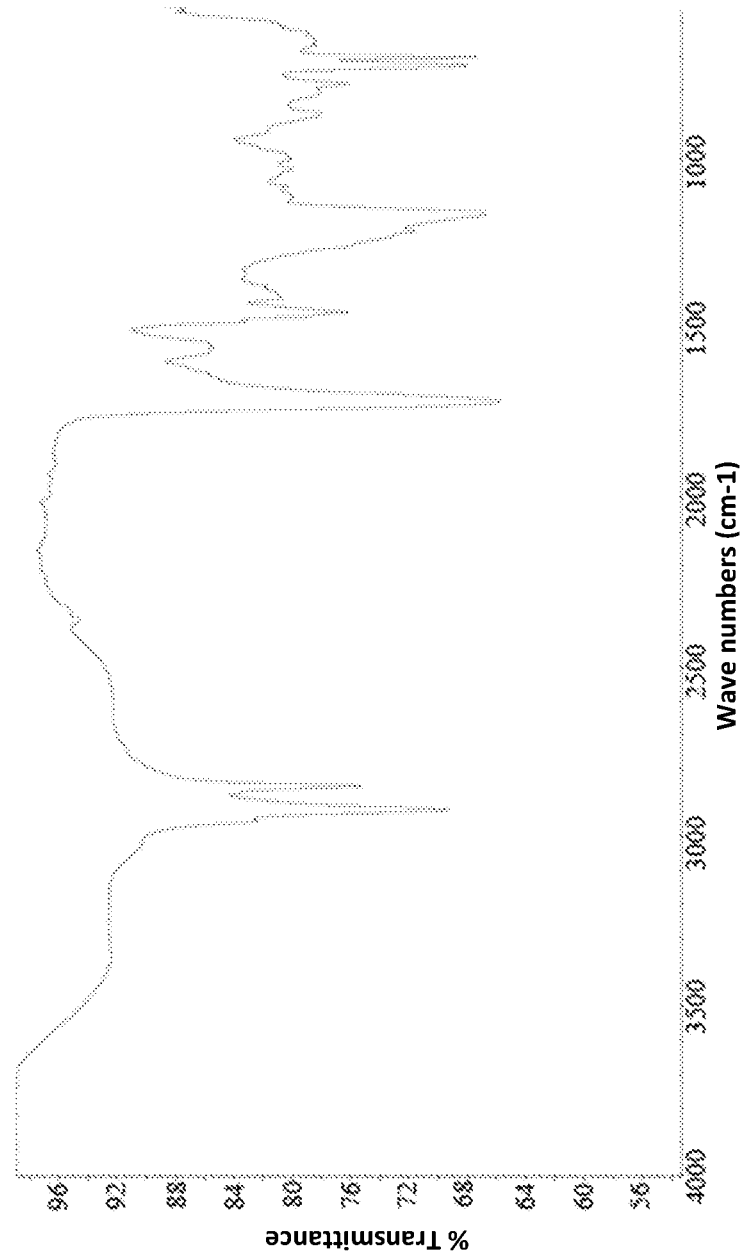
FIG. 37 is an FTIR spectrum of the pentaerythritol allyl ether, acrylic acid and benzyldimethyltetradecylammonium chloride polymer product in an embodiment of the disclosure.

Example 18—Preparation of Anti-Microbial Polymer Using Acrylic Acid, Pentaerythritol Allyl Ether and Benzyldimethyltetradecylammonium Chloride In a three neck flask 5.00 mL of acrylic acid (AA), 7.5 g of benzyldimethyltetradecylammonium chloride (BZ), and 0.1849 mL of 70% pentaerythritol allyl ether (APE) were added to a 100 mL beaker equipped with a thermometer and stir bar. The solution was stirred and heated to 70° C., at which point 0.319 g AIBN was added to initiate polymerization. The reaction is quick and exothermic, yielding 10.48 g (82% yield) of a cross-linked PAA-BZ-APE polymer. An FTIR, spectrum of the product is presented in FIG. 37.

Figure 38:
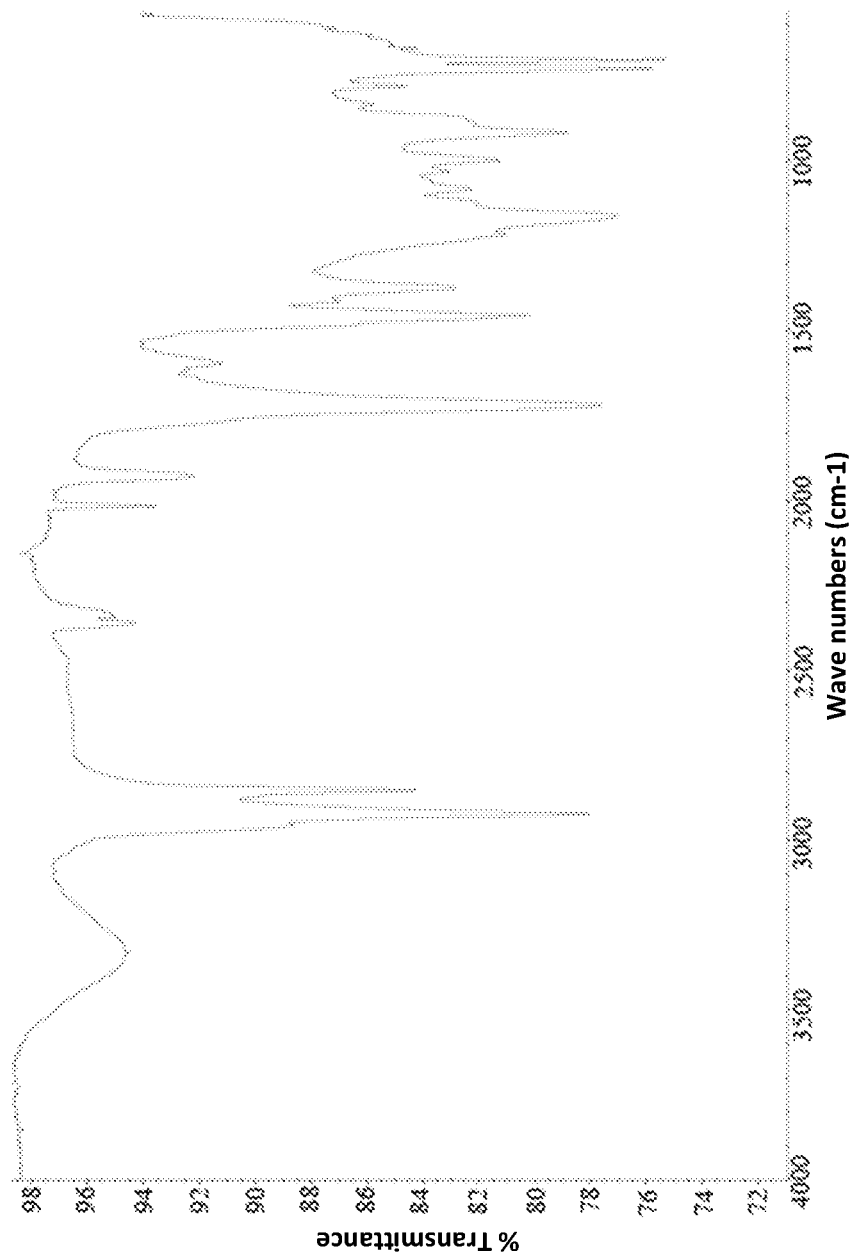
FIG. 38 is an FTIR spectrum of the linalool, acrylic acid and benzyldimethyltetradecylammonium chloride polymer product in an embodiment of the disclosure.
Figure 39:
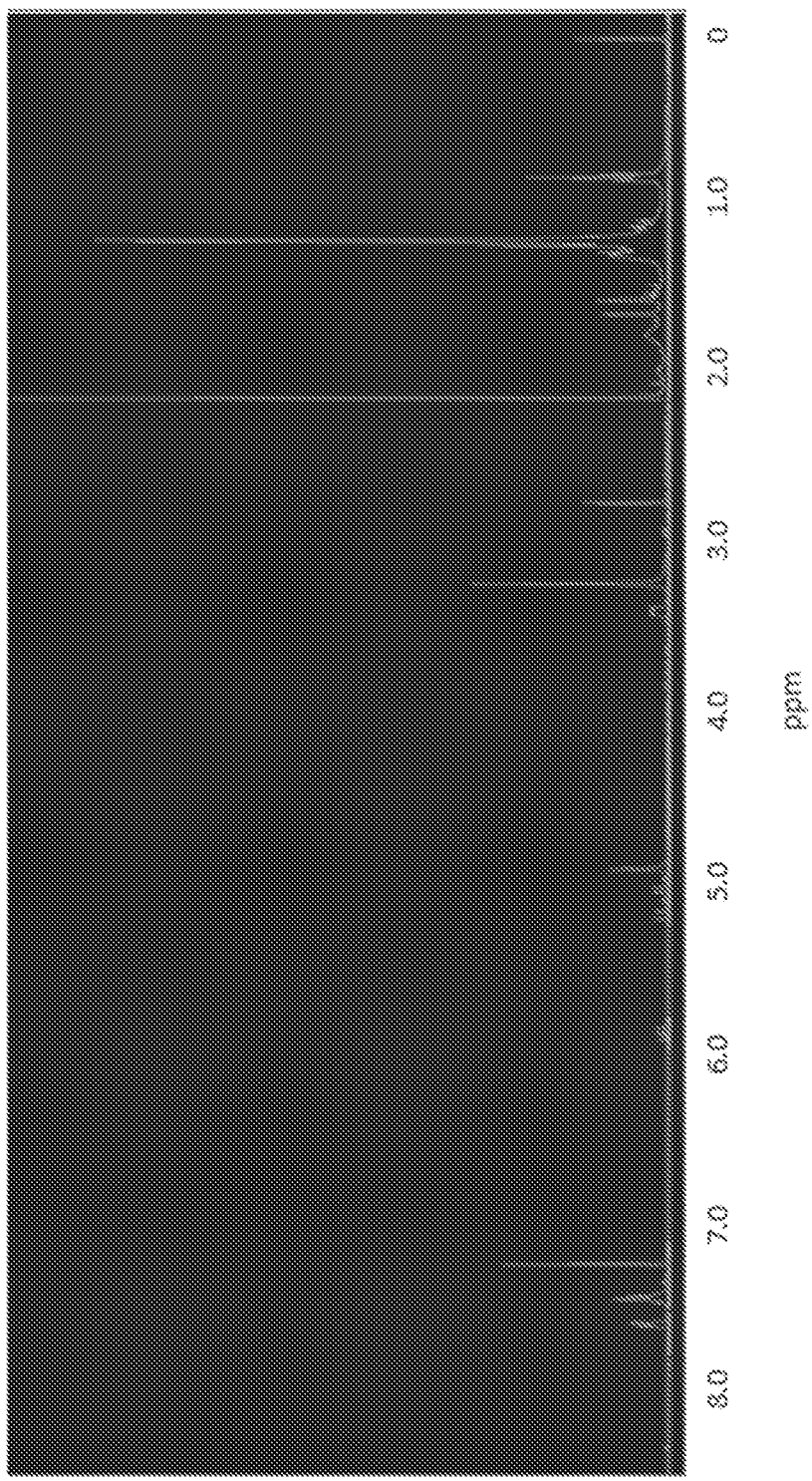
FIG. 39 is a $^1$H NMR spectrum of the linalool, acrylic acid and benzyldimethyltetradecylammonium chloride polymer product in an embodiment of the disclosure.
Figure 40:
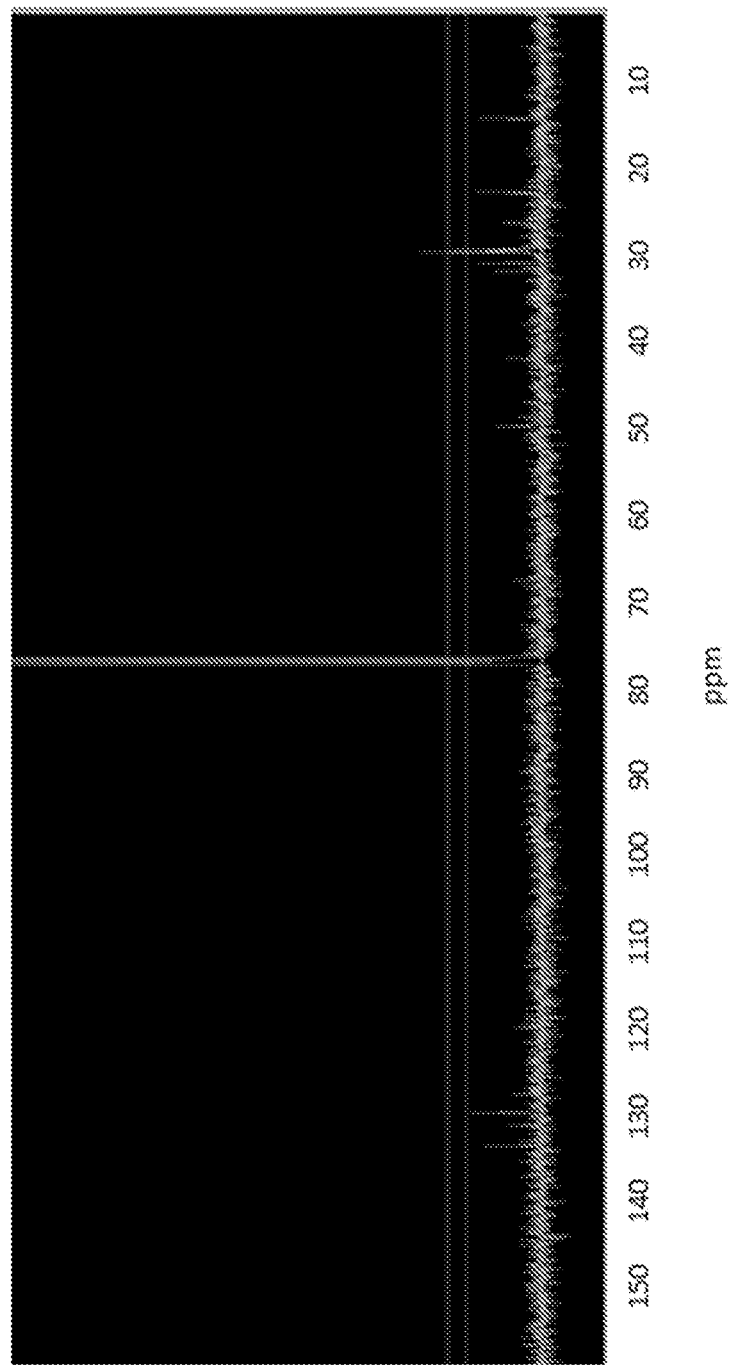
FIG. 40 is a $^{13}$C NMR spectrum of the linalool, acrylic acid and benzyldimethyltetradecylammonium chloride polymer product in an embodiment of the disclosure.

Example 19—Preparation of Anti-Microbial Polymer Using Acrylic Acid, Linalool and Benzyldimethyltetradecylammonium Chloride In a three neck flask 1 ml of Linalool (LIN), 0.214 ml of acrylic acid (AA) and 0.97 g of benzyldimethyltetradecylammonium chloride (BZ), were mixed under magnetic stirring and gentle heating until the BZ was completely melted, and the solution mixed to form a clear solution. The solution was then heated to 110° C., and 0.73 ml of 30% hydrogen peroxide solution (H2O2) was added, with the heat and stirring left on. Upon the addition of H2O2 the temperature dropped to 90° C. but within 30 seconds rose back up to 110° C. The temperature continued to rise and the solution began to turn yellow, then orange and darkened. The temperature reached a high of 150° C. after 24 minutes and stayed at this temperature for another 16 minutes when the heat as turned off and the product collected. The final product is a very viscous orange/brown liquid. The reaction products are similar to those schematically depicted in Scheme 6, where in this particular reaction R is a C14H29 alkyl chain, A is a chloride anion, and B, C, C' and B' are monomers of the copolymer, in this instance they optionally represent LIN monomers or AA monomers, oligomers or polymers. An FTIR, $^1$H and $^{13}$C NMR spectrum of the product is presented in FIGS. 38, 39 and 40 respectively.

Figure 41:
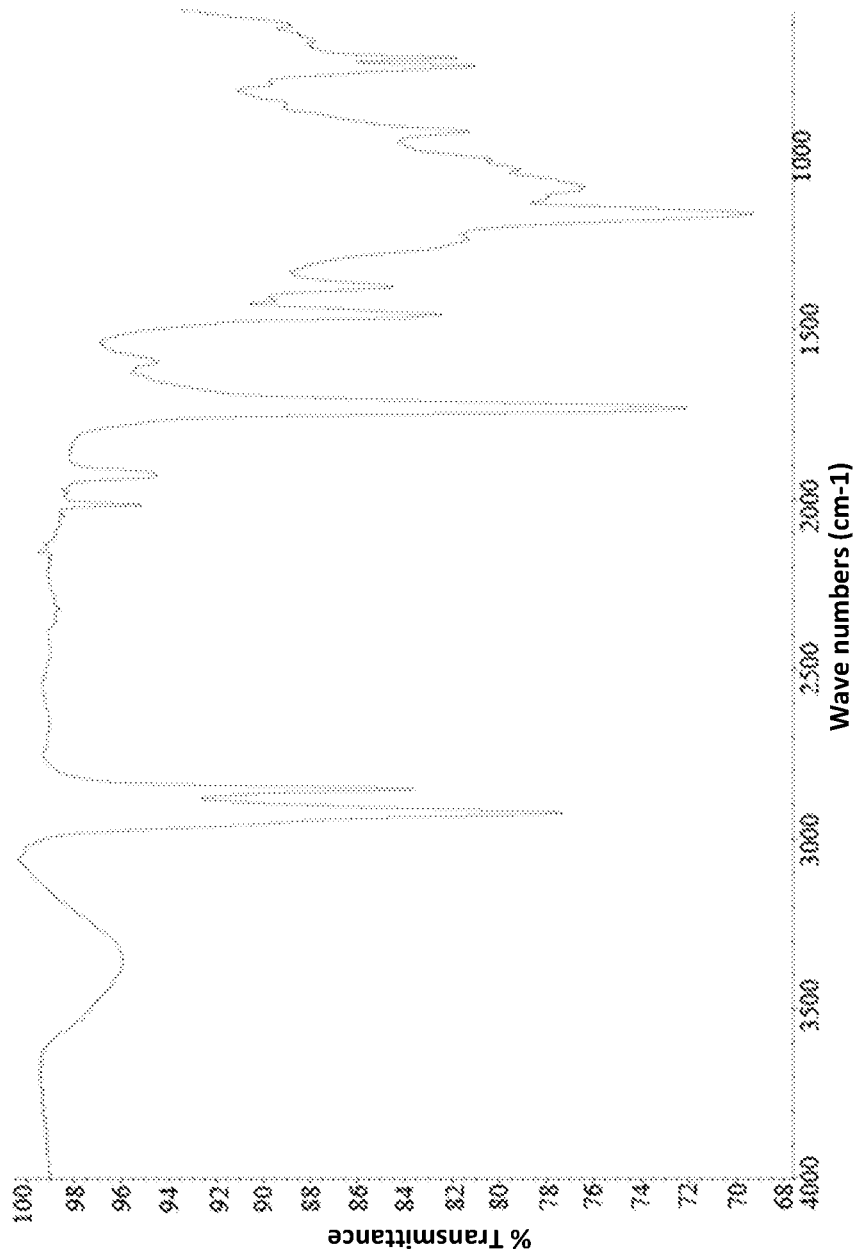
FIG. 41 is an FTIR spectrum of the epoxidized acrylated soybean oil, linalool and benzyldimethyltetradecylammonium chloride polymer product in an embodiment of the disclosure.
Figure 42:
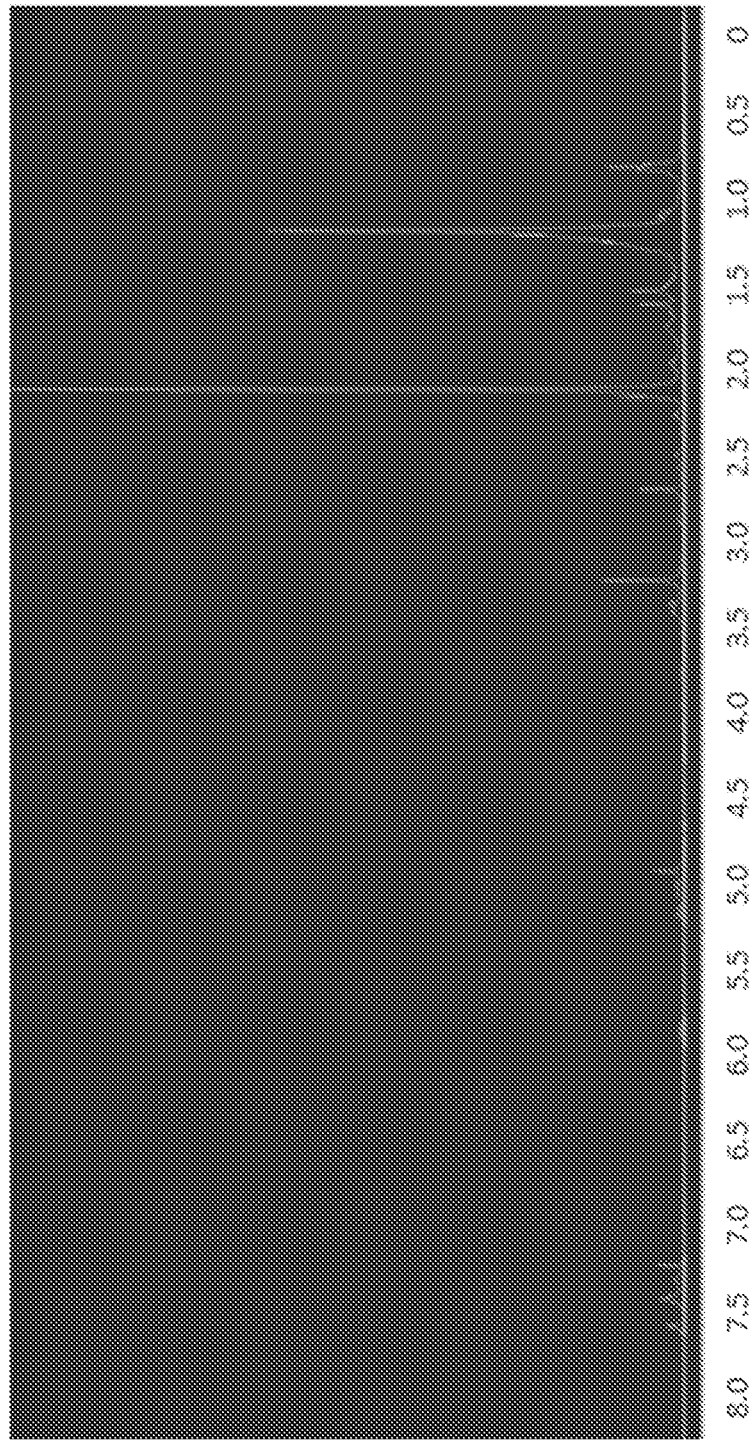
FIG. 42 is an $^1$H NMR spectrum of the linalool, epoxidized acrylated soybean oil and benzyldimethyltetradecylammonium chloride polymer product in an embodiment of the disclosure.
Figure 43:
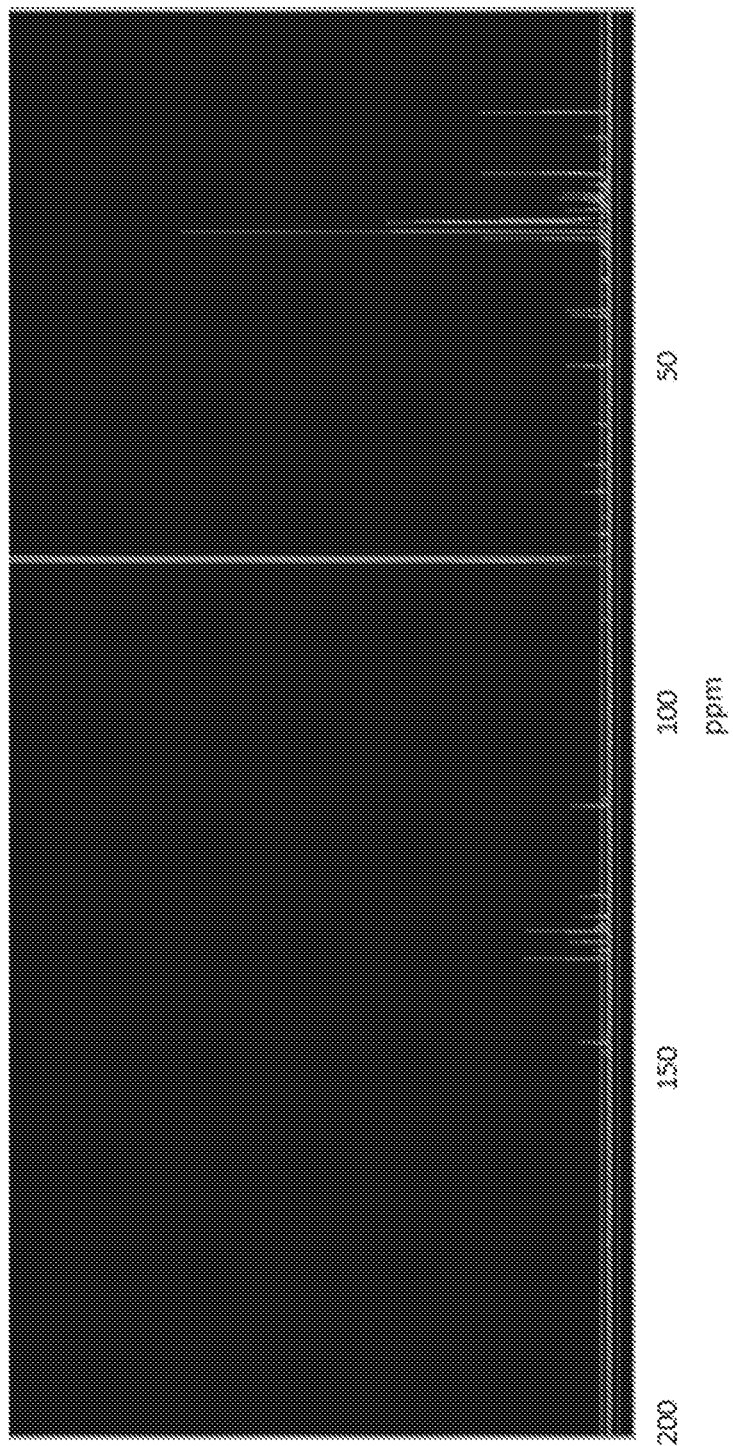
FIG. 43 is a $^{13}$C NMR spectrum of the linalool, epoxidized acrylated soybean oil and benzyldimethyltetradecylammonium chloride polymer product in an embodiment of the disclosure.

Example 20—Preparation of Anti-Microbial Polymer Using Soybean Oil Epoxidized Acrylate, Linalool, and Benzyldimethyltetradecylammonium Chloride In a three neck flask 2 ml of Linalool (LIN), 2.06 ml of Soybean oil, epoxidized acrylate (EASO) and 2 g of benzyldimethyltetradecylammonium chloride (BZ), were mixed under magnetic stirring and gentle heating until the BZ was completely melted, and the solution mixed to form a clear solution. The solution was then heated to 110° C., and 2 ml of 30% hydrogen peroxide solution (H2O2) was added, with the heat and stirring left on. Upon the addition of $H_2O_2$ the temperature dropped down to 85° C. and after 10 minutes the temperature increased to 110° C. and the solution was boiling gently. The solution reached a maximum of 180° C. and started turning brown after 20 minutes when the heat was turned off, and the product left to cool down to room temperature. The final product is a patchy brown/white soft solid that is gel-like in nature. An FTIR, $^1$H and $^{13}$C NMR spectrum of the product is presented in FIGS. 41, 42 and 43 respectively.

Figure 44:
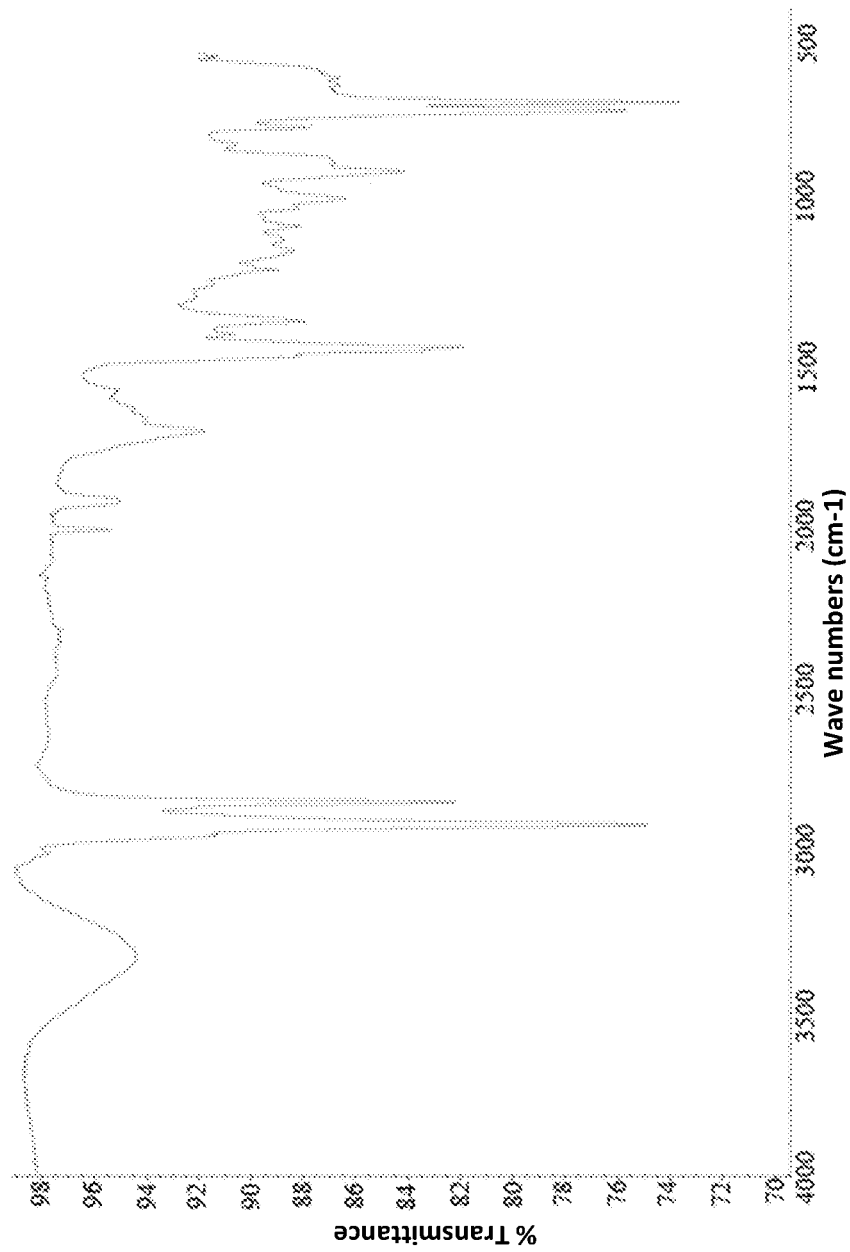
FIG. 44 is an FTIR spectrum of the Linalool and benzyldimethyltetradecylammonium chloride polymer product in an embodiment of the disclosure.
Figure 45:
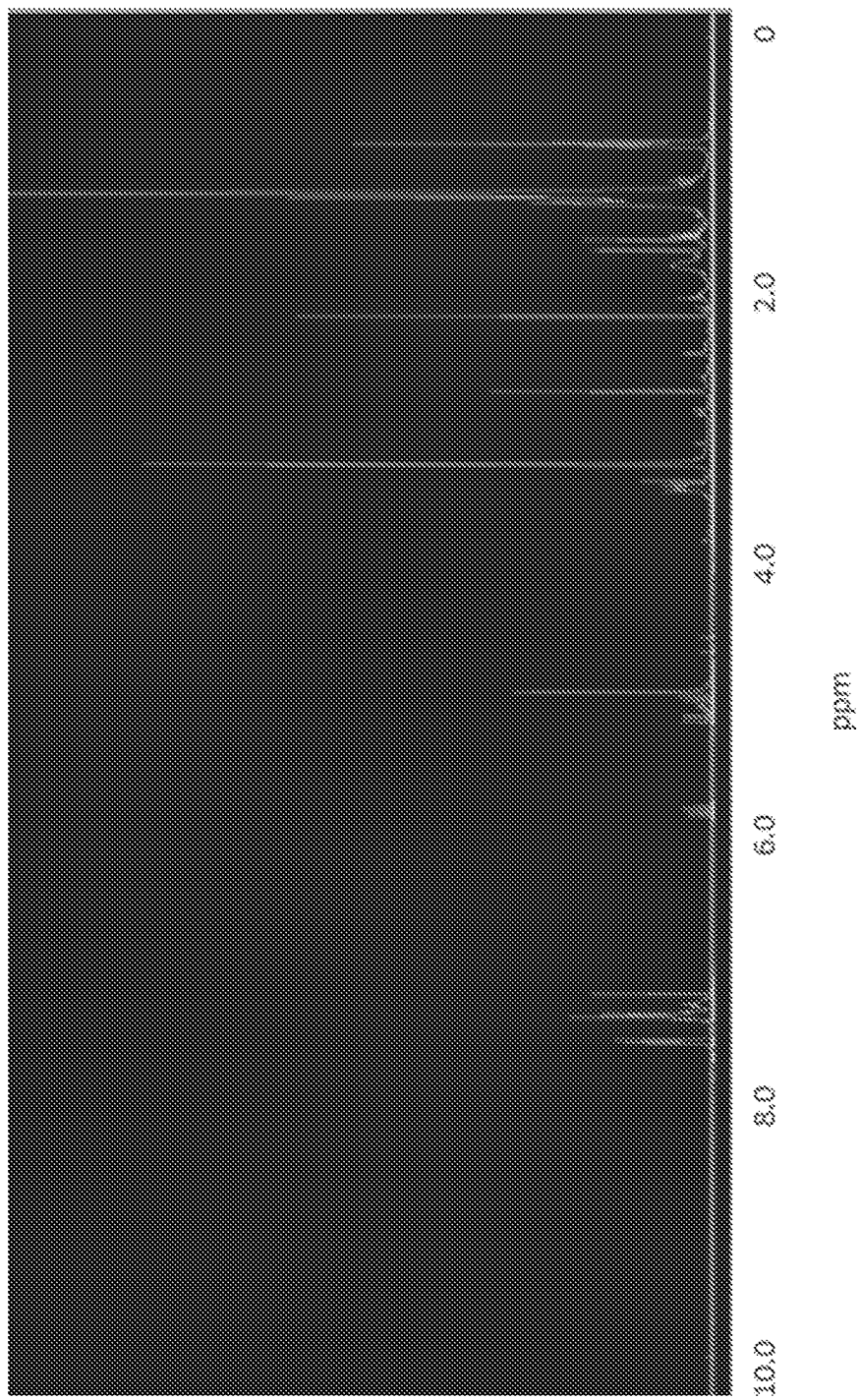
FIG. 45 is a $^1$H NMR spectrum of the linalool and benzyldimethyltetradecylammonium chloride polymer product in an embodiment of the disclosure.
Figure 46:
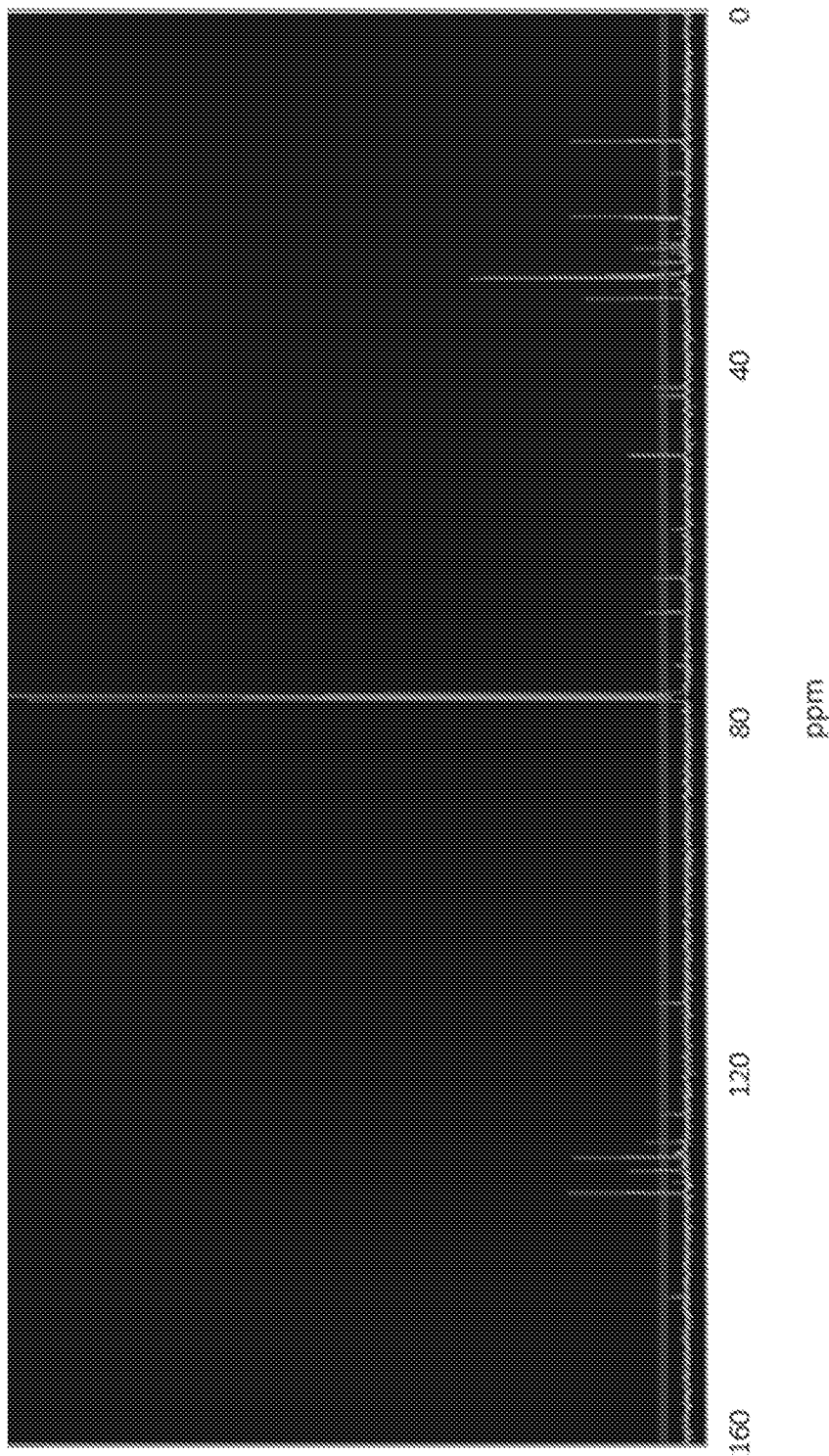
FIG. 46 is a $^{13}$C NMR spectrum of the linalool and benzyldimethyltetradecylammonium chloride polymer product in an embodiment of the disclosure.

Example 21—Preparation of Anti-Microbial Polymer Using Linalool, and Benzyldimethyltetradecylammonium Chloride In a three neck flask 1 ml of Linalool (LIN), and 1.93 g of benzyldimethyltetradecylammonium chloride (BZ), were mixed under magnetic stirring and gentle heating until the BZ was completely melted, and the solution mixed to form a clear solution. The solution was then heated to 110° C., and 0.93 ml of 30% hydrogen peroxide solution (H2O2) was added, with the heat and stirring left on. Upon addition of $H_2O_2$ the temperature decreased to 85° C. and the only visible changes were gentle boiling. As the solution continued to be heated it began to turn yellow and continued to darken to brown. The temperature reached a high of 180° C. after 16 minutes and then began to fall. After 17 minutes the heat was turned off and upon cooling became a very viscous brown liquid. The reaction products are similar to those schematically depicted in Scheme 8, where in this particular reaction R is a C14H29 alkyl chain, A is a chloride anion, and C in this particular reaction is linalool. An FTIR, $^1$H and $^{13}$C NMR spectrum of the product is presented in FIGS. 44, 45 and 46 respectively.

Example 22—Anti-Microbial Activity

Antibacterial Preliminary Susceptibility Testing Protocol

Compounds were tested for antibacterial activity, as described in Ma et al. (2011), against pure cultures of *Escherichia coli, Pseudomonas aeruginosa, Bacillus cereus, Proteus mirabilis/hauseri*, and *Staphylococcus aureus*, supplied by Ward's Natural Science Ltd. (St. Catherines, Ontario, Canada). All cultures were maintained on Tryptic Soy agar. These cultures were then transferred using an inoculation loop to 10 mL of Tryptic soy broth, and grown at 37° C. for 24 hours. Triplicates of plate and broth cultures were made in case of error or contamination.

Using a sterile swab, and aseptic techniques, the bacterial broth inocula were transferred to Mueller-Hinton plates and spread evenly, ensuring that the entire surface was inoculated. They were then left to dry for 3-5 minutes.

The following control discs were used: Penicillin (10 µg), Tetracycline (30 µg), Chloramphenicol (30 µg), and Ampicillin (10 µg). Four antibiotic discs containing different compounds were placed equidistant from each other on a Mueller-Hinton plate. Each compound had four replicates per species.

Plates were incubated for 18-24 hrs at 37° C., and then observed for rings of inhibition. If clear rings of inhibition were present, the diameter was measured twice using a caliper. Absence of rings of inhibition indicated a failed test, meaning the compound does not show enough antibacterial activity to be used in further testing.

Preparation of Novel Compound Discs

Each novel compound was applied to sterile filter paper discs as a solution (15 mg of compound in 3 mL of solvent). Each disc received 20 µL of solution, and was allowed to dry, giving a final concentration of 100 µg of compound per disc.

Protocol for Antimicrobial Susceptibility Testing on Filamentous Fungi and Yeasts Adapted from Messer et al., (2007), this protocol was used to test novel compounds for antifungal properties against yeasts and fungi. Compounds were tested for antifungal activity against pure cultures of *Saccharomyces cerevisiae, Candida albicans* supplied by Ward's Natural Science Ltd. and *Aspergillus niger* and *Aspergillus fumigatus* supplied by Alere Inc. (Inverness Medical, Ottawa, Ontario, Canada). All cultures were maintained on Sabouraud agar. The cultures of *S. cerevisiae*, and *C. albicans* were transferred, using an inoculation loop, to Erlenmeyer flasks containing 100 mL of Malt Yeast Extract Broth, and grown with shaking at 15° C. for 48 hrs. The cultures of *A. niger* and *A. fumigatus* were transferred, using an inoculation loop, to new Sabouraud agar and grown for 48 hrs. at 27° C., and 35° C. respectively, to cause sporulation. Triplicates of all the plates and broth cultures were made in case of error or contamination.

Using a sterile swab, and aseptic techniques, the cell suspension of *S. cerevisiae*, and *C. albicans* were transferred to Sabouraud agar plates and spread evenly, ensuring that the entire surface was inoculated. They were then left to dry for 10 minutes. The plates containing *A. niger* and *A. fumigatus* were covered with 5 mL of 0.85% saline solution, which by using aseptic technique was transferred to 10 mL of 0.85% of saline solution containing 0.2% Tween 80. The 0.2% Tween 80 reduces the hydrophobicity of the conidia, allowing the spores to be readily suspended (Messer et al., 2007). Alternatively two small circles containing fungal growth of the *A Niger* or *A Fumigatus* fungi were cut from the agar plates, and using a glass/PTFE tissue homoginzer, were mixed and homogenized with 5 ml of sterile MilliQ water to create a suspension of fungal spores. Using a sterile swab, and aseptic techniques, the spore inocula of *A. niger* and *A. fumigatus* were transferred to Sabouraud agar plates and spread evenly, ensuring that the entire surface was inoculated. They were then left to dry for 10 minutes.

Amphotericin B (100 µg) in acetone was used as a control. Four antibiotic discs containing different compounds were place equidistant apart on each Sabouraud plate. Each compound had four replicates per species.

Plates containing *S. cerevisiae*, and *C. albicans* were incubated for 18-24 hrs at 37° C., *A. niger* for 48 hrs at room temperature, and *A. fumigatus* for 18-24 hrs at 35° C. After incubation, the plates were observed for rings of inhibition. If clear rings of inhibition were present, the diameter was measured twice using a caliper. Halos indicated partial inhibition of growth (Hicks et al., 2008). Absence of a ring of inhibition constitutes a failed test, meaning the compound did not show enough antifungal activity to be used in further testing.

Antibiotic Disk Susceptibility Testing Results
1. Poly Acrylic Acid in Methanol
2. PVP-CELL-BZ (High) in CHCl$_3$
3. PAA-BZ in THF
4. PAA-CELL-BZ in THF
5. PAA-BZ+H2O in Methanol
6. PAA-PVP-BZ in H2O
7. PVP-BZ in CDCl3
8. PVP-CELL-BZ (Low) in CHCl3
9. Penicillin (P 10 ug)
10. Tetracycline (Te 30 ug)
11. Chloramphenicol (C 30 ug)
12. Ampicillin (AM 10 ug)
13. Amphotericin B (Yeasts 50 ug/Filamentous 100 ug).
14. Amphotericin B (20 µg)
15. Benzyldimethyltetradecylammonium chloride, (BZ) in acetone
16. BYOL-BZ in THF (am18)
17. BEOL-Bz in THF (am16)
18. STY-BZ in THF (AM2)
19. VA-BZ in THF (am3)
20. LIN-BZ in THF
21. LIN-BZ-AA
22. BZ homopolymer The results of the above-noted compounds are shown in Tables 9 and 10.

Example 23—Preparation of Anti-Microbial Paper Towels

First, antimicrobial polymers of acrylic acid and benzyl dimethyl alkyl ammonium chloride (C8-18) were prepared using the procedure described in example 1 with hydrogen peroxide used as the initiator, and benzyl dimethyl alkyl (C8-18) ammonium chloride used instead of benzyldimethyltetradecylammonium chloride. This solution is referred to as PAA-Bz-H A 30% weight glue solution of the resulting polymer was prepared by mixing the antimicrobial polymer with distilled water. The glue solution was then sprayed on the sheets of 2 ply white paper towels at various add-on rates of 100, 125, 150, 250 and 350 mg/ft$^2$ respectively. The paper towels were then allowed to dry.

After, 5 cm from each edge of the paper towels was cut out (to prevent edge areas where spraying might have been irregular being tested), and from the remaining paper towels, a single hole punch machine was used to punch 6 mm paper discs from each of the paper towels. These discs were then tested for anti-microbial activity as per the protocol described in example 24 and the results summarized in Tables 11 and 12.

Example 24—Toxicity Testing of Antimicrobial Polymers

The environmental toxicity of the antimicrobial paper towel wipes, were characterized, by performing a rapidtoxkit test by Microbiotests Inc, using the *Thamnocephalus platyurus* crustacean.

The samples were prepared by weighing and then dissolving 1 2 ply sheet of each of the paper towels of interest (150 and 350 mg/ft$^2$) and Cascades® anti-microbial paper towels containing benzalkonium chloride as the active ingredient, in 1 L of EPA moderate-hard synthetic freshwater prepared as per EPA guidelines (*Methods for Measuring the Acute Toxicity of Effluents and Receiving Waters to Freshwater and Marine Organisms*, 2002). The samples were then diluted using the EPA moderate-hard synthetic freshwater to a concentration of 200 μg/L of initial paper towel weight in solution. Additionally samples of the polymeric antimicrobial solution used to prepare the paper towels (from example 23), PAA-Bz-H, were also dissolved in the EPA moderate-hard synthetic freshwater and diluted to concentrations of 2, 20, 60 and 200 μg/L for the tests.

The rapid thamnocephalus test was carried out as per the standard operating procedure of the rapidtoxkit (*Standard Operational Procedure of the Rapidtoxkit*, 2004). Briefly, larvae of *Thamnocephalus platyurus* aged 30-45 h were exposed for 1 h to the samples prepared above in comparison to a control. A suspension of red microspheres was subsequently added for ingestion by the test organisms for 30 min. The larvae were then killed by addition of a fixative solution provided in the kit. The animals were collected from the test tubes and transferred to an observation plate for microscopical examination of the presence or absence of red particles in the digestive tract. The larvae in the controls have a digestive tract that is colored deeply red, whereas stressed (intoxicated) larvae do not ingest any particles and have an empty digestive tract. Some microspheres can, however, be taken up at the highest test dilutions. The quantitative importance of the toxic effects is rated by determination of the percentage of test biota with colored digestive tracts in the test dilutions versus that in the controls. The % inhibition of particle uptake of the various samples were determined as per the instructions of the toxkit, where a value at or below 30% is considered non-toxic, and anything higher requires greater investigation into toxicity effects. The results are summarized in table 13. The LC50 of the polymeric spray solution was also calculated as 98.58 μg/L, demonstrating that at a spray add-on rate of 150 mg/ft$^2$, the sample is close to the non-toxic threshold, and even at higher add-on rates, lower aquatic toxicity relative to the Cascades® anti-microbial towels.

TABLE 1

Reactions varying the ratios of PAA and CELL using 46 mL of H$_2$O (water) as a solvent, 1 g of BZ, 4 ml of Isopropanol and 0.3 g of AIBN in the reaction mixture

| Sample | PAA (mL) | Cellulose (g) | Initiator | Yield (%) |
|---|---|---|---|---|
| 1 | 1 | 0.25 | AIBN | 50 |
| 2 | 5 | 0.5 | AIBN | 85 |
| 3 | 5 | 0.25 | AIBN | 91 |
| 4 | 5 | 0.1 | AIBN | 87 |
| 5 | 5 | 0 | AIBN | 92 |
| 6 | 1 | 0.5 | H$_2$O$_2$ | 30 |

TABLE 2

Reactions varying the ratios of PAA and CELL using 50 mL of H$_2$O (water) as a solvent, 1 g of BZ, and 0.3 g of AIBN in the reaction mixture

| Sample | AA (mL) | Cellulose (g) | Initiator | Yield (%) |
|---|---|---|---|---|
| 1 | 1 | 0.5 | AIBN | 50 |
| 2 | 5 | 0.5 | AIBN | 85 |
| 3 | 5 | 0.25 | AIBN | 91 |
| 4 | 5 | 0.1 | AIBN | 87 |
| 5 | 5 | 0 | AIBN | 92 |
| 6 | 1 | 0.5 | H$_2$O$_2$ | 30 |

TABLE 3

3.0 g BZ + 2.0 g PAA + 0.125 g AIBN + 20.0 mL H2O at 23.7 C.

| | speed | spindle | reading | Viscosity |
|---|---|---|---|---|
| | 6 | 4 | 0.95 | 950 |
| | 12 | 4 | 1.8 | 900 |
| | 30 | 4 | 4.4 | 880 |
| | 60 | 4 | 8.9 | 890 |
| avg | | | | 905 |

TABLE 4

3.0 g BZ + 2.0 g PAA + 0.125 g AIBN + 22.0 mL H2O at 24.0 C.

| | speed | spindle | reading | viscosity |
|---|---|---|---|---|
| | 6 | 4 | 0.2 | 200 |
| | 6 | 4 | 0.2 | 200 |
| | 6 | 4 | 0.2 | 200 |
| avg | | | 0.2 | 200 |
| | 12 | 4 | 0.45 | 225 |
| | 12 | 4 | 0.48 | 240 |
| | 12 | 4 | 0.45 | 225 |
| avg | | | 0.46 | 230 |
| | 30 | 4 | 1 | 200 |
| | 30 | 4 | 1 | 200 |
| | 30 | 4 | 1 | 200 |
| avg | | | 1 | 200 |
| | 60 | 4 | 2.2 | 220 |
| | 60 | 4 | 2.15 | 215 |
| | 60 | 4 | 2.2 | 220 |
| | | | 2.183333 | 218.3333 |

TABLE 5

3.0 g BZ + 2.0 g PAA + 0.125 g AIBN + 24.0 mL H2O at 24.0 C.

|  | speed | spindle | reading | viscosity |
|---|---|---|---|---|
| avg |  |  |  |  |
|  | 30 | 4 | 0.45 | 90 |
|  | 30 | 4 | 0.5 | 100 |
|  | 30 | 4 | 0.45 | 90 |
| avg |  |  | 0.466667 | 93.33333 |
|  | 60 | 4 | 1 | 100 |
|  | 60 | 4 | 1 | 100 |
|  | 60 | 4 | 1 | 100 |
|  |  |  | 1 | 100 |

TABLE 6

3.0 g BZ + 2.0 g PAA + 0.125 g AIBN + 26.0 mL H2O at 23.8 C.

|  | speed | spindle | reading | viscosity |
|---|---|---|---|---|
|  | 30 | 3 | 0.8 | 32 |
|  | 30 | 3 | 0.8 | 32 |
|  | 30 | 3 | 0.75 | 30 |
| avg |  |  | 0.783333 | 31.33333 |
|  | 60 | 3 | 1.8 | 36 |
|  | 60 | 3 | 1.7 | 34 |
|  | 60 | 3 | 1.7 | 34 |
| avg | 60 | 3 | 1.8 | 36 |
|  |  |  | 1.75 | 35 |

TABLE 7

3.0 g BZ + 2.0 g PAA + 0.125 g AIBN + 26.0 mL H2O at 23.9 C.

|  | speed | spindle | reading | viscosity |
|---|---|---|---|---|
|  | 30 | 3 | 0.8 | 32 |
|  | 30 | 3 | 0.8 | 32 |
|  | 30 | 3 | 0.8 | 32 |
| avg |  |  | 0.8 | 32 |
|  | 60 | 3 | 1.8 | 36 |
|  | 60 | 3 | 1.8 | 36 |
|  | 60 | 3 | 1.8 | 36 |
| avg | 60 | 3 | 1.8 | 36 |
|  |  |  | 1.8 | 36 |

TABLE 8 viscosity and pH of solutions of PVP-BZ and PAA-BZ with the values reported as an average of 5 measurements at 24 C.

| Sample and Concentration (g per ml H$_2$O) | Viscosity (cP) | pH |
|---|---|---|
| PVP-BZ (High) (0.1333 g/ml) | 21.5 | 5 |
| PAA-BZ (0.222 g/ml) | 888 | 2 |
| PAA-BZ (0.044 g/ml) | 5.2 | 2 |
| PAA-BZ (0.022 g/ml) | 5.2 | 2 |

TABLE 9

Antibacterial Results

| | Gram+ | | Gram− | | |
|---|---|---|---|---|---|
| Compounds | B. cereus | S. aureus | E. coli | P. hauseri | P. aeruginosa |
| 1 | — | — | — | — | — |
| 2 | 8.70 | 10.10 | 9.10 | 8.57 | — |
| 3 | 9.10 | 10.20 | 8.92 | 8.74 | — |
| 4 | 9.10 | 11.00 | 8.92 | 9.27 | — |
| 5 | — | 9.30 | — | — | — |
| 6 | 8.40 | 9.30 | 8.39 | — | — |
| 7 | 10.10 | 9.80 | 9.10 | 8.39 | — |
| 8 | 12.70 | 9.80 | 9.10 | 8.22 | — |
| 9 | — | 31.50 | 15.91 | 11.00 | — |
| 10 | 20.30 | 23.30 | 20.45 | 29.50 | 10.75 |
| 11 | 26.30 | 17.70 | 32.25 | 16.50 | — |
| 12 | 13.50 | 28.80 | 17.13 | 19.00 | — |
| 15 | 14.30 | 13.43 | 12.70 | 12.63 | 8.13 |
| 16 | 14.60 | 13.20 | 10.90 | 12.77 | 8.67 |
| 17 | 14.73 | 15.57 | 11.50 | 12.40 | 8.10 |
| 18 | 13.07 | 13.37 | 11.23 | 13.30 | 7.90 |
| 19 | 11.70 | 12.97 | 12.47 | 13.90 | 8.43 |
| 20 | 9.4 | 9.3 | 8.8 | 9.4 | — |
| 21 | 11.7 | 7.8 | 8.1 | 18.3 | 9.0 |
| 22 | 7.9 | 7.3 | 8.7 | 8.3 | 8.1 |

TABLE 10

Antifungal Results

| | Yeast | | Filamentous Fungi | |
|---|---|---|---|---|
| Compounds | C. albicans | S. cerevisiae | A. niger | A. fumigatus |
| 1 | — | — | — | — |
| 2 | 9.18 | 9.56 | 8.04 | — |
| 3 | 8.04 | 9.09 | 8.22 | 8.04 |
| 4 | 8.22 | — | 8.04 | — |
| 5 | — | — | — | — |
| 6 | — | 9.27 | — | — |
| 7 | 8.65 | 9.27 | — | — |
| 8 | 8.39 | 9.27 | — | — |
| 13 | 9.35 | 8.39 | 17.86 | 11.19 |
| 14 | 11.00 | 10.80 | 8.80 | 7.80 |
| 15 | 7.48 | 11.33 | 10.97 | 8.13 |
| 16 | 9.27 | 11.07 | 9.90 | 9.00 |
| 17 | 10.13 | 11.50 | 9.53 | 9.80 |
| 18 | 9.73 | 9.67 | 8.97 | 7.90 |
| 19 | 9.93 | 10.90 | 9.10 | 8.93 |
| 20 | 8 | 14.5 | 8.7 | 12.6 |
| 21 | 7.93 | 7.6 | — | 9.8 |
| 22 | 8.67 | 10.6 | — | 13.4 |

TABLE 11

Antibacterial Results of Antimicrobial Paper Towels

| | Gram+ | | Gram− | | |
|---|---|---|---|---|---|
| Compounds | B. cereus | S. aureus | E. coli | P. hauseri | P. aeruginosa |
| B1 - 100 mg/ft | 10.5 | 11.7 | 8.0 | 15.3 | 10.3 |
| B2- 125 mg/ft | 15.7 | 18.5 | 6.8 | 8.7 | 15.0 |
| B3-150 mg/ft | 10.3 | 17.5 | 0.0 | 13.7 | 11.3 |
| T4-250 mg/ft | 12.7 | 15.5 | 8.1 | 14.7 | 12.7 |
| B5-350 mg/ft | 15.0 | 14.4 | 8.1 | 9.3 | 11.7 |
| CS - Cascades | 16.0 | 16.3 | 9.7 | 11.0 | 16.6 |
| 9 Penicillin (P 10 ug) | — | 31.5 | 15.91 | 11 | — |
| 10 Tetracycline (Te 30 ug) | 20.3 | 23.3 | 20.45 | 29.5 | 10.75 |

TABLE 11-continued

Antibacterial Results of Antimicrobial Paper Towels

| | | Gram+ | | Gram- | |
|---|---|---|---|---|---|
| Compounds | B. cereus | S. aureus | E. coli | P. hauseri | P. aeruginosa |
| 11 Chloramphenicol (C 30 ug) | 26.3 | 17.7 | 32.25 | 16.5 | — |
| 12 Ampicillin (AM 10 ug) | 13.5 | 28.8 | 17.13 | 19 | — |

TABLE 12

Antifungal Results of Antimicrobial Paper Towels

| | Yeast | | Filamentous Fungi | |
|---|---|---|---|---|
| Compounds | C. albicans | S. cerevisiae | A. niger | A. fumigatus |
| B1 - 100 mg/ft | 7.2 | 7.3 | — | — |
| B2- 125 mg/ft | — | 8.6 | — | 8.1 |
| B3-150 mg/ft | 7.6 | 7.7 | — | — |
| T4-250 mg/ft | 6.4 | — | — | — |
| B5-350 mg/ft | 8.2 | 9.6 | — | 8.5 |
| Cascades | 8.2 | 8.4 | — | 9.8 |
| PAA-BZ-H (100 µg of solution onto paper discs) | 10.6 | 10.8 | — | 15.8 |
| Amphotericin B (20 ug) AMB 20 | 9.7 | 13.4 | 8.7 | 9.4 |

TABLE 13

% Inhibition of Particle Uptake from Toxkit Testing

| Sample | % Inhibition of Particle Uptake |
|---|---|
| Cascades (200 mg/L) | 84.85 |
| 150 mg/ft² (200 mg/L) | 31.82 |
| 350 mg/ft² (200 mg/L) | 39.39 |
| PAA-Bz-H (200 ug/L) | 48.86 |
| PAA-Bz-H (20 ug/L) | 45.45 |
| PAA-Bz-H (2 ug/L) | 54.55 |
| PAA-Bz-H (60 ug/L) | 100.00 |

The invention claimed is:

1. An anti-microbial polymer, wherein the polymer comprises

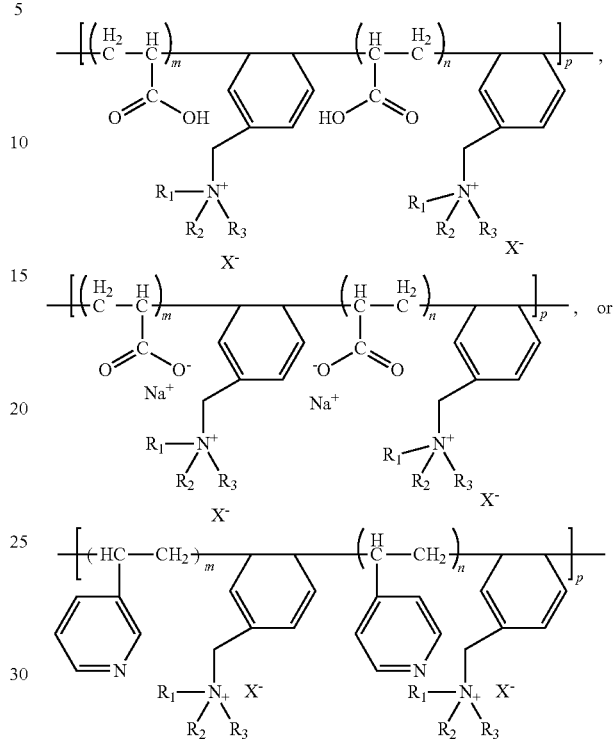

wherein $R_1$, $R_2$ and $R_3$ are independently or simultaneously optionally substituted H, $(C_1$-$C_{24})$-alkyl, $(C_2$-$C_{24})$-alkenyl, $(C_2$-$C_{24})$-alkynyl, $(C_6$-$C_{14})$-aryl, $(C_5$-$C_{14})$-heteroaryl or $(C_1$-$C_{10})$-alkylene-$(C_6$-$C_{14})$-aryl;

X is any suitable counteranion, and m, n and p are independently or simultaneously integers between 1 and 1,000,000.

2. The anti-microbial polymer of claim 1, wherein $R_1$ and $R_2$ are methyl, and $R_3$ is $(C_1$-$C_{24})$-alkyl.

3. An anti-microbial medical device comprising,
   i) a medical device formed from the anti-microbial polymer as defined in claim 1; or
   ii) anti-microbial polymer as defined in claim 1 coated on the device.

4. An anti-microbial packaging material comprising,
   i) a packaging material,
   ii) an anti-microbial polymer as defined in claim 1 coated on the material.

5. A composition comprising the anti-microbial polymer of claim 1, wherein the polymer is conjugated to cellulose or a cellulose derivative.

6. An anti-microbial polymer comprising

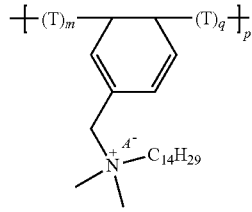

wherein,

T is made from a monomer of 2-butyne-1,4-diol, cis-butene-1,4-diol, styrene, vinyl acetate, acrylic acid, pentaerythritol allyl ether, linalool, soybean oil epoxidized acrylate, or combinations thereof;

m, q and p are integers between 1 and 1,000,000; and

A is a suitable counterion.

* * * * *